(12) United States Patent
Regueiro-Ren et al.

(10) Patent No.: US 9,969,767 B2
(45) Date of Patent: May 15, 2018

(54) OXOLUPENE DERIVATIVES

(71) Applicant: ViiV Healthcare UK (No.5) Limited, Brentford, Middlesex (GB)

(72) Inventors: Alicia Regueiro-Ren, Wallingford, CT (US); Zheng Liu, Wallingford, CT (US); Jacob Swidorski, Wallingford, CT (US); Nicholas A. Meanwell, Wallingford, CT (US)

(73) Assignee: ViiV Healthcare UK (No.5) Limited, Brentford, Middlesex (GB)

( * ) Notice: Subject to any disclaimer, the term of this patent is extended or adjusted under 35 U.S.C. 154(b) by 0 days. days.

(21) Appl. No.: 15/524,298

(22) PCT Filed: Nov. 12, 2015

(86) PCT No.: PCT/US2015/060344
§ 371 (c)(1),
(2) Date: May 4, 2017

(87) PCT Pub. No.: WO2016/077561
PCT Pub. Date: May 19, 2016

(65) Prior Publication Data
US 2017/0334946 A1 Nov. 23, 2017

Related U.S. Application Data

(60) Provisional application No. 62/079,977, filed on Nov. 14, 2014.

(51) Int. Cl.
C07J 53/00 (2006.01)
A61K 31/56 (2006.01)
C07J 63/00 (2006.01)

(52) U.S. Cl.
CPC .................... *C07J 63/008* (2013.01)

(58) Field of Classification Search
CPC .............. C07J 53/002; A61K 31/56
See application file for complete search history.

(56) References Cited

U.S. PATENT DOCUMENTS

2011/0077227 A1  3/2011  Moinet et al.
2013/0210787 A1  8/2013  Swidorski et al.

FOREIGN PATENT DOCUMENTS

| WO | 2011153315 A1 | 12/2011 |
| WO | 2011153319 A1 | 12/2011 |
| WO | 2012106188 A1 | 8/2012 |
| WO | 2013117137 A1 | 8/2013 |

*Primary Examiner* — Brenda L Coleman
(74) *Attorney, Agent, or Firm* — Robert H. Brink; Edward R. Gimmi; William R. Majarian

(57) ABSTRACT

Compounds having drug and bio-affecting properties, their pharmaceutical compositions and methods of use are set forth. In particular, betulinic acid derivatives that possess unique antiviral activity are provided as HIV maturation inhibitors, as represented by compounds of Formulas I and II:

Formula I

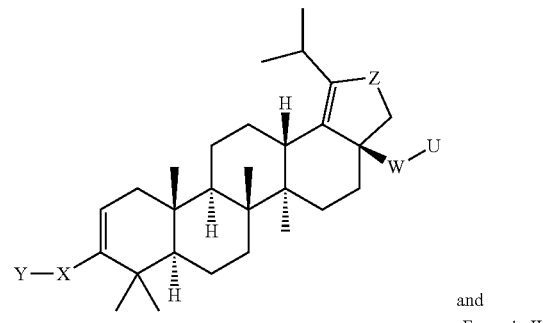

and

Formula II

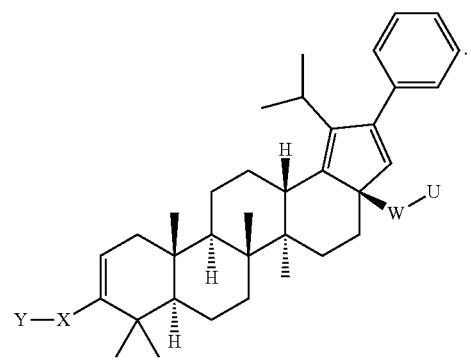

These compounds are useful for the treatment of HIV and AIDS.

6 Claims, No Drawings

OXOLUPENE DERIVATIVES

CROSS REFERENCE TO RELATED APPLICATION

This application is a § 371 of International Application No. PCT/US2015/060344, filed 12 Nov. 2015, which claims the benefit of U.S. Provisional Application No. 62/079,977, filed 14 Nov. 2014, which are incorporated herein in their entireties.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains –3TC plus AZT), TRIZIVIR® (contains abacavir, lamivudine, and zidovudine), EPZICOM® (contains abacavir and lamivudine), TRUVADA® (contains VIREAD® andEMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. No. 7,354,924 and U.S. Pat. No. 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., "Synthesis of derivatives of plant triterpenes and study of their antiviral and immunostimulating activity," Khimiya y Interesakh Ustoichivogo Razvitiya, Vol. 9, No. 3, pp. 485-491 (2001) (English abstract).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (now U.S. Pat. No. 8,754,068) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (now U.S. Pat. No. 8,802,661). Reference is also made to the application entitled "C-28

AMINES OF C-3 MODIFIED BETULINIC ACID DERIVATIVES AS HIV MATURATION INHIBITORS" U.S. Ser. No. 13/359,680, filed on Jan. 27, 2012 (now U.S. Pat. No. 8,748,415). In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012 (now U.S. Pat. No. 8,846,647). Further reference is also made to the application "C-3 CYCLOALKENYL TRITERPENOIDS WITH HIV MATURATION INHIBITORY ACTIVITY" filed U.S. Ser. No. 13/760,726 on Feb. 6, 2013 (now US 2013-0210787), as well as to the application entitled "ALKYLHALO-SUBSTITUTED C-3 CYCLOALKENYL TRITERPENOIDS WITH HIV MATURATION INHIBITORY ACTIVITY" filed U.S. Ser. No. 61/978,306 on Apr. 11, 2014.

What is now needed in the art are new compounds which are useful as HIV maturation inhibitors, as well as new pharmaceutical compositions containing these compounds.

SUMMARY OF THE INVENTION

The present invention provides compounds of Formulas I and II below, including pharmaceutically acceptable salts thereof, their pharmaceutical formulations, and their use in patients suffering from or susceptible to a virus such as HIV. The compounds of Formulas I and II are effective antiviral agents, particularly as inhibitors of HIV. They are useful for the treatment of HIV and AIDS.

One embodiment of the present invention is directed to a compound, including pharmaceutically acceptable salts thereof, which is selected from a compound of Formulas I and II:

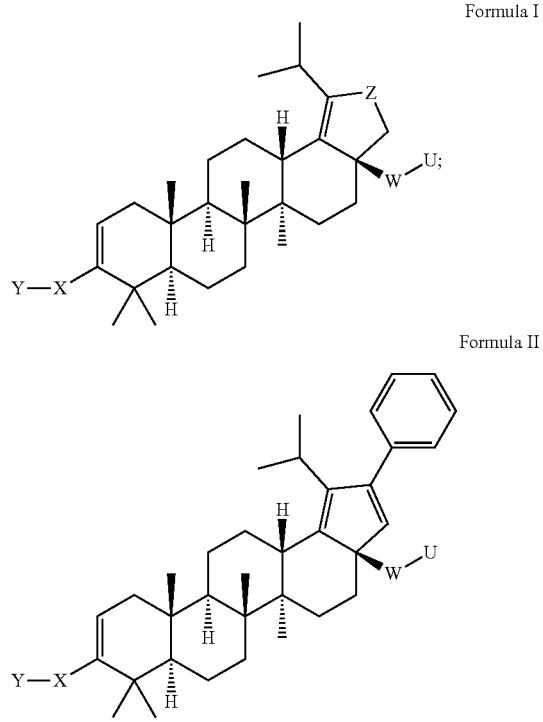

Formula I

Formula II wherein X is selected from the group of phenyl, heteroaryl, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{6-8}$ dioxacycloalkenyl, $C_{6-9}$ oxaspirocycloalkyl, and $C_{6-9}$ oxaspirocycloalkenyl ring; and further wherein X is substituted with A, wherein A is at least one member selected from the group of —H, -halo, -hydroxyl, —$C_{1-6}$ alkyl, —$C_{1-6}$ alkoxy, —$C_{1-6}$haloalkyl, —CN, —$NR_8R_9$, —$COOR_2$, —$CONR_2R_2$ and —$C_{1-6}$ alkyl-Q;

Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;

$R_2$ is —H, —$C_{1-6}$ alkyl, -alkylsubstituted $C_{1-6}$ alkyl or -arylsubstituted $C_{1-6}$ alkyl;

Y is selected from the group of —$COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkylsubstituted $C_{1-6}$ alkyl, —$COOR_2$, $CF_2$—$COOR_2$, —$NHC(O)(CH_2)_n$—$COOR_2$, —$SO_2NR_2C(O)R_2$, -tetrazole, and —CONHOH, wherein n=1–6;

$R_3$ is —H, —$C_{1-6}$ alkyl or -alkylsubstituted $C_{1-6}$ alkyl;

W is absent, or is —CO— or is selected from the group of

—$C_{2-6}$ alkyl-, —$C_{2-6}$ alkyl-CO—, —$C_{2-6}$ alkenyl-, —$C_{2-6}$ alkenyl-CO—, and -heteroaryl-; or is selected from the group of:

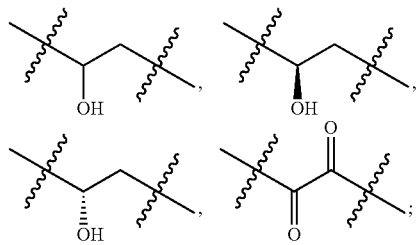

U is selected from —$NR_4R_5$ and $OR_2$,
with the proviso that U cannot be $OR_2$ when W is absent;
Z is selected from the group of —CO—, —CHOH, —C=N—$OR_2$, —C=N—$R_{24}$, and —CH—$NHR_{24}$
$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, and —$SO_2NR_2R_2$;

$Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;

with the proviso that $R_4$ or $R_5$ cannot be $COR_6$ or $COCOR_6$ when W is CO, and with the further proviso that only one of $R_4$ or $R_5$ can be selected from the group of —$COR_6$, —$COCOR_6$, —$SO_2R_7$ and —$SO_2NR_2R_2$;

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substituted-alkyl-$Q_2$, —$C_{3-6}$ cycloalkyl-$Q_2$, aryl-$Q_2$, —$NR_{13}R_{14}$, and —$OR_{15}$;

$Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —H, —$C_{1-6}$ alkyl, —$C_{1-6}$ substituted alkyl, —$C_{3-6}$ cycloalkyl, —$CF_3$, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_8$ and $R_9$ are taken together with the adjacent N to form a cycle selected from the group of:

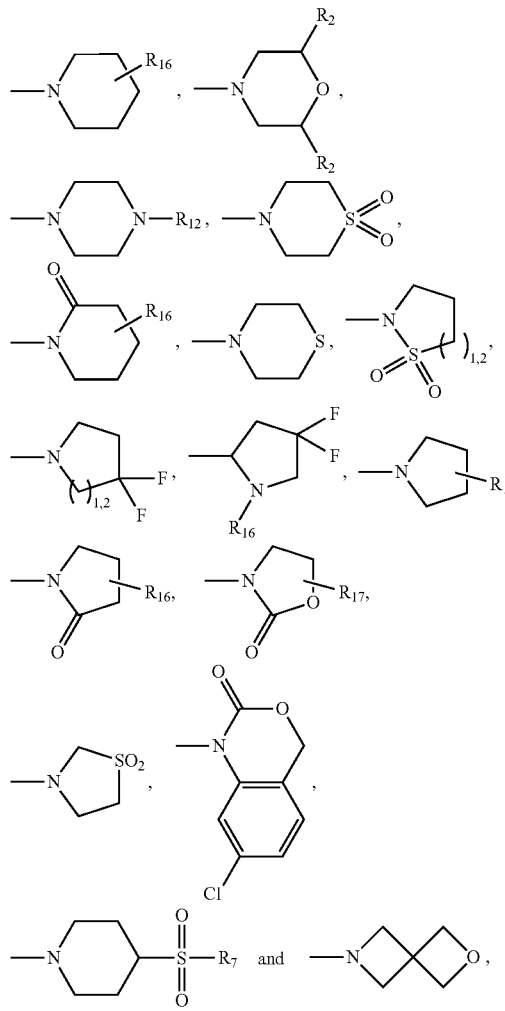

with the proviso that only one of $R_8$ or $R_9$ can be —$COOR_3$;

$R_{10}$ and $R_{11}$ are independently selected from the group of —H, —$C_{1-6}$ alkyl, —$C_{1-6}$ substituted alkyl and —$C_{3-6}$ cycloalkyl, or $R_{10}$ and $R_{11}$ are taken together with the adjacent N to form the cycle

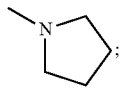

$R_{12}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, —$COR_7$, —$COONR_{22}R_{23}$, —$SOR_7$, and —$SONR_{24}R_{25}$;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$, $C_{1-6}$ substituted alkyl-$Q_3$ and

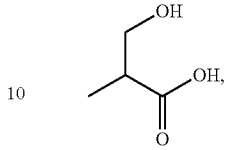

or $R_{13}$ and $R_{14}$ are taken together with the adjacent N to form a cycle selected from the group of:

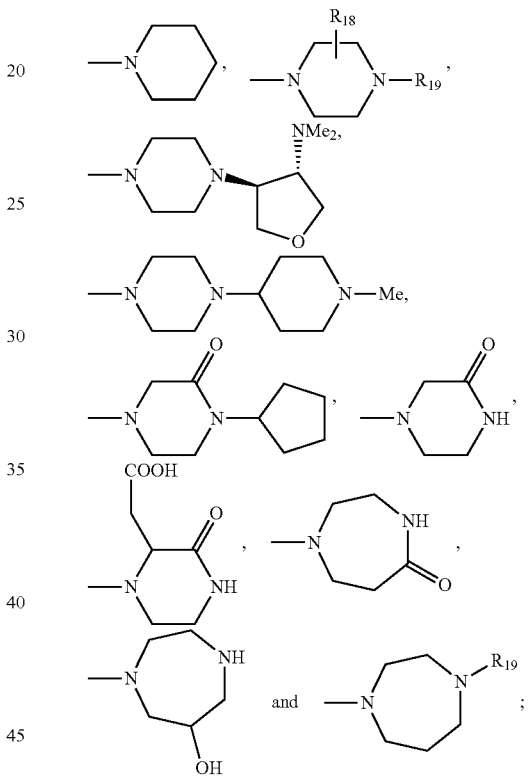

$Q_3$ is selected from the group of heteroaryl, substituted heteroaryl, —$NR_{20}R_{21}$, —$CONR_2R_2$, —$COOR_2$, —$OR_2$, and —$SO_2R_3$;

$R_{15}$ is selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$ and —$C_{1-6}$ substituted alkyl-$Q_3$;

$R_{16}$ is selected from the group of —H, —$C_{1-6}$ alkyl, —$NR_2R_2$, and —$COOR_3$;

$R_{17}$ is selected from the group of —H, —$C_{1-6}$ alkyl, —$COOR_3$, and aryl;

$R_{18}$ is selected from the group of —H, —$COOR_2$ and —$C_{1-6}$ alkyl-$COOR_2$;

$R_{19}$ is selected from the group of —H, —$C_{1-6}$ alkyl, —$C_{1-6}$ alkyl-$Q_4$, —$COR_3$, and —$COOR_3$;

$Q_4$ is selected from the group of —$NR_2R_2$ and —$OR_2$;

$R_{20}$ and $R_{21}$ are independently selected from the group of —H, —$C_{1-6}$ alkyl, —$C_{1-6}$ substituted alkyl, —$C_{1-6}$ substituted alkyl-$OR_2$, and —$COR_3$, or $R_{20}$ and $R_{21}$ are taken together with the adjacent N to form a cycle selected from the group of

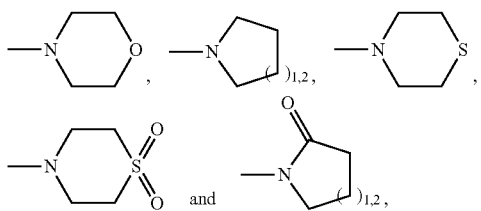

with the proviso that only one of $R_{20}$ or $R_{21}$ can be —$COR_3$, $R_{22}$ and $R_{23}$ are independently selected from the group of —H, —$C_{1-6}$ alkyl, —$C_{1-6}$ substituted alkyl, and —$C_{1-6}$ cycloalkyl, or $R_{22}$ and $R_{23}$ are taken together with the adjacent N to form a cycle selected from the group of

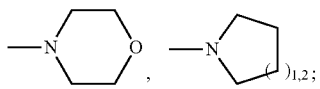

$R_{24}$ and $R_{25}$ are independently from the group of —H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl; and $Q_5$ is selected from the group of halogen and $SO_2R_3$.

In a further embodiment, there is provided a method for treating mammals infected with a virus, especially wherein said virus is HIV, comprising administering to said mammal an antiviral effective amount of a compound which is selected from the group of compounds of Formulas I and II, and one or more pharmaceutically acceptable carriers, excipients or diluents. Optionally, the compound of Formulas I and II can be administered in combination with an antiviral effective amount of another AIDS treatment agent selected from the group consisting of: (a) an AIDS antiviral agent; (b) an anti-infective agent; (c) an immunomodulator; and (d) HIV entry inhibitors.

Another embodiment of the present invention is a pharmaceutical composition comprising one or more compounds of Formulas I and II, and one or more pharmaceutically acceptable carriers, excipients, and/or diluents; and optionally in combination with another AIDS treatment agent selected from the group consisting of: (a) an AIDS antiviral agent; (b) an anti-infective agent; (c) an immunomodulator; and (d) HIV entry inhibitors.

In another embodiment of the invention there is provided one or more methods for making the compounds of Formulas I and II herein.

Also provided herein are intermediate compounds useful in making the compounds of Formulas I and II herein.

The present invention is directed to these, as well as other important ends, hereinafter described.

DETAILED DESCRIPTION OF THE EMBODIMENTS

As used herein, the singular forms "a", "an", and "the" include plural reference unless the context clearly dictates otherwise.

Since the compounds of the present invention may possess asymmetric centers and therefore occur as mixtures of diastereomers, the present disclosure includes the individual diastereoisomeric forms of the compounds of Formulas I and II in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) means straight or branched chain alkyl groups such as methyl, ethyl, propyl, isopropyl, butyl, isobutyl, t-butyl, amyl, hexyl, and the like.

"$C_1$-$C_4$ fluoroalkyl" refers to F-substituted $C_1$-$C_4$ alkyl wherein at least one H atom is substituted with an F atom, and each H atom can be independently substituted by an F atom;

"Halogen" or "halo" refers to chlorine, bromine, iodine or fluorine.

An "aryl" or "Ar" group refers to all carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group(s) are preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group of hydrogen, alkyl, cycloalkyl, aryl, carbonyl, C-carboxy, sulfonyl, trihalomethyl, and, combined, a five- or six-member heteroalicyclic ring.

A "heteroaryl" group refers to a monocyclic or fused ring (i.e., rings which share an adjacent pair of atoms) group having in the ring(s) one or more atoms selected from the group of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted, the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

A "heteroalicyclic" group refers to a monocyclic or fused ring group having in the ring(s) one or more atoms selected from the group of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and its S oxides and tetrahydropyranyl. When substituted, the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, 0-carboxy, sulfinyl, sulfonyl, sulfonamido, trihalo-methanesulfonamido, trihalomethanesulfonyl, silyl, amidino, guanidino, ureido, phosphonyl, amino and —$NR^xR^y$ with $R^x$ and $R^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(=O)O-group, with R" as defined herein. A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$— groups with Z as defined above.

A "trihalomethanesulfonamido" group refers to a $Z_3CS$(=O)$_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —S(=O)$_2R$" group with R" being $(C_{1-6})$alkyl.

A "S-sulfonamido" group refers to a —S(=O)$_2NR^xR^y$, with $R^x$ and $R^y$ independently being H or $(C_{1-6})$alkyl.

A "N-sulfonamido" group refers to a R"S(=O)$_2NR^x$— group, with $R^x$ being H or $(C_{1-6})$alkyl.

A "O-carbamyl" group refers to a —OC(=O)$NR^xR^y$ group, with $R^x$ and $R^y$ independently being H or $(C_{1-6})$alkyl.

A "N-carbamyl" group refers to a $R^xOC$(=O)$NR^y$ group, with $R^x$ and $R^y$ independently being H or $(C_{1-6})$alkyl.

A "O-thiocarbamyl" group refers to a —OC(=S)$NR^xR^y$ group, with $R^x$ and $R^y$ independently being H or $(C_{1-6})$alkyl.

A "N-thiocarbamyl" group refers to a $R^xOC$(=S)$NR^y$— group, with $R^x$ and $R^y$ independently being H or $(C_{1-6})$alkyl.

An "amino" group refers to an —$NH_2$ group.

A "C-amido" group refers to a —C(=O)$NR^xR^y$ group, with $R^x$ and $R^y$ independently being H or $(C_{1-6})$alkyl.

A "C-thioamido" group refers to a —C(=S)NR$^x$R$^y$ group, with R$^x$ and R$^y$ independently being H or (C$_{1-6}$)alkyl.

A "N-amido" group refers to a R$^x$C(=O)NR$^y$— group, with R$^x$ and R$^y$ independently being H or (C$_{1-6}$)alkyl.

An "ureido" group refers to a —NR$^x$C(=O)NR$^y$R$^{y2}$ group, with R$^x$, R$^y$, and R$^{y2}$ independently being H or (C$_{1-6}$)alkyl.

A "guanidino" group refers to a —R$^x$NC(=N)NR$^y$R$^{y2}$ group, with R$^x$, R$^y$, and R$^{y2}$ independently being H or (C$_{1-6}$)alkyl.

A "amidino" group refers to a R$^x$R$^y$NC(=N)— group, with R$^x$ and R$^y$ independently being H or (C$_{1-6}$)alkyl.

A "cyano" group refers to a —CN group.

A "silyl" group refers to a —Si(R")$_3$, with R" being (C$_{1-6}$)alkyl or phenyl.

A "phosphonyl" group refers to a P(=O)(OR$^x$)$_2$ with R$^x$ being (C$_{1-6}$)alkyl.

A "hydrazino" group refers to a —NR$^x$NR$^y$R$^{y2}$ group, with R$^x$, R$^y$, and R$^{y2}$ independently being H or (C$_{1-6}$)alkyl.

A "4, 5, or 6 membered ring cyclic N-lactam" group refers to

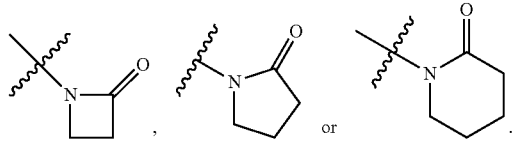

A "spiro" group is a bicyclic organic group with rings connected through just one atom. The rings can be different in nature or identical. The connecting atom is also called the spiroatom, most often a quaternary carbon ("spiro carbon").

An "oxospiro" or "oxaspiro" group is a spiro group having an oxygen contained within the bicyclic ring structure. A "dioxospiro" or "dioxaspiro" group has two oxygens within the bicyclic ring structure.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound, including pharmaceutically acceptable salts thereof, which is selected from a compound of Formulas I and II:

Formula I

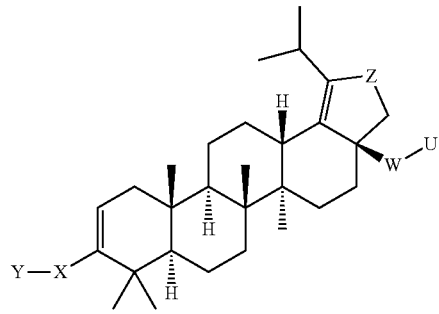

Formula II

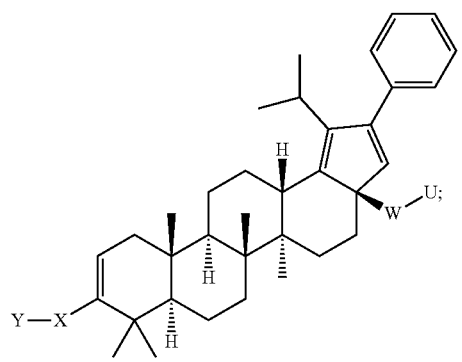

wherein X is selected from the group of phenyl, heteroaryl, C$_{4-8}$ cycloalkyl, C$_{4-8}$ cycloalkenyl, C$_{4-9}$ spirocycloalkyl, C$_{4-9}$ spirocycloalkenyl, C$_{4-8}$ oxacycloalkyl, C$_{6-8}$ dioxacycloalkyl, C$_{6-9}$ oxaspirocycloalkyl, and C$_{6-9}$ oxaspirocycloalkenyl ring;

and further wherein X is substituted with A, wherein A is at least one member selected from the group of —H, -halo, -hydroxyl, —C$_{1-6}$ alkyl, —C$_{1-6}$ alkoxy, —C$_{1-6}$haloalkyl, —CN, —NR$_8$R$_9$, —COOR$_2$, —CONR$_2$R$_2$ and —C$_{1-6}$ alkyl-Q;

Q is selected from the group of aryl, heteroaryl, substituted heteroaryl, —OR$_2$, —COOR$_3$, —NR$_2$R$_2$, —SO$_2$R$_7$, —CONHSO$_2$R$_3$, and —CONHSO$_2$NR$_2$R$_2$;

R$_2$ is —H, —C$_{1-6}$ alkyl, -alkylsubstituted C$_{1-6}$ alkyl or -arylsubstituted C$_{1-6}$ alkyl;

Y is selected from the group of —COOR$_2$, —C(O)NR$_2$SO$_2$R$_3$, —C(O)NHSO$_2$NR$_2$R$_2$, —NR$_2$SO$_2$R$_2$, —SO$_2$NR$_2$R$_2$, —C$_{3-6}$ cycloalkyl-COOR$_2$, —C$_{2-6}$ alkenyl-COOR$_2$, —C$_{2-6}$ alkynyl-COOR$_2$, —C$_{1-6}$ alkyl-COOR$_2$, -alkylsubstituted C$_{1-6}$ alkyl, —COOR$_2$, $CF_2$—$COOR_2$, —$NHC(O)(CH_2)_n$—$COOR_2$, —$SO_2NR_2C(O)R_2$, -tetrazole, and —$CONHOH$, wherein n=1–6;

$R_3$ is —H, —$C_{1-6}$ alkyl or -alkylsubstituted $C_{1-6}$ alkyl;

W is absent, or is —CO— or is selected from the group of —$C_{2-6}$ alkyl-, —$C_{2-6}$ alkyl-CO—, —$C_{2-6}$ alkenyl-, —$C_{2-6}$ alkenyl-CO—, and -heteroaryl-; or is selected from the group of:

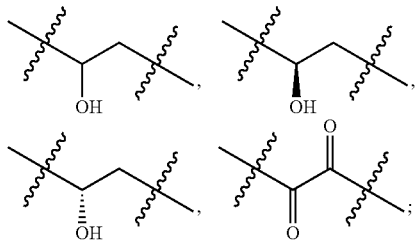

U is selected from —$NR_4R_5$ and $OR_2$, with the proviso that U cannot be $OR_2$ when W is absent;

Z is selected from the group of —CO—, —CHOH, —C=N—$OR_2$, —C=N—$R_{24}$ and —CH—$NHR_{24}$;

$R_4$ is selected from the group of —H, —$C_{1-6}$ alkyl, —$C_{1-6}$alkyl-$C(OR_3)_2$—$C_{3-6}$cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, and —$SO_2NR_2R_2$;

$Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COR_6$, —$COCOR_6$, —$SO_2R_7$ and —$SO_2NR_2R_2$;

with the proviso that $R_4$ or $R_5$ cannot be $COR_6$ or $COCOR_6$ when W is CO, and with the further proviso that only one of $R_4$ or $R_5$ can be selected from the group of —$COR_6$, —$COCOR_6$, —$SO_2R_7$ and —$SO_2NR_2R_2$;

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substitutedalkyl-$Q_2$, —$C_{3-6}$ cycloalkyl-$Q_2$, aryl-$Q_2$, —$NR_{13}R_{14}$, and —$OR_{15}$;

$Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;

$R_7$ is selected from the group of —H, —$C_{1-6}$ alkyl, —$C_{1-6}$ substituted alkyl, —$C_{3-6}$ cycloalkyl, —$CF_3$, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$, or $R_8$ and $R_9$ are taken together with the adjacent N to form a cycle selected from the group of:

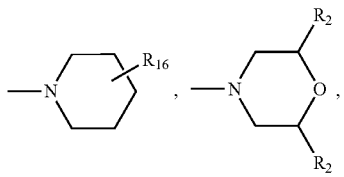

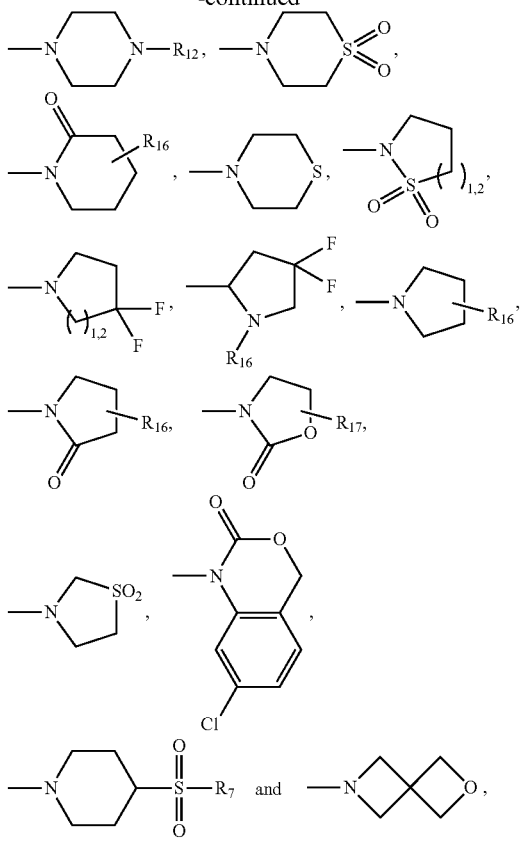

with the proviso that only one of $R_8$ or $R_9$ can be —$COOR_3$;

$R_{10}$ and $R_{11}$ are independently selected from the group of —H, —$C_{1-6}$ alkyl, —$C_{1-6}$ substituted alkyl and —$C_{3-6}$ cycloalkyl, or $R_{10}$ and $R_{11}$ are taken together with the adjacent N to form the cycle

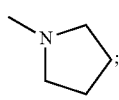

$R_{12}$ is selected from the group of —H, —$C_{1-6}$ alkyl, —$C_{1-6}$ alkyl-OH; —$C_{1-6}$ alkyl, —$C_{1-6}$ substituted alkyl, —$C_{3-6}$ cycloalkyl, —$COR_7$, —$COONR_{22}R_{23}$, —$SOR_7$, and —$SONR_{24}R_{25}$;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$, $C_{1-6}$ substituted alkyl-$Q_3$ and

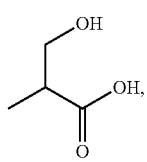

or $R_{13}$ and $R_{14}$ are taken together with the adjacent N to form a cycle selected from the group of:

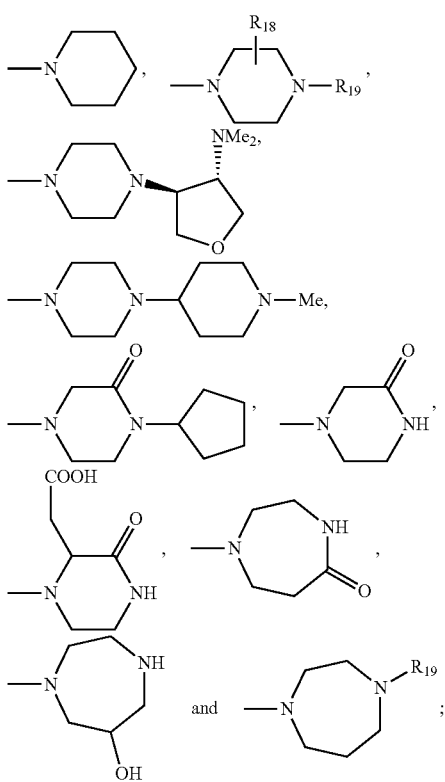

and 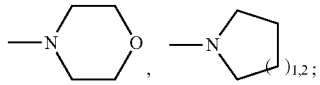 ;

Q₃ is selected from the group of heteroaryl, substituted heteroaryl, —NR₂₀R₁₂, —CONR₂R₂, —COOR₂, —OR₂, and —SO₂R₃;

R₁₅ is selected from the group of —H, —C$_{1-6}$ alkyl, —C$_{3-6}$ cycloalkyl, —C$_{1-6}$ substituted alkyl, —C$_{1-6}$ alkyl-Q₃, —C$_{1-6}$ alkyl-C$_{3-6}$ cycloalkyl-Q₃ and —C$_{1-6}$ substituted alkyl-Q₃, R₁₆ is selected from the group of —H, —C$_{1-6}$ alkyl, —NR₂R₂, and —COOR₃;

R₁₇ is selected from the group of —H, —C$_{1-6}$ alkyl, —COOR₃, and aryl;

R₁₈ is selected from the group of —H, —COOR₂ and —C$_{1-6}$ alkyl-COOR₂;

R₁₉ is selected from the group of —H, —C$_{1-6}$ alkyl, —C$_{1-6}$ alkyl-Q₄, —COR₃, and —COOR₃;

Q₄ is selected from the group of —NR₂R₂ and —OR₂;

R₂₀ and R₂₁ are independently selected from the group of —H, —C$_{1-6}$ alkyl, —C$_{1-6}$ substituted alkyl, —C$_{1-6}$ substituted alkyl-OR₂, and —COR₃, or R₂₀ and R₂₁ are taken together with the adjacent N to form a cycle selected from the group of with the proviso that only one of R₂₀ or R₂₁ can be —COR₃;

R₂₂ and R₂₃ are independently selected from the group of —H, —C$_{1-6}$ alkyl, —C$_{1-6}$ substituted alkyl, and —C$_{1-6}$ cycloalkyl, or R₂₂ and R₂₃ are taken together with the adjacent N to form a cycle selected from the group of R₂₄ and R₂₅ are independently from the group of —H, —C$_{1-6}$ alkyl, —C$_{1-6}$ substituted alkyl, —C$_{1-6}$ alkyl-Q₅, —C$_{1-6}$ cycloalkyl, aryl, substituted aryl, heteroaryl, and substituted heteroaryl; and Q₅ is selected from the group of halogen and SO₂R₃.

In a preferred embodiment of the invention, X is phenyl or is C$_{4-8}$ cycloalkenyl. When X is C$_{4-8}$ cycloalkenyl, it is preferred to be C₆ cycloalkenyl.

It is also preferred that Y is —COOH.

It is further preferred that A is —C$_{1-6}$ haloalkyl. Halo is preferably -fluoro.

In a further embodiment, it is preferred that Z is —CO—.

Preferred compounds, including pharmaceutically acceptable salts thereof, as part of the invention include the following:

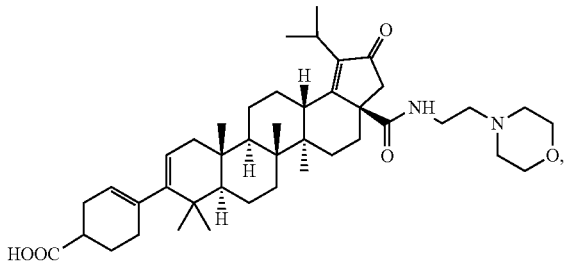

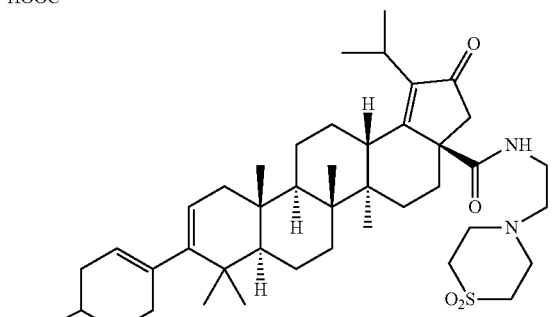

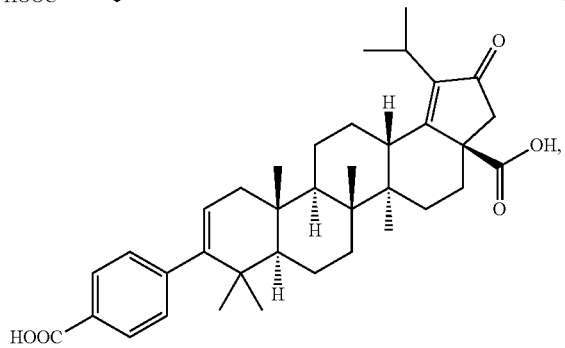

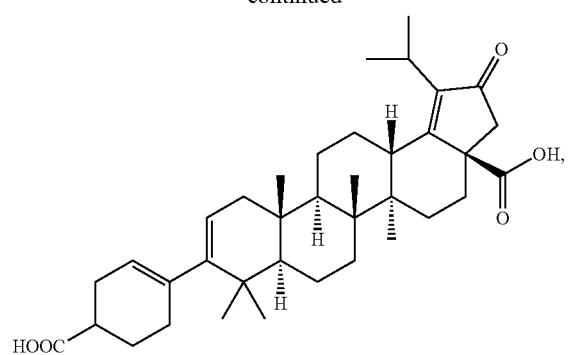
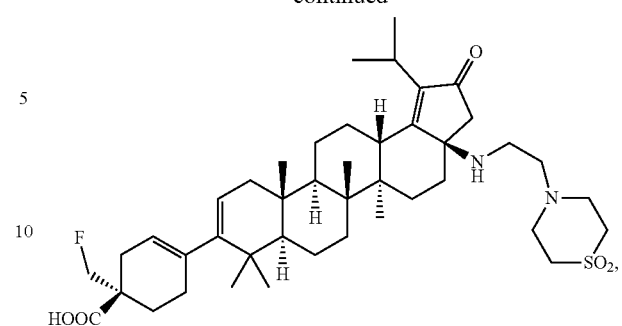
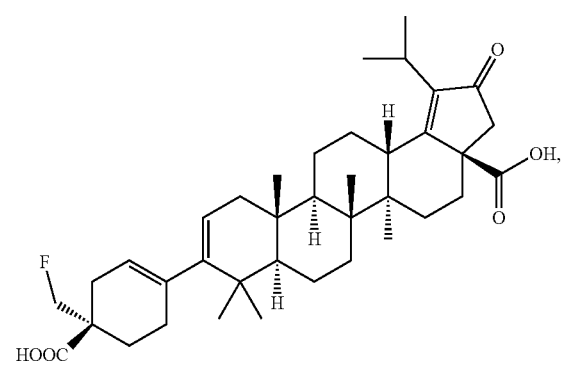
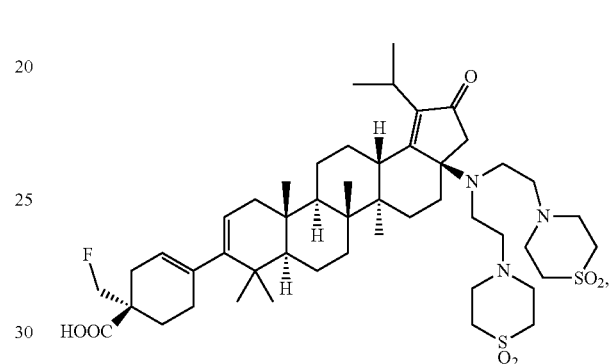
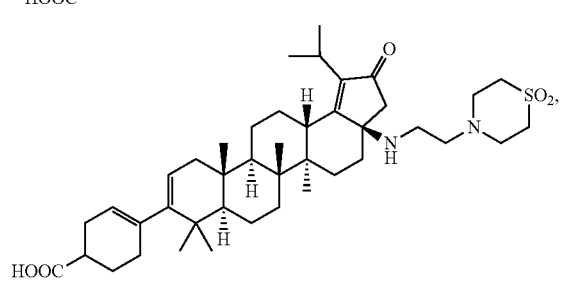
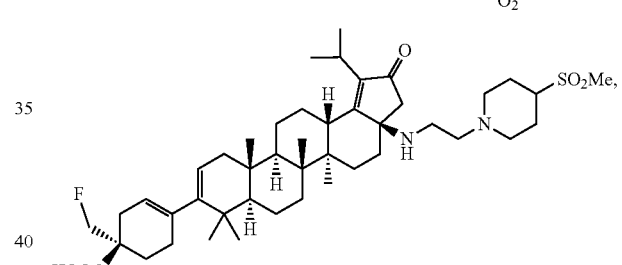
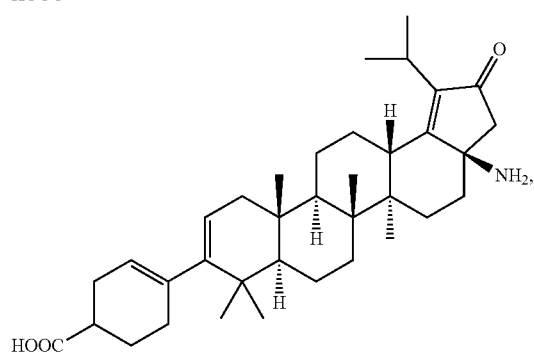
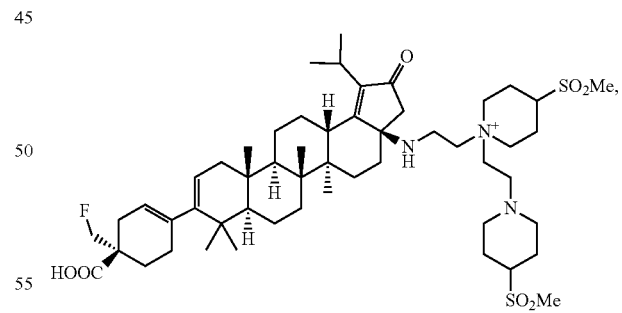
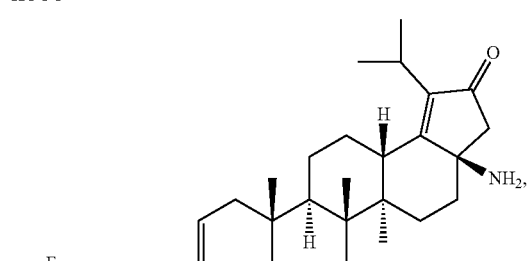
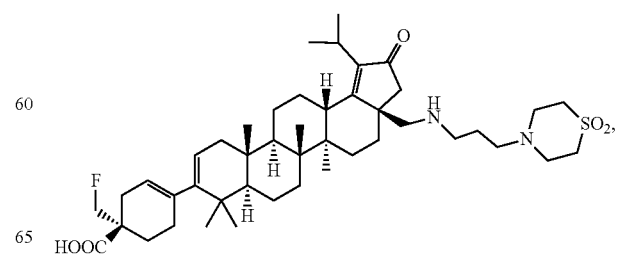

-continued

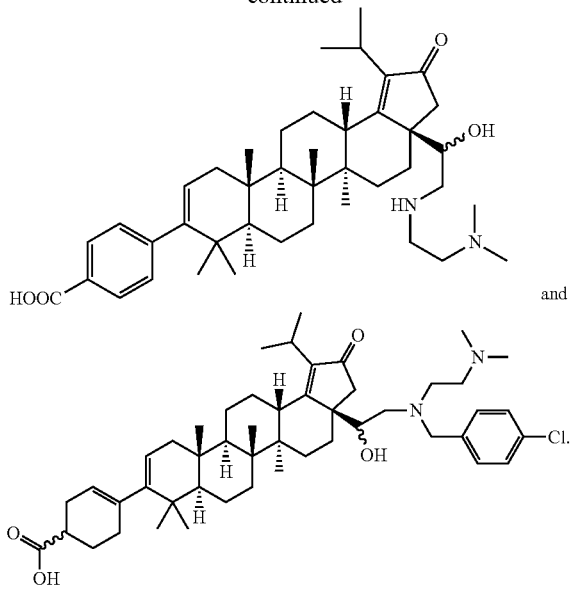

The compounds above represent the mixture of diastereoisomers, and the two individual disastereomers. In certain embodiments, one of the specific diastereomers may be particularly preferred.

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I and II together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, inhibiting, ameliorating and/or healing diseases and conditions associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I and II herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| ANTIVIRALS | | |
|---|---|---|
| Drug Name | Manufacturer | Indication |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |

ANTIVIRALS

| Drug Name | Manufacturer | Indication |
|---|---|---|
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |

ANTIVIRALS

| Drug Name | Manufacturer | Indication |
|---|---|---|
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ® Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDS in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor dolutegravir | GSK | HIV infection AIDs |
| S/GSK1265744 Integrase inhibitor | GSK | HIV infection AIDs |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute Schering Plough | AIDS, ARC Kaposi's sarcoma w/AZT, AIDS |
| Alpha-2 Interferon | | |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |

-continued

| ANTI-INFECTIVES | | |
| --- | --- | --- |
| Drug Name | Manufacturer | Indication |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells*. Meanwell, Nicholas A.; Kadow, John F., Current Opinion in Drug Discovery & Development (2003), 6(4), 451-461. Specifically the compounds can be utilized in combination with attachment inhibitors, fusion inhibitors, and chemokine receptor antagonists aimed at either the $CCR_5$ or $CXCR_4$ coreceptor. HIV attachment inhibitors are also set forth in U.S. Pat. No. 7,354,924 and U.S. Pat. No. 7,745,625.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound(s) of the present invention and other active agents may be administered separately or in conjunction. In addition, the administration of one element may be prior to, concurrent to, or subsequent to the administration of other agent(s).

General Chemistry (Methods of Synthesis)

The present invention comprises compounds of Formulas I and II, their pharmaceutical formulations, and their use in patients suffering from or susceptible to HIV infection. The compounds of Formulas I and II also include pharmaceutically acceptable salts thereof. Procedures to construct compounds of Formulas I and II and intermediates useful for their synthesis are described after the Abbreviations.

Abbreviations

One or more of the following abbreviations, most of which are conventional abbreviations well known to those skilled in the art, may be used throughout the description of the disclosure and the examples:

RT=room temperature
BHT=2,6-di-tert-butyl-4-hydroxytoluene
CSA=camphorsulfonic acid
LDA=lithium diisopropylamide
KHMDS=potassium bis(trimethylsilyl)amide
SFC=supercritical fluid chromatography
Quant=quantitative
TBDMS=tert-butyldimethylsilane
PTFE=polytetrafluoroethylene
NMO=4-methylmorpholine-N-oxide
THF=tetrahydrofuran
TLC=thin layer chromatography
DCM=dichloromethane
DCE=dichloroethane
TFA=trifluoroacetic acid
LCMS=liquid chromatography mass spectroscopy
Prep=preparative
HPLC=high performance liquid chromatography
DAST=(diethylamino)sulfur trifluoride
TEA=triethylamine
DIPEA=N,N-diisopropylethylamine
HATU=[O-(7-azabenzotriazol-1-yl)-1,1,3,3-tetramethyluronium hexafluorophosphate]
DCC=N,N'-dicyclohexylcarbodiimide
DMAP=dimethylaminopyridine
TMS=trimethylsilyl
NMR=nuclear magnetic resonance
DPPA=diphenyl phosphoryl azide
AIBN=azobisisobutyronitrile
TBAF=tetrabutylammonium fluoride
DMF=dimethylformamide TBTU=O-(benzotriazol-1-yl)-N,N,N',N'-tetramethyluronium tetrafluoroborate
Min(s)=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf₂NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
µg=microgram(s)
µl=microliter(s)
µm=micrometer(s)
mm=millimeter(s)
Rpm=revolutions per minute
SM=starting material
TLC=thin layer chromatography
AP=area percentage
Equiv.=equivalent(s)
DMP=Dess-Martin periodinane
TMSCl=trimethylsilyl chloride
TBSCl=tert-Butyldimethylsilyl chloride
TBSOTf=trimethylsilyl trifluoromethanesulfonate
PhMe=toluene
PhNTf₂=N-Phenyl-bis(trifluoromethanesulfonimide)
S-Phos=2-Dicyclohexylphosphino-2',6'-dimethoxybiphenyl
TFDO=methyl(trifluoromethyl)dioxirane
TEMPO=2,2,6,6-tetramethylpiperidinyloxy
DI=deionized water The terms "C-3" and "C-28" refer to certain positions of a triterpene core as numbered in accordance with IUPAC rules (positions depicted below with respect to an illustrative triterpene: betulin):

The same numbering is maintained when referring to the compound series in schemes and general descriptions of methods.

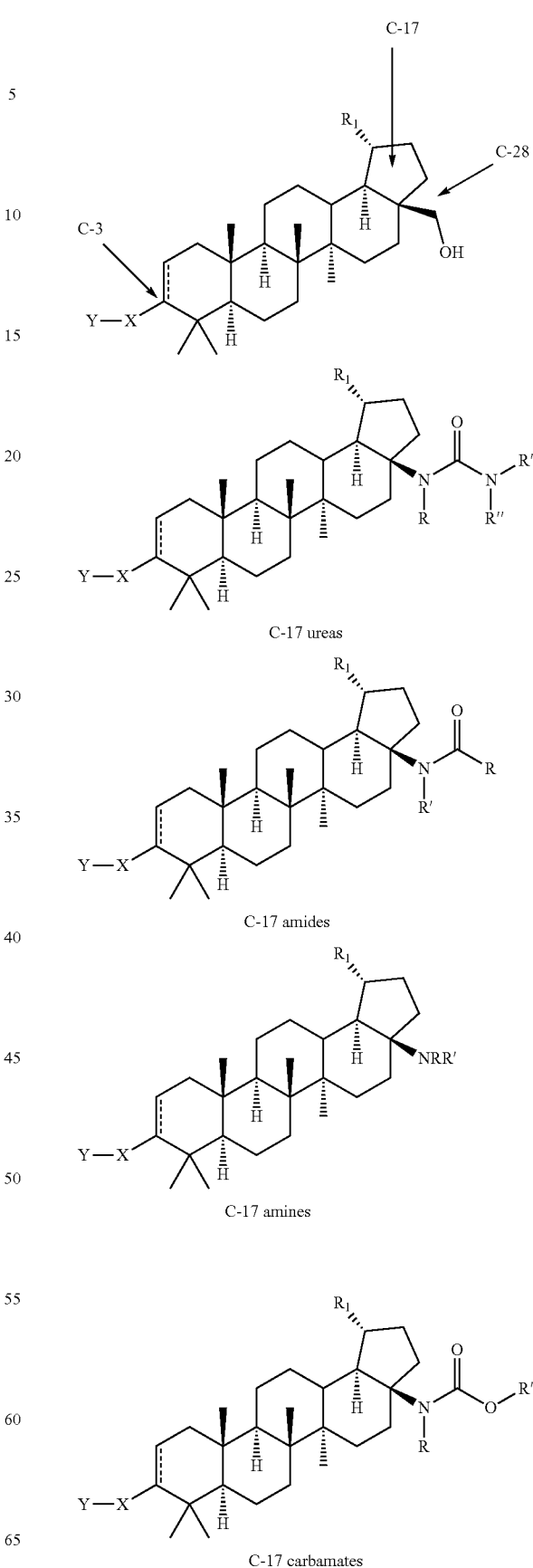

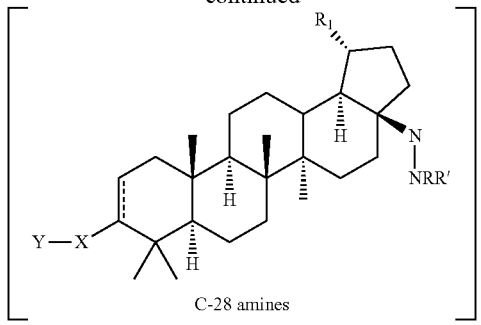

C-28 amines

EXAMPLES

The following examples illustrate typical syntheses of the compounds of Formulas ninety I and II as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B, or Varian Gemini 300 at 300 MHz as stated). The chemical shifts were reported in ppm on the δ scale relative to δTMS=0. The following internal references were used for the residual protons in the following solvents: CDCl$_3$ ($\delta_H$ 7.26), CD$_3$OD ($\delta_H$ 3.30), acetic-d4 (Acetic Acid d$_4$) ($\delta_H$ 11.6, 2.07), DMSO mix or DMSO-D6-CDCl$_3$ (δH 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS Methods:

Method 1

Start % B=0, Final % B=100 over 2 minute gradient, hold at 100% B

Flow Rate=1 mL/min

Wavelength=220 nm

Solvent A=90% water, 10% acetonitrile, 0.1% TFA

Solvent B=10% water, 90% acetonitrile, 0.1% TFA

Column=Phenomenex Luna C18, 3 μm, 2.0×30 mm

Method 2

Start % B=0, Final % B=100 over 1 minute gradient, hold at 100% B

Flow Rate=1 mL/min

Wavelength=220 nm

Solvent A=90% water, 10% acetonitrile, 0.1% TFA

Solvent B=10% water, 90% acetonitrile, 0.1% TFA

Column=Phenomenex Luna C18, 3 μm, 2.0×30 mm

Method 3

Start % B=2, Final % B=98 over 1.5 minute gradient, hold at 98% B

Flow Rate=0.8 mL/min

Wavelength=220 nm

Solvent A=100% water, 0.05% TFA

Solvent B=100% acetonitrile, 0.05% TFA

Column=Waters Aquity UPLC BEH C18, 2.1×50 mm, 1.7 μm

Method 4

Start % B=20, Final % B=100 over 2 minute gradient, hold at 100% B

Flow Rate=0.8 mL/min

Wavelength=220 nm

Solvent A=90% water, 10% methanol, 0.1% TFA

Solvent B=10% water, 90% methanol, 0.1% TFA

Column=Waters Xbridge Phenyl, 2.5 μm, 2.1×50 mm

Method 5

Start % B=0, Final % B=100 over 2 minute gradient, hold at 100% B

Flow Rate=1 mL/min

Wavelength=220 nm

Solvent A=90% water, 10% methanol, 0.1% TFA

Solvent B=10% water, 90% methanol, 0.1% TFA

Column=Phenomenex Luna C18, 3 μm, 2.0×30 mm

Prep HPLC Methods:

Method 1

Start % B=25 Final % B=100 over 15 minute gradient, hold at 100% B

Flow Rate=40 mL/min

Solvent A=10% ACN–90% H$_2$O–0.1% TFA

Solvent B=90% ACN–10% H$_2$O–0.1% TFA

Column=Waters Sunfire 30×100 mm 5 μm

Method 2

Start % B=25 Final % B=100 over 20 minute gradient, hold at 100% B

Flow Rate=40 mL/min

Solvent A=10% ACN–90% H$_2$O–0.1% TFA

Solvent B=90% ACN–10% H$_2$O–0.1% TFA

Column=Waters Sunfire 30×100 mm 5 μm

SFC Method

First Pass

| | |
|---|---|
| Preparative Column: | Whelko-RR (5'50 cm, 10 μm, #786710) |
| BPR pressure: | 100 bars |
| Temperature: | 30° C. |
| Flow rate: | 350 mL/min |
| Mobile Phase: | CO$_2$/2-propanol (85/15) |
| Detector Wavelength: | 215 nm |
| Separation Program:: | stack injection |
| Injection: | 1.46 mL with cycle time: 1.9 mins |
| Sample preparation: | 180 g/1000 mL IPA:DCM (1:1), 180 mg/mL |
| Throughput: | 7.88 g/hr |

Example 1
Preparation of 4-((3aR,5aR,5bR,7aR,11aS,11bR,13aS)-1-isopropyl-5a,5b,8,8,11a-pentamethyl-3a-((2-morpholinoethyl)carbamoyl)-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylic acid
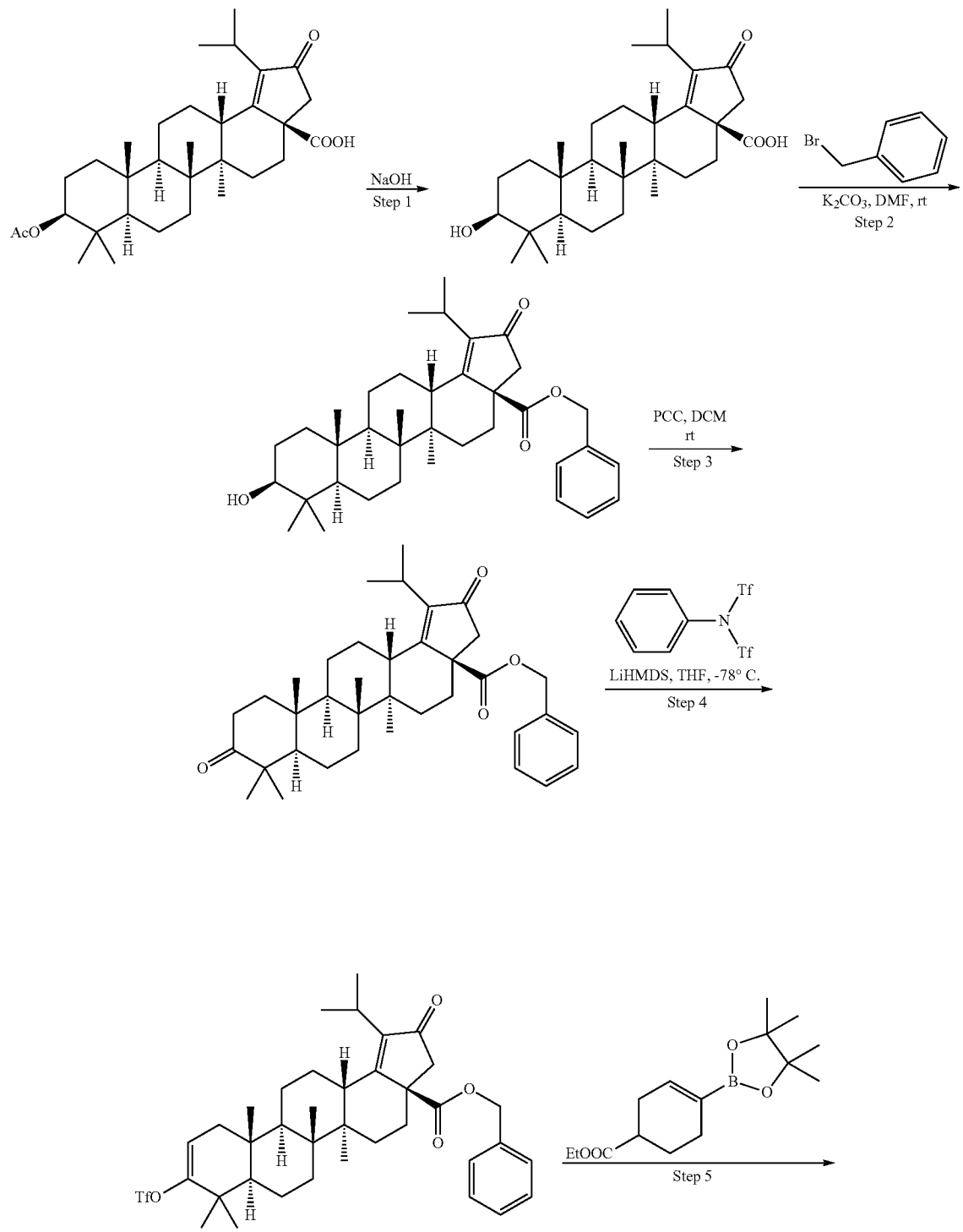

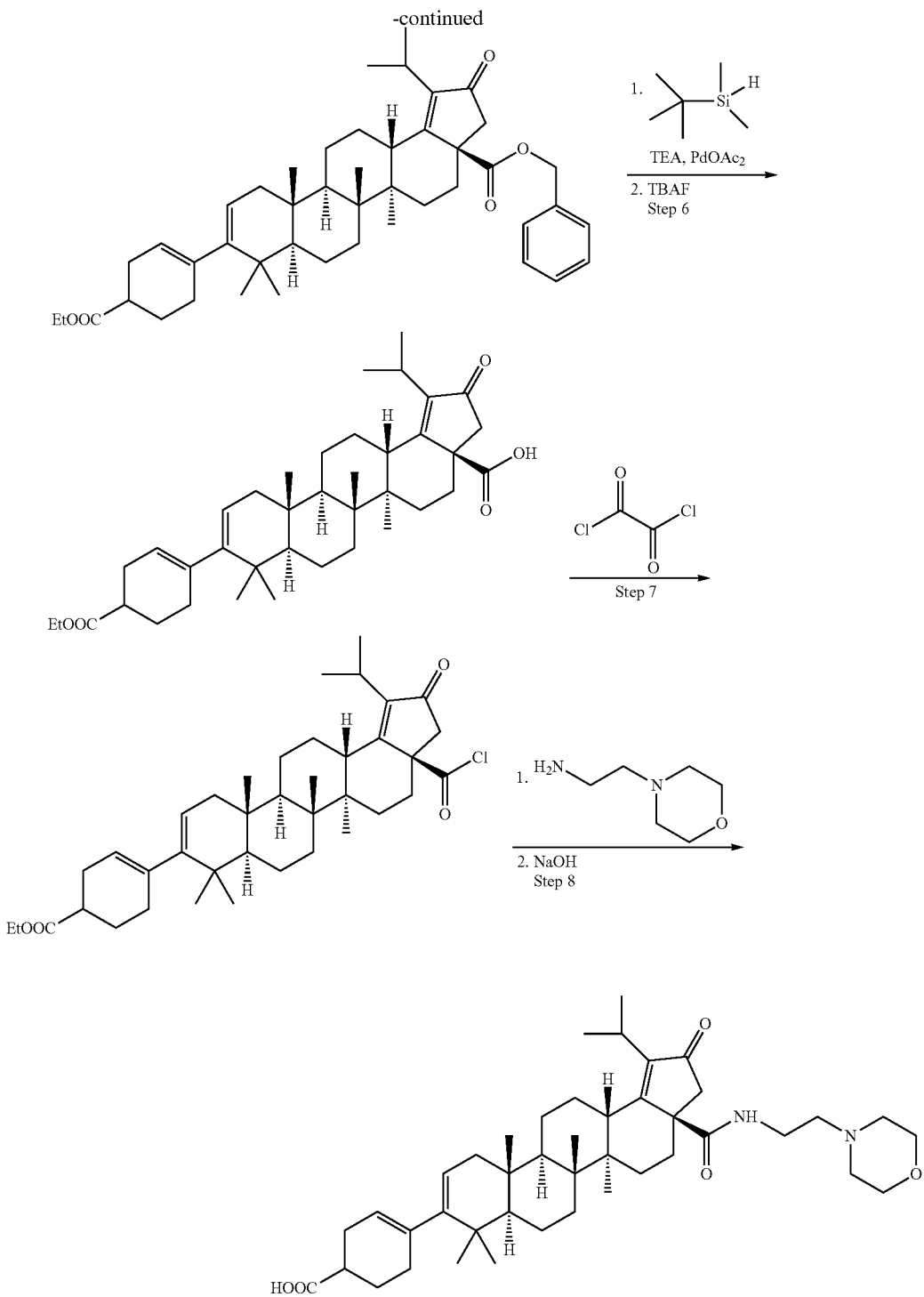

Example 1

Step 1. Preparation of (3aR,5aR,5bR,7aR,9S,11aR, 11bR,13aS)-9-hydroxy-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a] chrysene-3a-carboxylic acid A mixture of (3aR,5aR,5bR,7aR,9S,11aR,11bR,13aS)-9-acetoxy-1-isopropyl-5a,5b,8,8,11a-pentamethyl-2-oxo-3,3a, 4,5,5a,5b,6,7,7a,8,9,10,11,11a,11b,12,13,13a-octadeca- hydro-2H-cyclopenta[a]chrysene-3a-carboxylic acid (2 g, 3.90 mmol) and sodium hydroxide (1.560 g, 39.0 mmol) in THF (20 mL), methanol (10 mL) and water (10 mL) was stirred at rt for 48 hours. The reaction mixture was neutralized with 5N HCl and extracted with ethyl acetate (3×15 mL). The combined organic phases were dried over sodium sulfate, filtered and concentrated under reduced pressure to provide the title compound as a pale yellow solid. (1.92 g, 100%). LCMS: m/e 471.4 (M+H)⁻, 1.90 min (method 1).

Step 2. Preparation of (3aR,5aR,5bR,7aR,9S,11aR, 11bR,13aS)-benzyl 9-hydroxy-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysene-3a-carboxylate A mixture of (3aR,5aR,5bR,7aR,9S,11aR,11bR,13aS)-9-hydroxy-1-isopropyl-5a,5b,8,8,11a-pentamethyl-2-oxo-3, 3a,4,5,5a,5b,6,7,7a,8,9,10,11,11a,11b,12,13,13a-octadecahydro-2H-cyclopenta[a]chrysene-3a-carboxylic acid (1.92 g, 4.08 mmol), (bromomethyl)benzene (0.533 mL, 4.49 mmol) and potassium carbonate (1.240 g, 8.97 mmol) in DMF (10 mL) was stirred at rt for 14 hours. The reaction mixture was quenched with water (20 mL). The solid formed was collected and dried under reduced pressure to provide the title compound as a white solid (2.2 g, 96%). LCMS: m/e 561.4 (M+H)⁻, 2.44 min (method 1).

Step 3. Preparation of (3aR,5aR,5bR,7aR,11aR, 11bR,13aS)-benzyl 1-isopropyl-5a,5b,8,8,11a-pentamethyl-2,9-dioxo-3,3a,4,5,5a,5b,6,7,7a,8,9,10,11, 11a,11b,12,13,13a-octadecahydro-2H-cyclopenta[a]chrysene-3a-carboxylate A mixture of (3aR,5aR,5bR,7aR,9S,11aR,11bR,13aS)-benzyl 9-hydroxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysene-3a-carboxylate (2.2 g, 3.92 mmol) and pyridinium chlorochromate (1.27 g, 5.88 mmol) in THF (10 mL) was stirred at rt for 4 hours. The reaction mixture was concentrated under reduced pressure and the residue was purified by flash chromatography using 0-20% ethyl acetate/hexanes to provide the title compound as a white solid. (1.92 g, 88%). LCMS: m/e 559.35 (M+H)⁺, 2.49 min (method 1).

Step 4. Preparation of (3aR,5aR,5bR,7aR,11aR, 11bR,13aS)-benzyl 1-isopropyl-5a,5b,8,8,11a-pentamethyl-2-oxo-9-(((trifluoromethyl)sulfonyl)oxy)-3, 3a,4,5,5a,5b,6,7,7a,8,11,11a,11b,12,13,13a-hexadecahydro-2H-cyclopenta[a]chrysene-3a-carboxylate To a solution of (3aR,5aR,5bR,7aR,11aR,11bR,13aS)-benzyl 1-isopropyl-5a,5b,8,8,11a-pentamethyl-2,9-dioxo-3, 3a,4,5,5a,5b,6,7,7a,8,9,10,11,11a,11b,12,13,13a-octadecahydro-2H-cyclopenta[a]chrysene-3a-carboxylate (200 mg, 0.358 mmol) and 1,1,1-trifluoro-N-phenyl-N-((trifluoromethyl)sulfonyl)methanesulfonamide (192 mg, 0.537 mmol) in THF (5 mL) at −78° C. was added lithium bis(trimethylsilyl)amide (0.859 mL, 0.859 mmol). The reaction mixture was stirred at −78° C. for 6 hours. The reaction mixture was quenched with distilled water (8 mL) and extracted with ethyl acetate (3×6 mL). The combined organic layers were dried over sodium sulfate, filtered and concentrated under reduced pressure. The crude obtained was purified by column chromatography using 0-21% ethyl acetate/hexanes to provide the title compound as a pale yellow solid. (200 mg, 81%). ¹H NMR (500 MHz, CHLOROFORM-d) δ7.52-7.31 (m, 5H), 5.60 (dd, J=6.8, 1.9 Hz, 1H), 5.32 (d, J=12 Hz, 1H), 5.01 (d, J=12.1 Hz, 1H), 3.19 (dt, J=14.0, 7.0 Hz, 1H), 2.61-2.47 (m, 2H), 2.43 (dd, J=12.1, 3.8 Hz, 1H), 2.24 (dd, J=16.9, 6.9 Hz, 1H), 2.15 (d, J=18.6 Hz, 1H), 1.99-1.70 (m, 4H), 1.54-1.23 (m, 15H), 1.18-1.12 (m, 1H), 1.14 (s, 3H), 1.04 (s, 3H), 0.95 (s, 3H), 0.92 (s, 3H), 0.78 (s, 3H).

Step 5. Preparation of (3aR,5aR,5bR,7aR,11aS, 11bR,13aS)-benzyl 9-(4-(ethoxycarbonyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysene-3a-carboxylate A mixture of (3aR,5aR,5bR,7aR,11aR,11bR,13aS)-benzyl 1-isopropyl-5a,5b,8,8,11a-pentamethyl-2-oxo-9-(((trifluoromethyl)sulfonyl)oxy)-3,3a,4,5,5a,5b,6,7,7a,8,11,11a, 11b,12,13,13a-hexadecahydro-2H-cyclopenta[a]chrysene-3a-carboxylate (200 mg, 0.289 mmol), ethyl 4-(4,4,5,5-tetramethyl-1,3,2-dioxaborolan-2-yl)cyclohex-3-enecarboxylate (105 mg, 0.375 mmol), (prepared as described in WO 2013123019) sodium carbonate (153 mg, 1.447 mmol) and tetrakis(triphenylphosphine)palladium (16.73 mg, 0.014 mmol) in dioxane (3 mL) and water (1.5 mL) was heated at 80° C. for 2 hours. The reaction mixture was quenched with distilled water (4 mL) and extracted with ethyl acetate (2×4 mL). The combined organic phases were dried over sodium sulfate, filtered and concentrated under reduced pressure. The crude obtained was purified by column chromatography using 0-20% ethyl acetate/hexanes to provide the title compound as a pale yellow oil (156 mg, 78%). LCMS: m/e 695.4 (M+H)⁺, 3.82 min (method 1). ¹H NMR (500 MHz, CHLOROFORM-d) δ7.42-7.31 (m, 5H), 5.42-5.35 (m, 1H), 5.31 (d, J=12.1 Hz, 1H), 5.24-5.17 (m, 1H), 5.01 (d, J=12.1 Hz, 1H), 4.16 (q, J=7.1 Hz, 2H), 3.20 (dt, J=14.0, 7.1 Hz, 1H), 2.58-2.47 (m, 3H), 2.44 (dd, J=12.1, 3.7 Hz, 1H), 2.37-2.29 (m, 2H), 2.25-2.12 (m, 3H), 2.09-1.98 (m, 2H), 1.91-1.27 (m, 20H), 1.23 (t, J=6.7 Hz, 3H), 1.13-1.03 (m, 1H), 1.01-0.87 (m, 12H), 0.78 (s, 3H).

Step 6. Preparation of (3aR,5aR,5bR,7aR,11aS, 11bR,13aS)-9-(4-(ethoxycarbonyl)cyclohex-1-en-1-yl)-1-isopropyl-5a,5b,8,8,11a-pentamethyl-2-oxo-3, 3a,4,5,5a,5b,6,7,7a,8,11,11a,11b,12,13,13a-hexadecahydro-2H-cyclopenta[a]chrysene-3a-carboxylic acid A mixture of (3aR,5aR,5bR,7aR,11aS,11bR,13aS)-benzyl 9-(4-(ethoxycarbonyl)cyclohex-1-en-1-yl)-1-isopropyl-5a, 5b,8,8,11a-pentamethyl-2-oxo-3,3a,4,5,5a,5b,6,7,7a,8,11, 11a,11b,12,13,13a-hexadecahydro-2H-cyclopenta[a]chrysene-3a-carboxylate (150 mg, 0.216 mmol), tert-butyldimethylsilane (37.6 mg, 0.324 mmol), triethylamine (0.060 mL, 0.432 mmol) and palladium acetate (12.11 mg, 0.054 mmol) in dichloroethane (2 mL) was heated at 60° C. for 3 hours. To the mixture were added tert-butyldimethylsilane (37.6 mg, 0.324 mmol), triethylamine (0.060 mL, 0.432 mmol) and palladium acetate (12.11 mg, 0.054 mmol) again and the reaction mixture was heated at 60° C. for another 3 hours. The reaction mixture was concentrated under reduced pressure, the residue was dissolved in dichloromethane (2 mL) and filtered through a pad of celite. To the red filtrate was added tetra-N-butylammonium fluoride (527 mg, 1.511 mmol), the reaction mixture was stirred for 2 hours at room temperature. The reaction mixture was concentrated under reduced pressure. The residue obtained was purified by column chromatography using 0-10% MeOH/ethyl acetate to provide the desired product as a pale red oil. (100 mg, 77%). LCMS: m/e 605.4 (M+H)⁺, 2.74 min (method 1).

Step 7. Preparation of ethyl 4-((3aR,5aR,5bR,7aR, 11aS,11bR,13aS)-3a-(chlorocarbonyl)-1-isopropyl-5a,5b,8,8,11a-pentamethyl-2-oxo-3,3a,4,5,5a,5b,6,7, 7a,8,11,11a,11b,12,13,13a-hexadecahydro-2H-cyclopenta[a]chrysen-9-yl)cyclohex-3-enecarboxylate A mixture of (3aR,5aR,5bR,7aR,11aS,11bR,13aS)-9-(4-(ethoxycarbonyl)cyclohex-1-en-1-yl)-1-isopropyl-5a,5b,8, 8,11a-pentamethyl-2-oxo-3,3a,4,5,5a,5b,6,7,7a,8,11,11a, 11b,12,13,13a-hexadecahydro-2H-cyclopenta[a]chrysene-3a-carboxylic acid (70 mg, 0.116 mmol) and oxalyl dichloride (0.039 mL, 0.463 mmol) in dichloromethane (3 mL) was stirred at 20° C. for 3 hours. The reaction mixture was concentrated under reduced pressure to provide the title compound as a pale yellow oil. (60 mg, 83%) which was used in the next step without further purification. LCMS: m/e 619.4 (M-Cl+MeOH)$^+$, 2.41 min (method 2). LCMS sample was quenched with methanol.

Step 8. To a solution of 2-morpholinoethanamine (9.40 mg, 0.072 mmol), Hunig's Base (0.025 mL, 0.144 mmol) and 4-di(methylamino)pyridine (5.88 mg, 0.048 mmol) in dichloromethane (1 mL) was added a solution of ethyl 4-((3aR,5aR,5bR,7aR,11aS,11bR,13aS)-3a-(chlorocarbonyl)-1-isopropyl-5a,5b,8,8,11a-pentamethyl-2-oxo-3,3a,4,5, 5a,5b,6,7,7a,8,11,11a,11b,12,13,13a-hexadecahydro-2H-cyclopenta[a]chrysen-9-yl)cyclohex-3-enecarboxylate (30 mg, 0.048 mmol) in dichloromethane (0.5 mL). The reaction mixture was stirred at 20° C. for 1 hour. The reaction mixture was concentrated under reduced pressure and the crude material was purified by HPLC to provide methyl 4-((3aR,5aR,5bR,7aR,11aS,11bR,13aS)-1-isopropyl-5a,5b, 8,8,11a-pentamethyl-3a-((2-morpholinoethyl)carbamoyl)-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate. This ester intermediate was dissolved in dioxane (1 mL) and sodium hydroxide (0.481 mL, 0.481 mmol) was added. The reaction mixture was heated at 80° C. for 2 hours. The reaction mixture was filtered and purified by prep. HPLC to provide the title compound as colorless oil (5.8 mg, 17%). LCMS: m/e 689.4 (M+H)$^+$, 1.78 min (method 1). $^1$H NMR (500 MHz, METHANOL-d4) δ7.91 (t, J=5.6 Hz, 1H), 5.38 (br. s., 1H), 5.30-5.19 (m, 1H), 4.09 (br. s., 2H), 3.80 (br. s., 2H), 3.72-3.50 (m, 4H), 3.38-3.15 (m, 5H), 2.86 (dd, J=12.8, 3.0 Hz, 1H), 2.60-2.49 (m, 2H), 2.46 (d, J=18.9 Hz, 1H), 2.35-2.27 (m, 2H), 2.26-2.18 (m, 3H), 2.16-1.94 (m, 4H), 1.81 (td, J=13.8, 3.5 Hz, 1H), 1.76-1.63 (m, 3H), 1.62-1.43 (m, 6H), 1.41-1.30 (m, 2H), 1.27 (d, J=6.9 Hz, 3H), 1.22 (d, J=6.9 Hz, 3H), 1.19-1.14 (m, 1H), 1.12-1.08 (m, 3H), 1.05-0.93 (m, 12H).

Example 2

Preparation of 4-((3aR,5aR,5bR,7aR,11aS,11bR, 13aS)-3a((2-(1,1-dioxidothiomorpholino)ethyl)carbamoyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl) cyclohex-3-enecarboxylic acid

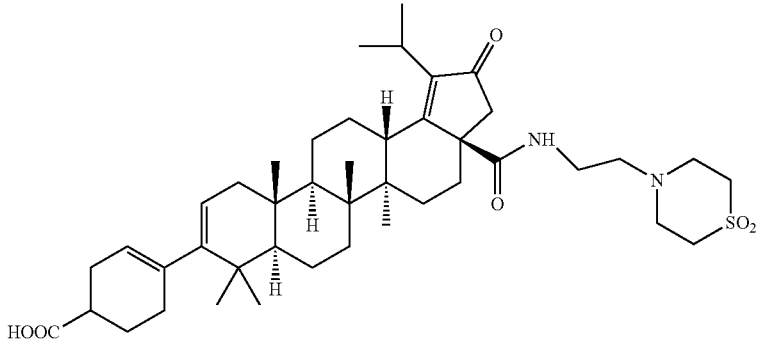

The title compound was prepared following the procedure described above for the preparation of 4-((3aR,5aR,5bR, 7aR,11aS,11bR,13aS)-1-isopropyl-5a,5b,8,8,11a-pentamethyl-3a-((2-morpholinoethyl)carbamoyl)-2-oxo-3,3a,4,5, 5a,5b,6,7,7a,8,11,11a,11b,12,13,13a-hexadecahydro-2H-cyclopenta[a]chrysen-9-yl)cyclohex-3-enecarboxylic acid, only 4-(2-aminoethyl)thiomorpholine 1, 1-dioxide was used instead of 4-di(methylamino)pyridine in step 8. The title compound was isolated as colorless oil (7 mg, 19%). LCMS: m/e 737.4 (M+H)$^+$, 1.86 min (method 1). $^1$H NMR (500 MHz, METHANOL-d4) δ7.71 (t, J=5.5 Hz, 1H), 5.38 (br. s., 1H), 5.30-5.20 (m, 1H), 3.67-3.57 (m, 4H), 3.56-3.49 (m, 2H), 3.45-3.37 (m, 4H), 3.33-3.26 (m, 1H), 3.14 (t, J=6.3 Hz, 2H), 2.88 (dd, J=12.7, 3.1 Hz, 1H), 2.60-2.49 (m, 2H), 2.44 (d, J=18.9 Hz, 1H), 2.36-2.27 (m, 2H), 2.26-2.18 (m, 3H), 2.16-1.94 (m, 4H), 1.82 (td, J=13.7, 3.6 Hz, 1H), 1.77-1.63 (m, 3H), 1.62-1.54 (m, 2H), 1.53-1.42 (m, 4H), 1.41-1.31 (m, 2H), 1.27 (d, J=6.9 Hz, 3H), 1.22 (d, J=6.9 Hz, 3H), 1.20-1.14 (m, 1H), 1.11 (s, 3H), 1.06-0.93 (m, 12H).

Example 3

Preparation of (3aR,5aR,5bR,7aR,11aS,11bR,13aS)-9-(4-carboxyphenyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysene-3a-carboxylic acid

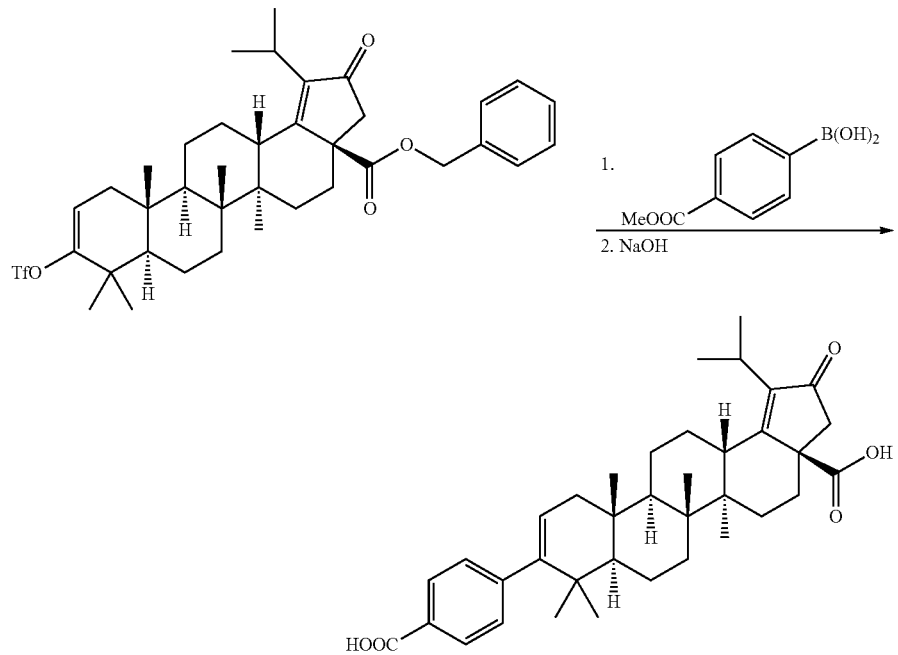

A mixture of (3aR,5aR,5bR,7aR,11aR,11bR,13aS)-benzyl 1-isopropyl-5a,5b,8,8,11a-pentamethyl-2-oxo-9-(((trifluoromethyl)sulfonyl)oxy)-3,3a,4,5,5a,5b,6,7,7a,8,11,11a,11b,12,13,13a-hexadecahydro-2H-cyclopenta[a]chrysene-3a-carboxylate (10 mg, 0.014 mmol), (4-(methoxycarbonyl)phenyl)boronic acid (3.39 mg, 0.019 mmol), tetrakis(triphenylphosphine)palladium (0.836 mg, 0.724 µmol) and sodium carbonate (1.534 mg, 0.014 mmol) in a mixture of dioxane (1 mL) and water (0.5 mL) was heated at 80° C. for 3 hours. The reaction mixture was quenched with distilled water (2 mL) and extracted with ethyl acetate (2×2 mL). The combined organic phases were dried over sodium sulfate, filtered and concentrated under reduced pressure to provide (3aR,5aR,5bR,7aR,11aS,11bR,13aS)-1-isopropyl-9-(4-(methoxycarbonyl)phenyl)-5a,5b,8,8,11a-pentamethyl-2-oxo-3,3a,4,5,5a,5b,6,7,7a,8,11,11a,11b,12,13,13a-hexadecahydro-2H-cyclopenta[a]chrysene-3a-carboxylic acid. This ester intermediate was dissolved in dioxane (1 mL) and 1N sodium hydroxide (0.145 mL, 0.145 mmol) was added. The reaction mixture was heated at 80° C. for 2 hours. The reaction mixture was filtered and purified by prep. HPLC to provide the title compound as a white solid (1.7 mg, 19%).

LCMS: m/e 573.5 (M+H)$^+$, 2.15 min (method 1). $^1$H NMR (500 MHz, CHLOROFORM-d) δ8.03 (d, J=8.2 Hz, 2H), 7.27 (d, J=8.2 Hz, 5H), 5.36 (d, J=5.0 Hz, 1H), 3.39-3.14 (m, 1H), 2.96-2.44 (m, 3H), 2.32-2.18 (m, 1H), 2.10 (d, J=6.0 Hz, 1H), 2.04-1.87 (m, 2H), 1.80 (d, J=16.9 Hz, 1H), 1.71-1.34 (m, 9H), 1.33-1.26 (m, 2H), 1.27 (s, 3H), 1.25 (s, 3H), 1.15 (s, 3H), 1.08 (s, 3H), 1.01 (s, 3H), 0.98 (s, 3H), 0.98 (s, 3H).

Example 4

Preparation of (3aR,5aR,5bR,7aR,11aS,11bR,13aS)-9-(4-carboxycyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysene-3a-carboxylic acid

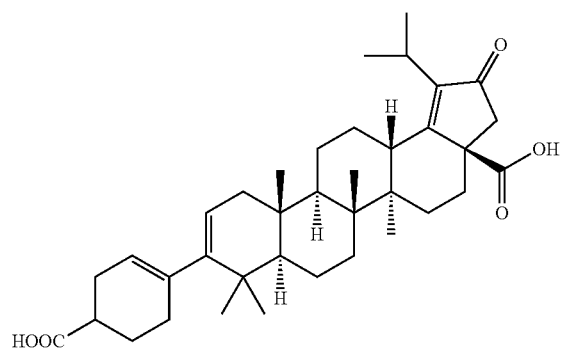

The title compound was prepared following the procedure described for the preparation of (3aR,5aR,5bR,7aR,11aS,11bR,13aS)-9-(4-carboxyphenyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysene-3a-carboxylic acid only 4-(ethoxycarbonyl)cyclohex-1-en-1-yl)

boronic acid was used instead of (4-(methoxycarbonyl)phenyl)boronic acid. The product was isolated as colorless oil (2 mg, 29%). LCMS: m/e 577.4 (M+H)+, 2.21 min (method 1). $^1$H NMR (500 MHz, METHANOL-d4) δ5.38 (s., 1H), 5.29-5.19 (m, 1H), 3.30-3.24 (m, 1H), 2.88 (dd, J=12.4, 3.5 Hz, 1H), 2.65-2.40 (m, 3H), 2.38-1.90 (m, 10H), 1.81-1.28 (m, 11H), 1.23 (s, 3H), 1.21 (s, 3H), 1.18-1.16 (m, 1H), 1.13 (s, 3H), 1.08-0.86 (m, 12H).

Example 5

Preparation of (3aR,5aR,5bR,7aR,11aS,11bR,13aS)-9-((S)-4-carboxy-4-(fluoromethyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysene-3a-carboxylic acid

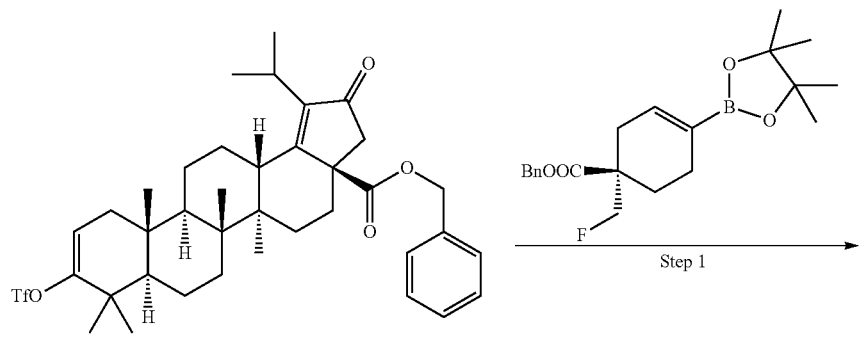

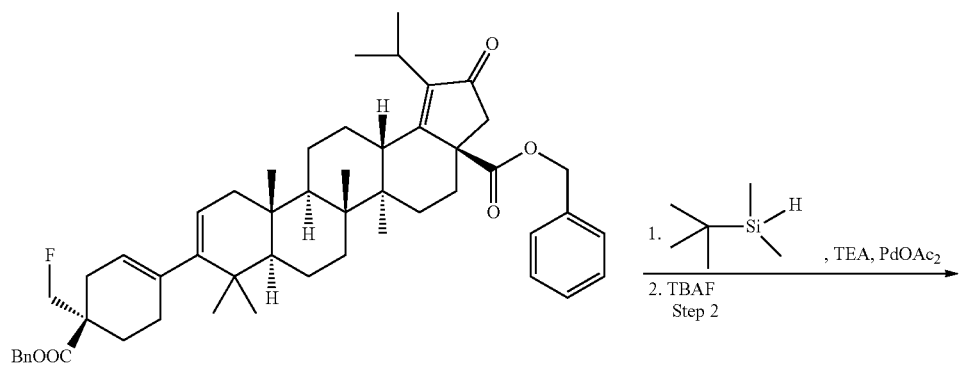

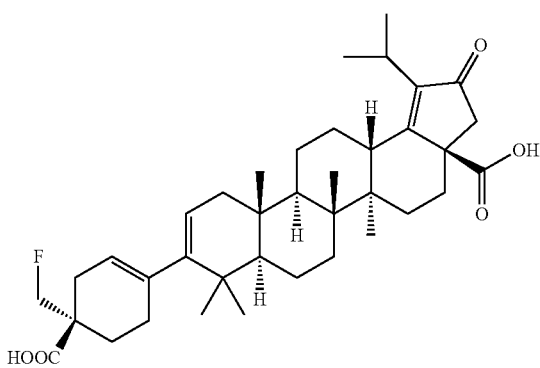

Example 5

Step 1. Preparation of (3aR,5aR,5bR,7aR,11aS, 11bR,13aS)-benzyl 9-((S)-4-((benzyloxy)carbonyl)-4-(fluoromethyl)cyclohex-1-en-1-yl)-1-isopropyl-5a, 5b,8,8,11a-pentamethyl-2-oxo-3,3a,4,5,5a,5b,6,7,7a, 8,11,11a,11b,12,13,13a-hexadecahydro-2H-cyclopenta[a]chrysene-3a-carboxylate A mixture of (3aR,5aR,5bR,7aR,11aR,11bR,13aS)-benzyl 1-isopropyl-5a,5b,8,8,11a-pentamethyl-2-oxo-9-(((trifluoromethyl)sulfonyl)oxy)-3,3a,4,5,5a,5b,6,7,7a,8,11,11a, 11b,12,13,13a-hexadecahydro-2H-cyclopenta[a]chrysene-3a-carboxylate (320 mg, 0.463 mmol), (S)-benzyl 1-(fluoromethyl)-4-(4,4,5,5-tetramethyl-1,3,2-dioxaborolan-2-yl)cyclohex-3-enecarboxylate (191 mg, 0.510 mmol), tetrakis(triphenylphosphine)palladium (26.8 mg, 0.023 mmol) and sodium carbonate (245 mg, 2.316 mmol) in a mixture of dioxane (3 mL) and water (1.500 mL) was heated at 80° C. for 2 hours. The reaction mixture was quenched with distilled water (6 mL) and extracted with ethyl acetate (2×6 mL). The combined organic phases were dried over sodium sulfate, filtered and concentrated under reduced pressure. The residue was purified by column chromatography with 0-20% ethyl acetate/hexanes to provide the title compound as a pale yellow oil (180 mg, 49%). LCMS: m/e 789.5 (M+H)$^+$, 2.73 min (method 2).

Step 2. A mixture of (3aR,5aR,5bR,7aR,11aS,11bR,13aS)-benzyl 9((S)-4-((benzyloxy)carbonyl)-4-(fluoromethyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysene-3a-carboxylate (180 mg, 0.228 mmol), tert-butyldimethylsilane (39.8 mg, 0.342 mmol), triethylamine (0.064 mL, 0.456 mmol) and palladium acetate (12.80 mg, 0.057 mmol) in dichloroethane (5 mL) was heated at 60° C. for 3 hours. The reaction mixture was filtered and the filtrates were concentrated under reduced pressure to provide corresponding silylester intermediate. The intermediate was dissolved in THF (5 mL) and tetra-N-butylammonium fluoride (557 mg, 1.597 mmol) was added. The reaction mixture was stirred for 2 hours and then concentrated under reduced pressure. The resulting crude was dissolved in methanol (5 mL) and purified by HPLC to provide the title compound as a white solid (62 mg, 42%). LCMS: m/e 609.3 (M+H)$^+$, 2.24 min (method 1). $^1$H NMR (500 MHz, CHLOROFORM-d) δ5.41 (s., 1H), 5.27 (d, J=4.9 Hz, 1H), 4.59 (s, 1H), 4.50 (s, 1H), 3.23 (dt, J=14.0, 7.0 Hz, 1H), 2.80 (dd, J=12.7, 2.8 Hz, 1H), 2.69-2.57 (m, 2H), 2.55-2.46 (m, 1H), 2.41-2.28 (m, 1H), 2.27-2.00 (m, 6H), 1.98-1.73 (m, 3H), 1.71-1.27 (m, 10H), 1.24 (s, 3H), 1.23 (s, 3H), 1.13-1.11 (m, 1H), 1.09 (s, 3H), 1.01 (s, 3H), 0.96 (s, 3H), 0.92 (s, 6H).

Example 6

Preparation of 4-((3aR,5aR,5bR,7aR,11aS,11bR, 13aS)-3a-((2-(1,1-dioxidothiomorpholino)ethyl) amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl) cyclohex-3-enecarboxylic acid

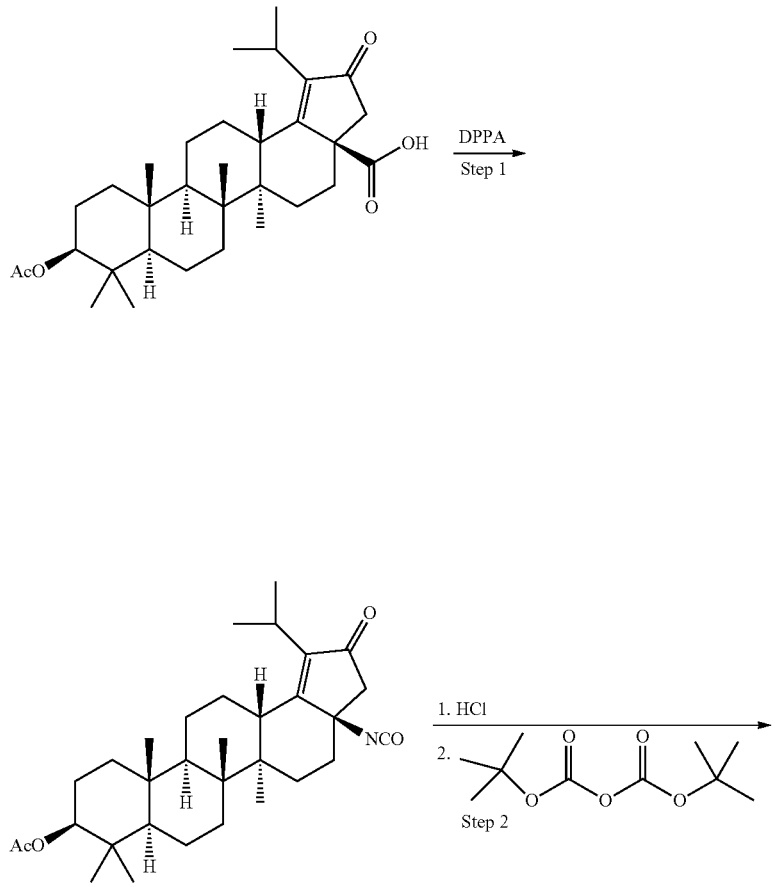

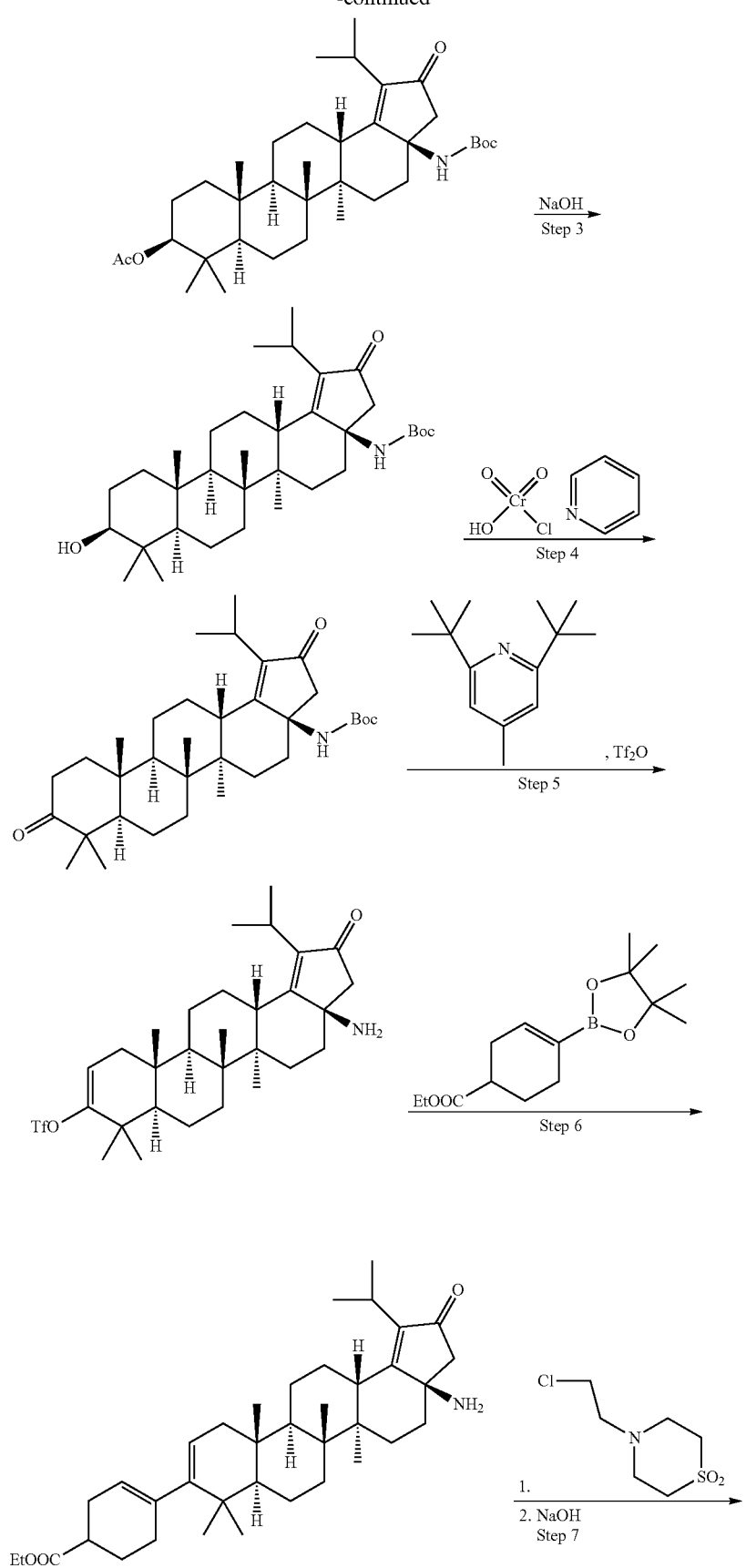

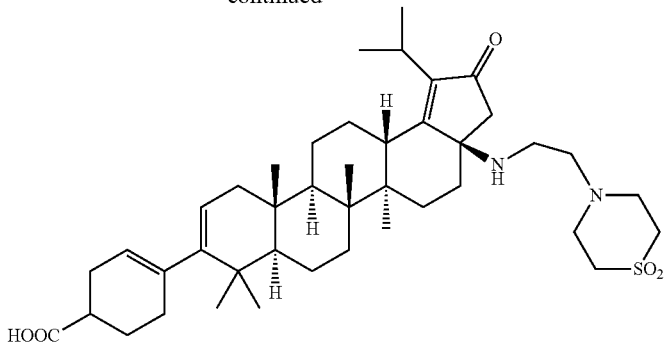

Example 6

Step 1. Preparation of (3aR,5aR,5bR,7aR,9S,11aR, 11bR,13aS)-3a-isocyanato-1-isopropyl-5a,5b,8,8, 11a-pentamethyl-2-oxo-3,3a,4,5,5a,5b,6,7,7a,8,9,10, 11,11a,11b,12,13,13a-octadecahydro-2H-cyclopenta [a]chrysen-9-yl acetate A mixture of (3aR,5aR,5bR,7aR,9S,11aR,11bR,13aS)-9-acetoxy-1-isopropyl-5a,5b,8,8,11a-pentamethyl-2-oxo-3,3a, 4,5,5a,5b,6,7,7a,8,9,10,11,11a,11b,12,13,13a-octadecahydro-2H-cyclopenta[a]chrysene-3a-carboxylic acid (500 mg, 0.975 mmol), diphenyl phosphorazidate (0.317 mL, 1.463 mmol) and triethylamine (0.272 mL, 1.950 mmol) in toluene (10 mL) was refluxed at 110° C. for 3 hours. The reaction mixture was concentrated under reduced pressure and the residue was purified by column chromatography using 0-16% ethyl acetate/hexanes to provide the title compound as a white solid (410 mg, 82%). LCMS: m/e 510.35 (M+H), 2.72 min (method 1).

Step 2. Preparation of (3aR,5aR,5bR,7aR,9S,11aR, 11bR,13aS)-3a-((tert-butoxycarbonyl)amino)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl acetate A mixture of (3aR,5aR,5bR,7aR,9S,11aR,11bR,13aS)-3a-isocyanato-1-isopropyl-5a,5b,8,8,11a-pentamethyl-2-oxo-3, 3a,4,5,5a,5b,6,7,7a,8,9,10,11,11a,11b,12,13,13a-octadecahydro-2H-cyclopenta[a]chrysen-9-yl acetate (410 mg, 0.804 mmol) and HCl (0.244 mL, 8.04 mmol) in THF (10 mL) was stirred at 20° C. for 18 hours. The reaction mixture was concentrated under reduced pressure. The residue was dissolved in THF (10 mL), triethylamine (0.336 mL, 2.413 mmol) and di-tert-butyl dicarbonate (0.374 mL, 1.609 mmol) were added. The reaction mixture was stirred for 20 hours at room temperature. The reaction mixture was quenched with distilled water (20 mL) and extracted with ethyl acetate (3×15 mL). The combined organic layers were dried over sodium sulfate, filtered and concentrated under reduced pressure to provide the title compound as a colorless oil (460 mg, 98%). LCMS: m/e 584.5 (M+H)$^+$, 2.59 min (method 1).

Step 3. Preparation of tert-butyl ((3aR,5aR,5bR, 7aR,9S,11aR,11bR,13aS)-9-hydroxy-1-isopropyl-5a, 5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-3a-yl)carbamate A mixture of (3aR,5aR,5bR,7aR,9S,11aR,11bR,13aS)-3a-((tert-butoxycarbonyl)amino)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl acetate (460 mg, 0.788 mmol) and sodium hydroxide (315 mg, 7.88 mmol) in THF (6 mL), methanol (2 mL) and water (5 mL) was stirred at rt for 18 hours. The reaction mixture was neutralized with 5N HCl and extracted with ethyl acetate (3×15 mL). The combined organic layers were dried over sodium sulfate, filtered and concentrated under reduced pressure to provide the title compound as a pale yellow solid (400 mg, 94%). LCMS: m/e 542.6 (M+H)$^+$, 2.33 min (method 1).

Step 4. Preparation of tert-butyl ((3aR,5aR,5bR, 7aR,11aR,11bR,13aS)-1-isopropyl-5a,5b,8,8,11a-pentamethyl-2,9-dioxo-3,3a,4,5,5a,5b,6,7,7a,8,9,10, 11,11a,11b,12,13,13a-octadecahydro-2H-cyclopenta [a]chrysen-3a-yl)carbamate A mixture of tert-butyl ((3aR,5aR,5bR,7aR,9S,11aR, 11bR,13aS)-9-hydroxy-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-3a-yl) carbamate (400 mg, 0.738 mmol) and pyridinium chlorochromate (239 mg, 1.107 mmol) in THF (5 mL) was stirred at rt for 15 hours. The reaction mixture was concentrated under reduced pressure. The residue was purified by column chromatography using 0-50% ethyl acetate/hexanes to provide the desired product as a white solid (220 mg, 55%). LCMS: m/e 540.5 (M+H)$^+$, 2.44 min (method 1).

Step 5. Preparation of (3aR,5aR,5bR,7aR,11aR, 11bR,13aS)-3a-amino-1-isopropyl-5a,5b,8,8,11a-pentamethyl-2-oxo-3,3a,4,5,5a,5b,6,7,7a,8,11,11a, 11b,12,13,13a-hexadecahydro-2H-cyclopenta[a] chrysen-9-yl trifluoromethanesulfonate To a solution of tert-butyl ((3aR,5aR,5bR,7aR,11aR, 11bR,13aS)-1-isopropyl-5a,5b,8,8,11a-pentamethyl-2,9-dioxo-3,3a,4,5,5a,5b,6,7,7a,8,9,10,11,11a,11b,12,13,13a-octadecahydro-2H-cyclopenta[a]chrysen-3a-yl)carbamate (70 mg, 0.13 mmol) in 1,2-dichloroethane (2 mL) was added 2,6-di-tert-butyl-4-methylpyridine (53.22 mg, 0.26 mmol) followed by trifluoromethanesulfonic anhydride (0.033 mL, 0.194 mmol) at 0° C. The reaction mixture was stirred for 1 hour at 0° C., 2 hours at room temperature and 2 hours at 73° C. The minute was cooled to room temperature and trifluoromethanesulfonic anhydride (0.016 mL, 0.093 mmol) was added. The reaction mixture was heated at 73° C. for another 4 hours and then cooled at room temperature. Trifluoromethanesulfonic anhydride (0.019 mL, 0.111 mmol) was added and the reaction mixture was heated at 73° C. for another 2 hours. The reaction mixture was quenched with sat. NaHCO₃ (3 mL) and extracted with dichloromethane (3×3 mL). The combined organic phase was dried over sodium sulfate, filtered and concentrated under reduced pressure. The crude was purified by column chromatography using 30-100% ethyl acetate/hexanes to provide the title compound as a yellow oil (20 mg, 27%). LCMS: m/e 555.4 (M-NH₂)⁻, 1.92 min (method 1).

Step 6. Preparation of ethyl 4-((3aR,5aR,5bR,7aR, 11aS,11bR,13aS)-3a-amino-1-isopropyl-5a,5b,8,8, 11a-pentamethyl-2-oxo-3,3a,4,5,5a,5b,6,7,7a,8,11, 11a,11b,12,13,13a-hexadecahydro-2H-cyclopenta[a] chrysen-9-yl)cyclohex-3-enecarboxylate A mixture of (3aR,5aR,5bR,7aR,11aR,11bR,13aS)-3a-amino-1-isopropyl-5a,5b,8,8,11a-pentamethyl-2-oxo-3,3a, 4,5,5a,5b,6,7,7a,8,11,11a,11b,12,13,13a-hexadecahydro-2H-cyclopenta[a]chrysen-9-yltrifluoromethanesulfonate (20 mg, 0.035 mmol), ethyl 4-(4,4,5,5-tetramethyl-1,3,2-dioxaborolan-2-yl)cyclohex-3-enecarboxylate (14.56 mg, 0.052 mmol) (prepared as describe in WO 2013123019), sodium carbonate (3.71 mg, 0.035 mmol) and tetrakis(triphenylphosphine)palladium (2.021 mg, 1.749 µmol) in dioxane (1 mL) and water (0.5 mL) was heated at 80° C. for 3 hours. The reaction mixture was quenched with distilled water (2 mL) and extracted with ethyl acetate (2×2 mL). The combined organic phases were dried over sodium sulfate, filtered and concentrated under reduced. The crude was dissolved in dioxane (1 mL), filtered and purified by prep. HPLC to provide the title compound as a white solid (9 mg, 45%). LCMS: m/e 559.4 (M-NH₂)⁺, 1.78 min (method 1).

Step 7. A mixture of ethyl 4-((3aR,5aR,5bR,7aR,11aS,11bR, 13aS)-3a-amino-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate (4 mg, 6.95 µmol), 4-(2-chloroethyl) thiomorpholine 1,1-dioxide (2.334 mg, 0.012 mmol), potassium iodide (1.153 mg, 6.95 µmol) and potassium phosphate (4.42 mg, 0.021 mmol) in acetonitrile (0.5 mL) was heated at 100° C. for 12 hours. The reaction mixture was quenched with distilled water (1 mL) and extracted with ethyl acetate (2×1 mL). The combined organic phases were dried over sodium sulfate, filtered and concentrated under reduced pressure. The crude was dissolved in dioxane (0.5 mL), then sodium hydroxide (0.069 mL, 0.069 mmol) was added. The reaction mixture was heated at 80° C. for 1 hour, filtered and purified by prep. HPLC to provide the title compound as a colorless oil (1.2 mg, 23%). LCMS: m/e 709.5 (M+H)⁺, 1.70 min (method 1). ¹H NMR (500 MHz, METHANOL-d4) δ 5.39 (s., 1H), 5.31-5.20 (m, 1H), 3.39-3.13 (m, 9H), 3.10-3.02 (m, 1H), 3.00-2.83 (m, 3H), 2.78 (dd, J=12.1, 3.6 Hz, 1H), 2.70-2.60 (m, 1H), 2.58-2.47 (m, 2H), 2.40-1.92 (m, 11H), 1.80-1.37 (m, 10H), 1.31-1.23 (m, 9H), 1.22-1.20 (m, 1H), 1.10-0.95 (m, 12H).

Example 7

Preparation of 4-((3aR,5aR,5bR,7aR,11aS,11bR, 13aS)-3a-amino-1-isopropyl-5a,5b,8,8,11a-pentamethyl-2-oxo-3,3a,4,5,5a,5b,6,7,7a,8,11,11a,11b,12, 13,13a-hexadecahydro-2H-cyclopenta[a]chrysen-9-yl)cyclohex-3-enecarboxylic acid

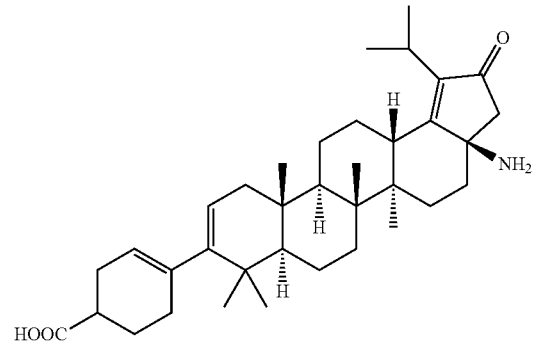

A mixture of ethyl 4-((3aR,5aR,5bR,7aR,11aS,11bR, 13aS)-3a-amino-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate (5 mg, 8.68 µmol) and sodium hydroxide (0.087 mL, 0.087 mmol) in dioxane (1 mL) was heated at 80° C. for 2 hours. The reaction was filtered and purified by prep. HPLC to provide the title compound as a colorless oil (2.3 mg, 45%). LCMS: m/e 548.4 (M+H)⁺, 1.56 min (method 1). ¹H NMR (500 MHz, METHANOL-d4) δ 5.39 (br. s., 1H), 5.26 (dt, J=6.2, 2.2 Hz, 1H), 3.37-3.33 (m, 1H), 2.89 (dd, J=12.5, 3.3 Hz, 1H), 2.66-2.46 (m, 3H), 2.38-2.06 (m, 7H), 2.05-1.83 (m, 4H), 1.80-1.66 (m, 3H), 1.62-1.61 (m, 2H), 1.57-1.37 (m, 5H), 1.31-1.22 (m, 9H), 1.20 (d, J=10.7 Hz, 1H), 1.10-0.94 (m, 12H).

Example 8
Preparation of (S)-4-((3aR,5aR,5bR,7aR,11aS,11bR, 13aS)-3a-amino-1-isopropyl-5a,5b,8,8,11a-pentamethyl-2-oxo-3,3a,4,5,5a,5b,6,7,7a,8,11,11a,11b,12, 13,13a-hexadecahydro-2H-cyclopenta[a]chrysen-9-yl)-1-(fluoromethyl)cyclohex-3-enecarboxylic acid
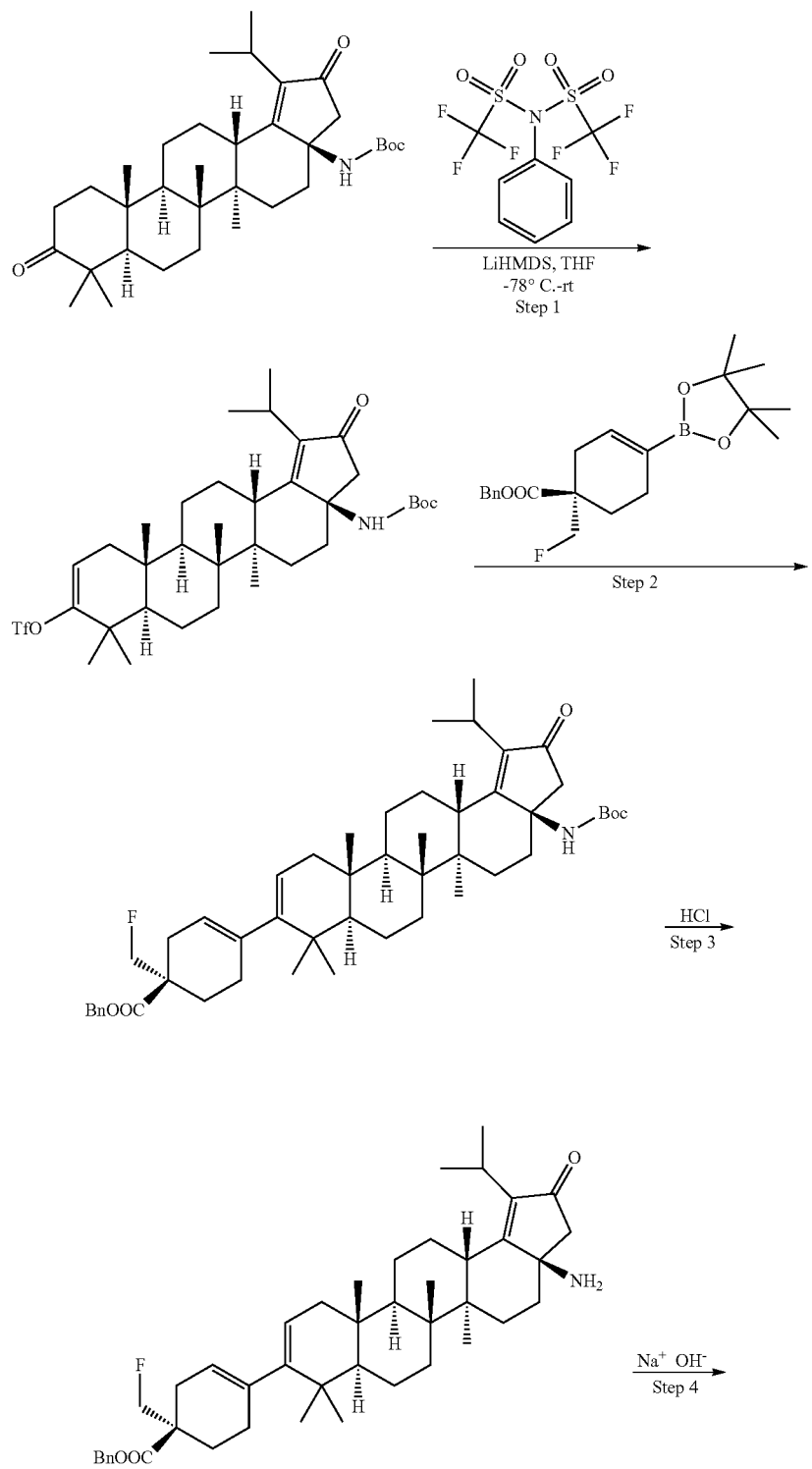

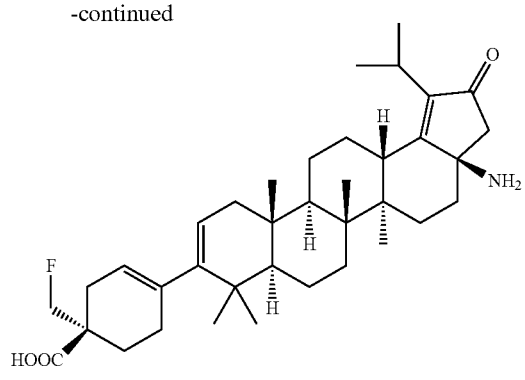

Example 8

Step 1. Preparation of (3aR,5aR,5bR,7aR,11aR, 11bR,13aS)-3a-((tert-butoxycarbonyl)amino)-1-isopropyl-5a,5b,8,8,11a-pentamethyl-2-oxo-3,3a,4,5,5a, 5b,6,7,7a,8,11,11a,11b,12,13,13a-hexadecahydro-2H-cyclopenta[a]chrysen-9-yltrifluoromethanesulfonate To a solution of tert-butyl ((3aR,5aR,5bR,7aR,11aR, 11bR,13aS)-1-isopropyl-5a,5b,8,8,11a-pentamethyl-2,9-dioxo-3,3a,4,5,5a,5b,6,7,7a,8,9,10,11,11a,11b,12,13,13a-octadecahydro-2H-cyclopenta[a]chrysen-3a-yl)carbamate (280 mg, 0.519 mmol) and 1,1,1-trifluoro-N-phenyl-N-((trifluoromethyl)sulfonyl)methanesulfonamide (241 mg, 0.674 mmol) in THF (5 mL) at −78° C. was added lithium bis(trimethylsilyl)amide (0.778 mL, 0.778 mmol). The reaction mixture was stirred at −78° C. for 18 hours. The reaction mixture was quenched with distilled water (20 mL), extracted with ethyl acetate (3×15 mL). The combined organic layers were dried over sodium sulfate, filtered and concentrated under reduced pressure. The resulting crude was purified using silica gel with 0-30% ethyl acetate/hexanes to provide the title compound as a colorless oil (250 mg, 58%). LCMS: m/e 672.4 (M+H)$^+$, 2.78 min (method 1).

Step 2. Preparation of (S)-benzyl 4-((3aR,5aR,5bR, 7aR,11aS,11bR,13aS)-3a-((tert-butoxycarbonyl) amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate A mixture of (3aR,5aR,5bR,7aR,11aR,11bR,13aS)-3a-((tert-butoxycarbonyl)amino)-1-isopropyl-5a,5b,8,8,11a-pentamethyl-2-oxo-3,3a,4,5,5a,5b,6,7,7a,8,11,11a,11b,12, 13,13a-hexadecahydro-2H-cyclopenta[a]chrysen-9-yltrifluoromethanesulfonate (250 mg, 0.372 mmol), (S)-benzyl 1-(fluoromethyl)-4-(4,4,5,5-tetramethyl-1,3,2-dioxaborolan-2-yl)cyclohex-3-enecarboxylate (153 mg, 0.409 mmol), tetrakis(triphenylphosphine)palladium (21.50 mg, 0.019 mmol) and sodium bicarbonate (197 mg, 1.861 mmol) in dioxane (3 mL) and water (1.5 mL) was heated up at 80° C. for 4 hours. The reaction mixture was quenched with distilled water (6 mL) and extracted with ethyl acetate (2×6 mL). The combined organic phases were dried over sodium sulfate, filtered and concentrated under reduced pressure. The crude obtained was purified using silica gel with 0-25% ethyl acetate/hexanes to provide the title compound as a pale yellow oil (253 mg, 88%). LCMS: m/e 770.6 (M+H)$^+$, 3.09 min (method 1).

Step 3. Preparation of (S)-benzyl 4-((3aR,5aR,5bR, 7aR,11aS,11bR,13aS)-3a-amino-1-isopropyl-5a,5b, 8,8,11a-pentamethyl-2-oxo-3,3a,4,5,5a,5b,6,7,7a,8, 11,11a,11b,12,13,13a-hexadecahydro-2H-cyclopenta [a]chrysen-9-yl)-1-(fluoromethyl)cyclohex-3-enecarboxylate A mixture of (S)-benzyl 4-((3aR,5aR,5bR,7aR,11aS, 11bR,13aS)-3a-((tert-butoxycarbonyl)amino)-1-isopropyl-5a,5b,8,8,11a-pentamethyl-2-oxo-3,3a,4,5,5a,5b,6,7,7a,8, 11,11a,11b,12,13,13a-hexadecahydro-2H-cyclopenta[a] chrysen-9-yl)-1-(fluoromethyl)cyclohex-3-enecarboxylate (250 mg, 0.325 mmol) and conc. HCl (0.141 mL, 1.623 mmol) in dioxane (3 mL) was stirred at 20° C. for 15 hours. The reaction mixture was concentrated under reduced pressure to provide the title compound as a pale yellow oil (160 mg, 74%). This material was used in the next step without further purification. LCMS: m/e 653.5 (M+H−17)$^+$, 2.14 min (method 1).

Step 4. A mixture of (S)-benzyl 4-((3aR,5aR,5bR,7aR,11aS, 11bR,13aS)-3a-amino-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate (9 mg, 0.013 mmol) and 1N sodium hydroxide (0.134 mL, 0.134 mmol) in dioxane (1 mL) was heated up at 80° C. for 2 hours. The reaction mixture was filtered and purified by prep HPLC with 0-70 HCN/water/TFA to provide (S)-4-((3aR,5aR,5bR, 7aR,11aS,11bR,13aS)-3a-amino-1-isopropyl-5a,5b,8,8,11a-pentamethyl-2-oxo-3,3a,4,5,5a,5b,6,7,7a,8,11,11a,11b,12, 13,13a-hexadecahydro-2H-cyclopenta[a]chrysen-9-yl)-1-(fluoromethyl)cyclohex-3-enecarboxylic acid as a colorless oil (4.2 mg, 51%). LCMS: m/e 563.5 (M+H−17)$^+$, 1.77 min (method 1). $^1$H NMR (500 MHz, ACETONITRILE-d3) δ5.36 (br. s., 1H), 5.24 (dd, J=6.3, 1.9 Hz, 1H), 4.65-4.53 (m, 1H), 4.53-4.43 (m, 1H), 3.29 (dt, J=14.0, 7.0 Hz, 1H), 2.84 (dd, J=12.1, 3.6 Hz, 1H), 2.62 (d, J=18.9 Hz, 1H), 2.54 (d, J=17.3 Hz, 1H), 2.44 (d, J=18.9 Hz, 1H), 2.32-1.29 (m, 20H), 1.23 (s, 3H), 1.20 (d, J=3.5 Hz, 3H), 1.19 (d, J=3.5 Hz, 3H), 1.16 (d, J=1.9 Hz, 1H), 0.99 (s, 6H), 0.97 (s, 3H), 0.96 (s, 3H).

Example 9 and Example 10

Preparation of (S)-4-((3aR,5aR,5bR,7aR,11aS,11bR,13aS)-3a-((2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylic acid and (S)-4-((3aR,5aR,5bR,7aR,11aS,11bR,13aS)-3a-(bis(2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylic acid

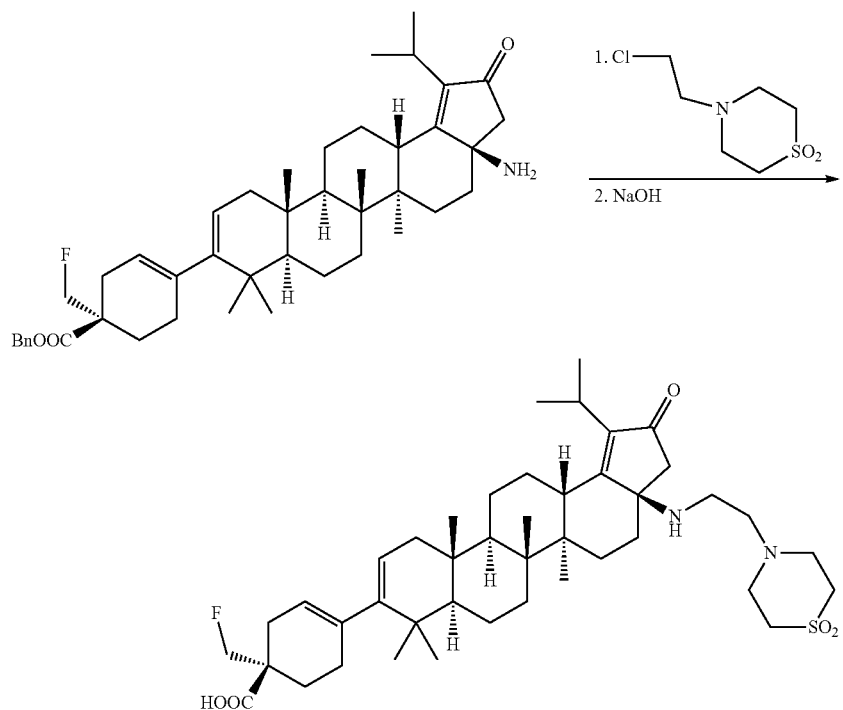

Example 9

+

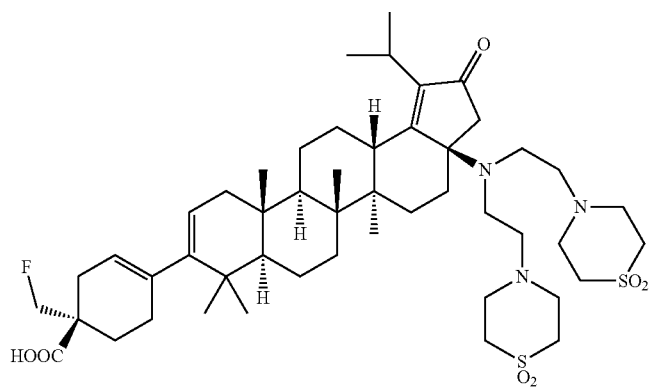

Example 10

A mixture of (S)-benzyl 4-((3aR,5aR,5bR,7aR,11aS,11bR,13aS)-3a-amino-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate (40 mg, 0.060 mmol), 4-(2-chloroethyl)thiomorpholine 1,1-dioxide (47.2 mg, 0.239 mmol), potassium iodide (14.87 mg, 0.090 mmol) and potassium phosphate (50.7 mg, 0.239 mmol) in acetonitrile (1 mL) was heated up at 100° C. for 3 days. The reaction mixture was quenched with distilled water (1 mL) and extracted with ethyl acetate (2×1 mL). The combined organic phases were dried over sodium sulfate, filtered and concentrated under reduced pressure. The resulting crude was dissolved in methanol (1 mL) and purified by prep. HPLC to provide two intermediates: (S)-benzyl 4-((3aR,5aR,5bR,7aR,11aS,11bR,13aS)-3a-((2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate as a colorless oil (8 mg, 16%). LCMS: m/e 831.6 (M+H)$^+$, 2.13 min (method 1) and (S)-benzyl 4-((3aR,5aR,5bR,7aR,11aS,11bR,13aS)-3a-(bis(2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate as colorless oil (15 mg, 25%). LCMS: m/e 992.6 (M+H)$^+$, 2.22 min (method 1). These two intermediates were treated with sodium hydroxide independently as follows:

A mixture of (S)-benzyl 4-((3aR,5aR,5bR,7aR,11aS,11bR,13aS)-3a-((2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate (8 mg, 9.62 µmol) and 1N sodium hydroxide (0.151 ml, 0.151 mmol) in acetonitrile (0.5 mL) and dioxane (0.5 mL) was heated up at 80° C. for 2 hours. The reaction mixture was filtered and purified by prep. HPLC to provide (S)-4-((3aR,5aR,5bR,7aR,11aS,11bR,13aS)-3a-((2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylic acid as a colorless oil (3 mg, 25%). LCMS: m/e 741.6 (M+H)$^+$, 1.73 min (method 1). $^1$H NMR (500 MHz, ACETONITRILE-d3) δ5.36 (br. s., 1H), 5.24 (dd, J=6.2, 1.7 Hz, 1H), 4.63-4.53 (m, 1H), 4.53-4.42 (m, 1H), 3.31 (quin, J=6.9 Hz, 1H), 3.17 (d, J=3.6 Hz, 4H), 3.09 (d, J=3.9 Hz, 4H), 3.03 (ddd, J=12.4, 6.5, 3.5 Hz, 1H), 2.99-2.85 (m, 2H), 2.85-2.78 (m, 1H), 2.77-2.72 (m, 1H), 2.69 (d, J=19.2 Hz, 1H), 2.54 (d, J=17.3 Hz, 1H), 2.41-2.32 (m, 2H), 2.29-1.42 (m, 19H), 1.24 (s, 3H), 1.22 (dd, J=6.9, 3.8 Hz, 6H), 1.19-1.15 (m, 1H), 1.00 (s, 3H), 0.99 (s, 6H), 0.97 (s, 3H).

(S)-benzyl 4-((3aR,5aR,5bR,7aR,11aS,11bR,13aS)-3a-(bis(2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate was treated with NaOH in the same manner described above to afford (S)-4-((3aR,5aR,5bR,7aR,11aS,11bR,13aS)-3a-(bis(2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylic acid as a colorless oil (8.1 mg, 56%). LCMS: m/e 902.7 (M+H)$^+$, 1.82 min (method 10). $^1$H NMR (500 MHz, ACETONITRILE-d3) δ5.36 (br. s., 1H), 5.24 (dd, J=6.1, 1.7 Hz, 1H), 4.73-4.27 (m, 2H), 3.89-3.58 (m, 8H), 3.56-3.40 (m, 8H), 3.38-3.05 (m, 6H), 2.98 (dd, J=13.2, 3.1 Hz, 2H), 2.79-2.61 (m, 2H), 2.54 (d, J=17.0 Hz, 1H), 2.33-1.85 (m, 11H), 1.80-1.65 (m, 2H), 1.62-1.36 (m, 8H), 1.27-1.05 (m, 11H), 1.03-0.85 (m, 12H).

Example 11 and example 12

Preparation of (S)-1-(fluoromethyl)-4-((3aR,5aR,5bR,7aR,11aS,11bR,13aS)-1-isopropyl-5a,5b,8,8,11a-pentamethyl-3a-((2-(4-(methylsulfonyl)piperidin-1-yl)ethyl)amino)-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylic acid and 1-(2-(((3aR,5aR,5bR,7aR,11aS,11bR,13aS)-9-((S)-4-carboxy-4-(fluoromethyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-3a-yl)amino)ethyl)-4-(methylsulfonyl)-1-(2-(4-(methylsulfonyl)piperidin-1-yl)ethyl)piperidin-1-ium

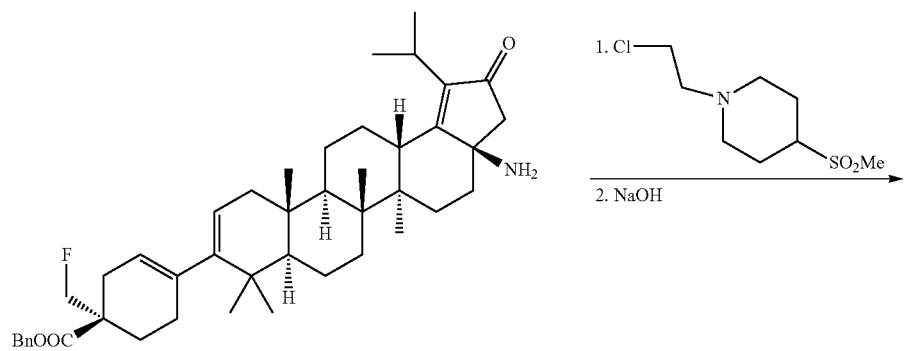

-continued

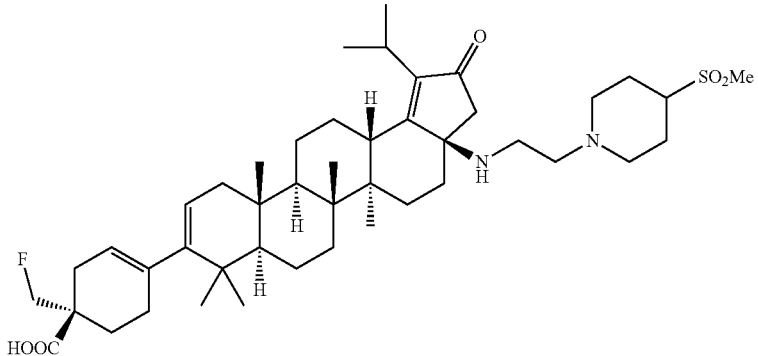

Example 11

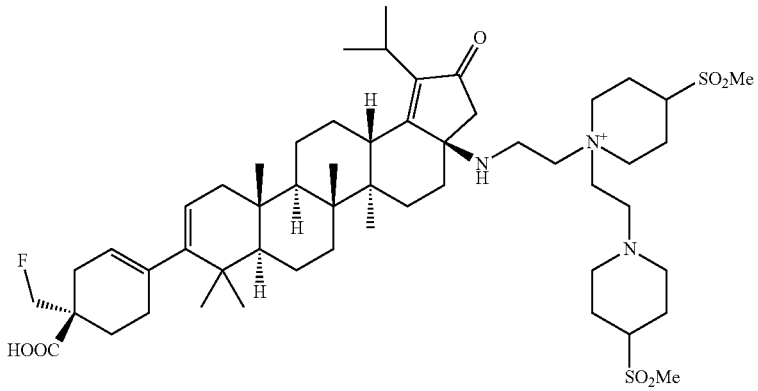

Example 12

A mixture of (S)-benzyl 4-((3aR,5aR,5bR,7aR,11aS,11bR,13aS)-3a-amino-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate (40 mg, 0.060 mmol), 1-(2-chloroethyl)-4-(methylsulfonyl)piperidine (53.9 mg, 0.239 mmol), potassium iodide (14.87 mg, 0.090 mmol) and potassium phosphate (50.7 mg, 0.239 mmol) in acetonitrile (1 mL) was heated up at 90° C. for 25 hours. The reaction mixture was quenched with distilled water (2 mL) and extracted with ethyl acetate (2×2 mL). The combined organic phases were dried over sodium sulfate, filtered and concentrated under reduced pressure. The resulting crude was dissolved in methanol (2 mL) and purified by prep. HPLC to provide two intermediates: (S)-benzyl 1-(fluoromethyl)-4-((3aR,5aR,5bR,7aR,11aS,11bR,13aS)-1-isopropyl-5a,5b,8,8,11a-pentamethyl-3a-((2-(4-(methylsulfonyl)piperidin-1-yl)ethyl)amino)-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate as a colorless oil. (12 mg, 24%). LCMS: m/e 859.6 (M+H)$^-$, 2.13 min (method 1) and 1-(2-(((3aR,5aR,5bR,7aR,11aS,11bR,13aS)-9-((S)-4-((benzyloxy)carbonyl)-4-(fluoromethyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-3a-yl)amino)ethyl)-4-(methylsulfonyl)-1-(2-(4-(methylsulfonyl)piperidin-1-yl)ethyl)piperidin-1-ium as colorless oil (13 mg, 21%). LCMS: m/e 1048.7 (M)$^+$, 1.49 min (method 3). These two intermediates were treated with sodium hydroxide independently as follows:

A mixture of (S)-benzyl 1-(fluoromethyl)-4-((3aR,5aR,5bR,7aR,11bR,13aS)-1-isopropyl-5a,5b,8,8,11a-pentamethyl-3a-((2-(4-(methylsulfonyl)piperidin-1-yl)ethyl)amino)-2-oxo-3,3a,4,5,5a,5b,6,7,7a,8,11,11a,11b,12,13,13a-hexadecahydro-2H-cyclopenta[a]chrysen-9-yl) cyclohex-3-enecarboxylate (12 mg, 0.014 mmol) and 1N sodium hydroxide (0.140 mL, 0.140 mmol) in acetonitrile (0.5 mL) and dioxane (0.5 mL) was heated up at 80° C. for 3 hours. The reaction mixture was filtered and purified by prep. HPLC to provide (S)-1-(fluoromethyl)-4-((3aR,5aR,5bR,7aR,11aS,11bR,13aS)-1-isopropyl-5a,5b,8,8,11a-pentamethyl-3a-((2-(4-(methylsulfonyl)piperidin-1-yl)ethyl)amino)-2-oxo-3,3a,4,5,5a,5b,6,7,7a,8,11,11a,11b,12,13,13a-hexadecahydro-2H-cyclopenta[a]chrysen-9-yl) cyclohex-3-enecarboxylic acid as a colorless oil (5 mg, 44%). LCMS: m/e 769.5 (M+H)+, 1.67 min (method 1). $^1$H NMR (500 MHz, ACETONITRILE-d3) δ5.36 (br. s., 1H), 5.24 (dd, J=6.1, 1.9 Hz, 1H), 4.66-4.42 (m, 2H), 3.74-3.58 (m, 2H), 3.57-3.47 (m, 1H), 3.46-3.38 (m, 1H), 3.33 (quin, J=6.9 Hz, 1H), 3.24 (tt, J=11.6, 3.9 Hz, 1H), 3.17-3.10 (m, 1H), 3.08-2.92 (m, 3H), 2.91 (s, 3H), 2.81 (dd, J=12.4, 3.4 Hz, 1H), 2.68 (d, J=19.2 Hz, 1H), 2.54 (d, J=16.9 Hz, 1H), 2.40-1.90 (m, 14H), 1.89-1.79 (m, 1H), 1.78-1.66 (m, 2H), 1.65-1.52 (m, 3H), 1.51-1.35 (m, 5H), 1.24 (s, 3H), 1.22 (dd, J=8.4, 7.0 Hz, 6H), 1.19-1.14 (m, 1H), 0.98 (s, 3H), 0.98 (s, 3H), 0.97 (s, 6H).

1-(2-(((3aR,5aR,5bR,7aR,11aS,11bR,13aS)-9-((S)-4-((benzyloxy)carbonyl)-4-(fluoromethyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-3a-yl)amino)ethyl)-4-(methylsulfonyl)-1-(2-(4-(methylsulfonyl)piperidin-1-yl)ethyl)piperidin-1-ium was treated with NaOH in the same manner described above to afford as a 1-(2-(((3aR,5aR,5bR, 7aR,11aS,11bR,13aS)-9-((S)-4-carboxy-4-(fluoromethyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-3a-yl)amino)ethyl)-4-(methylsulfonyl)-1-(2-(4-(methylsulfonyl)piperidin-1-yl)ethyl)piperidin-1-ium colorless oil (5.3 mg, 38%). LCMS: m/e 958.6 (M)$^+$, 1.68 min (method 1). $^1$H NMR (500 MHz, ACETONITRILE-d3) δ 5.36 (br. s., 1H), 5.28-5.16 (m, 1H), 4.67-4.39 (m, 2H), 3.79 (d, J=13.4 Hz, 2H), 3.63 (br. s., 2H), 3.51 (t, J=6.6 Hz, 2H), 3.43-3.17 (m, 6H), 3.15-2.99 (m, 4H), 2.97 (s, 3H), 2.93-2.90 (m, 1H), 2.88 (s, 3H), 2.73-1.29 (m, 34H), 1.25-1.15 (m, 10H), 0.99 (s, 3H), 0.98 (s, 3H), 0.97 (s, 3H), 0.97 (s, 3H).

Example 13

Preparation of (S)-4-((3aR,5aR,5bR,7aR,11aS,11bR,13aS)-3a-((3-(1,1-dioxidothiomorpholino)propyl)amino)methyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylic acid

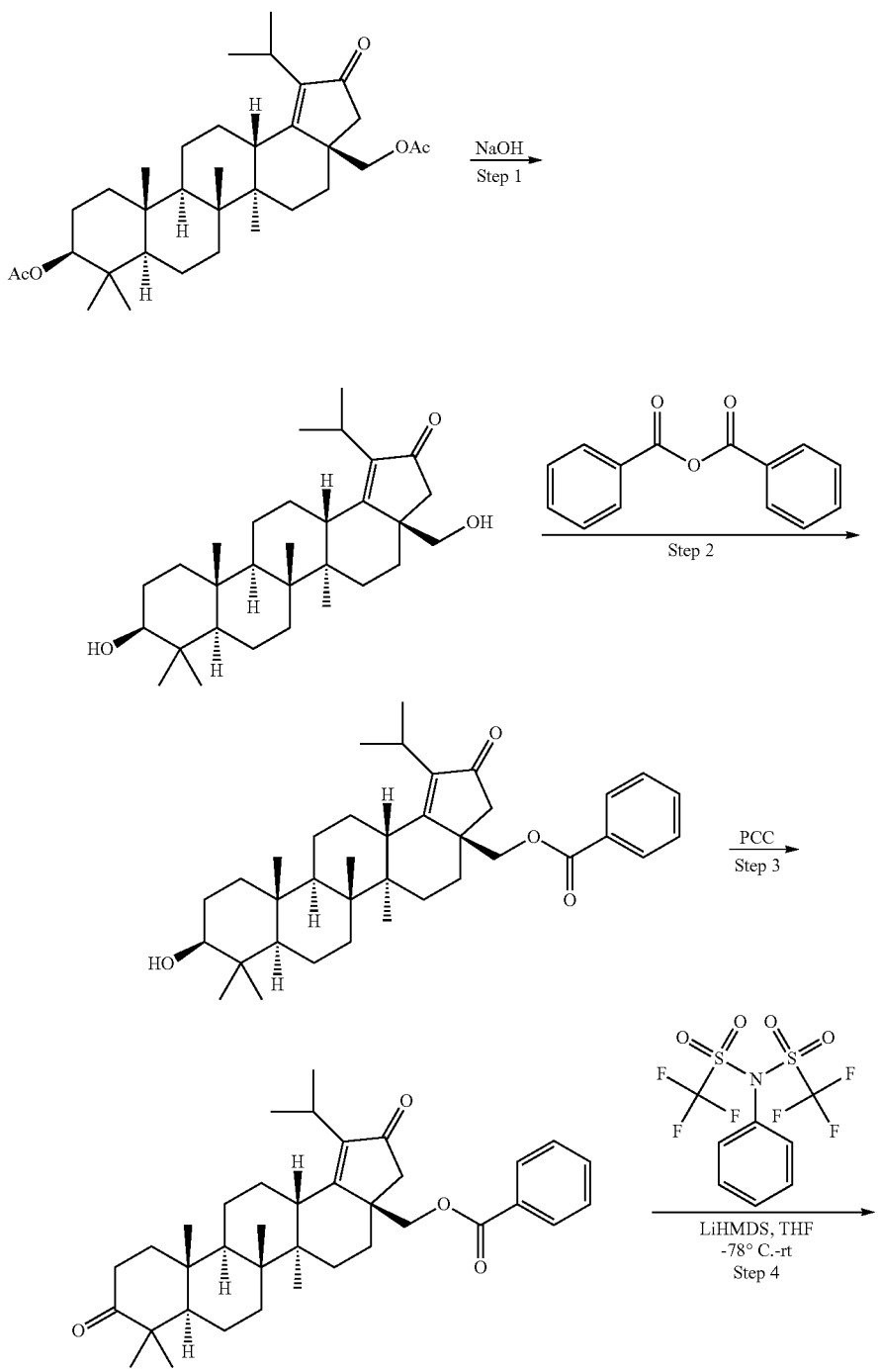

-continued
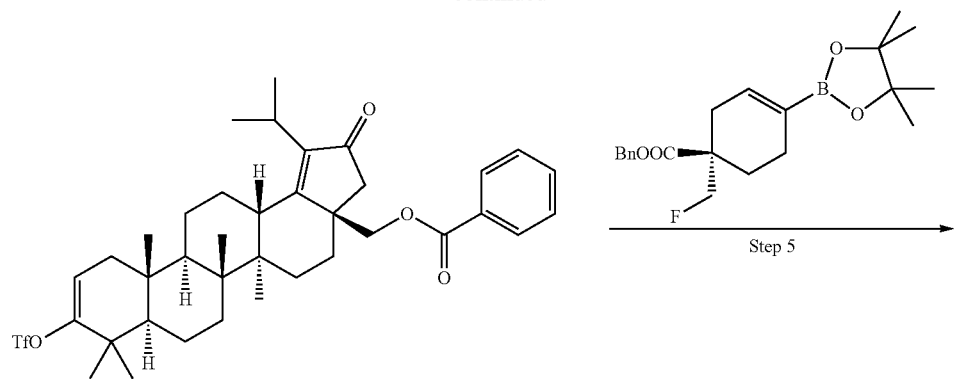
Step 5
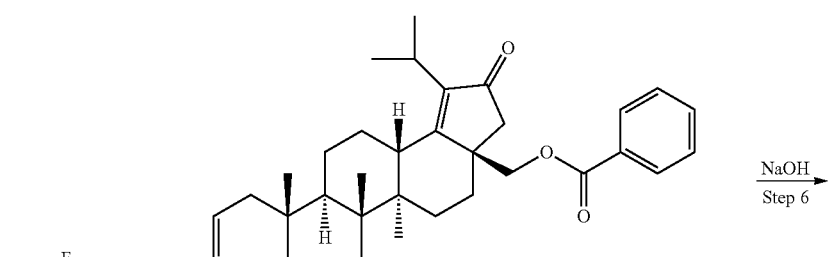
NaOH
Step 6
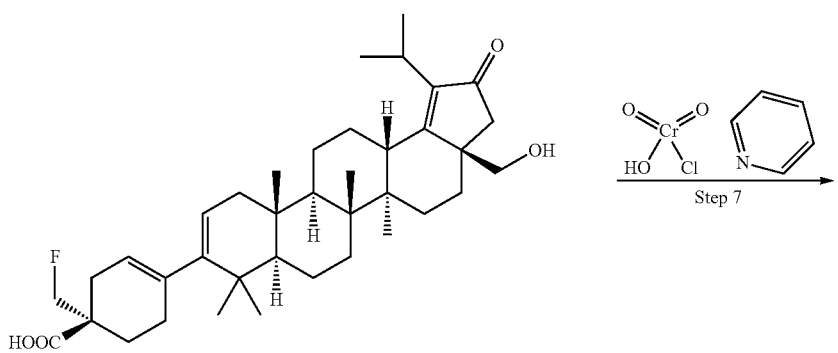
Step 7
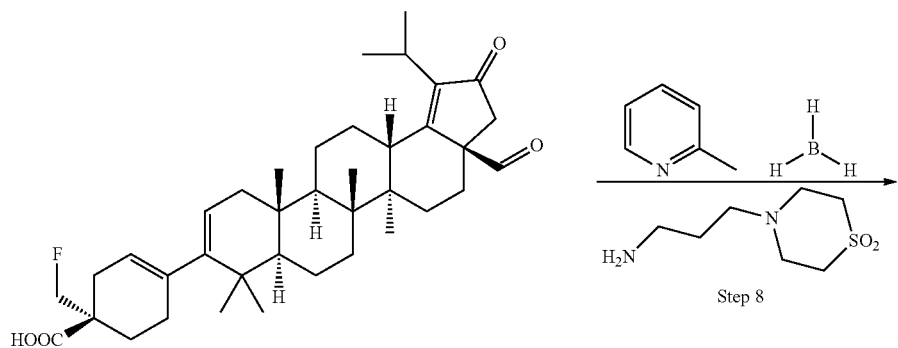
Step 8

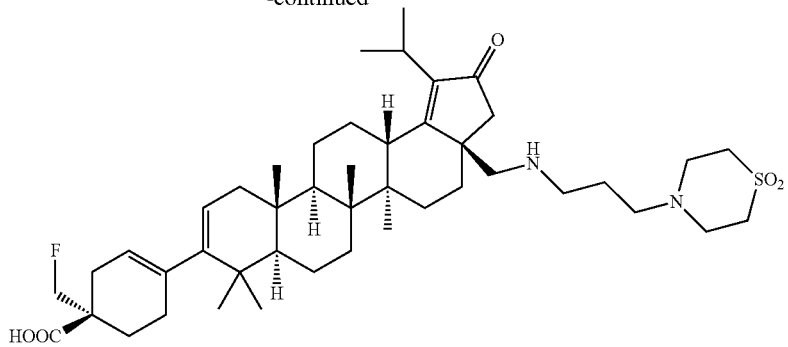

Example 13

Step 1. Preparation of (3aR,5aR,5bR,7aR,9S,11aR, 11bR,13aS)-9-hydroxy-3a-(hydroxymethyl)-1-isopropyl-5a,5b,8,8,11a-pentamethyl-3,3a,4,5,5a,5b,6,7, 7a,8,9,10,11,11a,11b,12,13,13a-octadecahydro-2H-cyclopenta[a]chrysen-2-one A mixture of ((3aR,5aR,5bR,7aR,9S,11aR,11bR,13aS)-9-acetoxy-1-isopropyl-5a,5b,8,8,11a-pentamethyl-2-oxo-3,3a, 4,5,5a,5b,6,7,7a,8,9,10,11,11a,11b,12,13,13a-octadecahydro-2H-cyclopenta[a]chrysen-3a-yl)methyl acetate (1.5 g, 2.77 mmol) and sodium hydroxide (1.109 g, 27.7 mmol) in THF (40 mL), water (10 mL) and MeOH (10 mL) was stirred at 20° C. for 18 hours. The reaction mixture was concentrated under reduced pressure and the residue was extracted with ethyl acetate (3×50 mL). The extracts were combined, washed with brine (50 mL), dried over sodium sulfate and concentrated under reduced pressure to provide the title compound as a white solid (1.28 g, 100%). LCMS: m/e 457.4 (M+H)$^+$, 1.94 min (method 1).

Step 2. Preparation of ((3aR,5aR,5bR,7aR,9 S,11aR,11bR,13aS)-9-hydroxy-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysen-3a-yl)methyl benzoate A mixture of (3aR,5aR,5bR,7aR,9S,11aR,11bR,13aS)-9-hydroxy-3a-(hydroxymethyl)-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-2-one (1.28 g, 2.80 mmol), benzoic anhydride (1.268 g, 5.61 mmol) and N,N-dimethylpyridin-4-amine (0.342 g, 2.80 mmol) in pyridine (20 mL) was stirred at 20° C. for 3 hours. The reaction mixture was concentrated under reduced pressure and the residue was purified using silica gel with 0-20% ethyl acetate/hexanes to provide the title compound as a white solid (1.3 g, 83%). LCMS: m/e 561.4 (M+H)$^+$, 2.46 min (method 1).

Step 3. Preparation of ((3aR,5aR,5bR,7aR,11aR, 11bR,13aS)-1-isopropyl-5a,5b,8,8,11a-pentamethyl-2,9-dioxo-3,3a,4,5,5a,5b,6,7,7a,8,9,10,11,11a,11b, 12,13,13a-octadecahydro-2H-cyclopenta[a]chrysen-3a-yl)methyl benzoate A mixture of ((3aR,5aR,5bR,7aR,9S,11aR,11bR,13aS)-9-hydroxy-1-isopropyl-5a,5b,8,8,11a-pentamethyl-2-oxo-3, 3a,4,5,5a,5b,6,7,7a,8,9,10,11,11a,11b,12,13,13a-octadecahydro-2H-cyclopenta[a]chrysen-3a-yl)methyl benzoate (1.3 g, 2.318 mmol) and pyridinium chlorochromate (1.0 g, 4.64 mmol) in THF (40 mL) was stirred at 20° C. for 15 hours. The reaction mixture was concentrated under reduced pressure and the residue was purified using silica gel with 0-40% ethyl acetate/hexanes to provide the title compound as a white solid. (1.1 g, 85%). LCMS: m/e 559.4 (M+H)$^+$, 2.55 min (method 1).

Step 4. Preparation of ((3aR,5aR,5bR,7aR,11aR, 11bR,13aS)-1-isopropyl-5a,5b,8,8,11a-pentamethyl-2-oxo-9-(((trifluoromethyl)sulfonyl)oxy)-3,3a,4,5, 5a,5b,6,7,7a,8,11,11a,11b,12,13,13a-hexadecahydro-2H-cyclopenta[a]chrysen-3a-yl)methyl benzoate To a solution of ((3aR,5aR,5bR,7aR,11aR,11bR,13aS)-1-isopropyl-5a,5b,8,8,11a-pentamethyl-2,9-dioxo-3,3a,4,5,5a, 5b,6,7,7a,8,9,10,11,11a,11b,12,13,13a-octadecahydro-2H-cyclopenta[a]chrysen-3a-yl)methyl benzoate (210 mg, 0.376 mmol) and 1,1,1-trifluoro-N-phenyl-N-((trifluoromethyl)sulfonyl)methanesulfonamide (161 mg, 0.451 mmol) in THF (5 mL) at −78° C. was added lithium bis(trimethylsilyl)amide (0.752 mL, 0.752 mmol). The reaction mixture was stirred at −78° C. for 18 hours. The reaction mixture was quenched with water (5 mL) and extracted with ethyl acetate (3×6 mL), the combined organic layer was dried over sodium sulfate, filtered and concentrated under reduced pressure. The resulting crude was purified using silica gel with 0-21% ethyl acetate/hexanes to provide the title compound as a white solid (150 mg, 58%). LCMS: m/e 691.4 (M+H)$^+$, 3.05 min (method 1).

Step 5. Preparation of ((3aR,5aR,5bR,7aR,11aS, 11bR,13aS)-9-((S)-4-((benzyloxy)carbonyl)-4-(fluoromethyl)cyclohex-1-en-1-yl)-1-isopropyl-5a,5b,8,8, 11a-pentamethyl-2-oxo-3,3a,4,5,5a,5b,6,7,7a,8,11, 11a,11b,12,13,13a-hexadecahydro-2H-cyclopenta[a] chrysen-3a-yl)methyl benzoate A mixture of (S)-benzyl 1-(fluoromethyl)-4-(4,4,5,5-tetramethyl-1,3,2-dioxaborolan-2-yl)cyclohex-3-enecarboxylate (89 mg, 0.239 mmol), ((3aR,5aR,5bR,7aR,11aR,11bR, 13aS)-1-isopropyl-5a,5b,8,8,11a-pentamethyl-2-oxo-9-(((trifluoromethyl)sulfonyl)oxy)-3,3a,4,5,5a,5b,6,7,7a,8,11, 11a,11b,12,13,13a-hexadecahydro-2H-cyclopenta[a] chrysen-3a-yl)methyl benzoate (150 mg, 0.217 mmol), tetrakis(triphenylphosphine)palladium (12.54 mg, 10.86 μmol) and sodium carbonate (69.0 mg, 0.651 mmol) in dioxane (3 mL) and water (1 mL) under nitrogen atmosphere was heated up at 80° C. for 4 hours. The reaction mixture was quenched with water (8 ml) and extracted with ethyl acetate (3×6 mL). The combined organic layer was dried over sodium sulfate, filtered and concentrated under reduced pressure to provide a crude. The crude was purified using silica gel with 0-27% ethyl acetate/hexanes to provide the title compound as a colorless oil (120 mg, 70%). LCMS: m/e 789.6 (M+H)⁺, 3.65 min (method 1).

Step 6. Preparation of (S)-1-(fluoromethyl)-4-((3aR, 5aR,5bR,7aR,11aS,11bR,13aS)-3a-(hydroxymethyl)-1-isopropyl-5a,5b,8,8,11a-pentamethyl-2-oxo-3,3a,4, 5,5a,5b,6,7,7a,8,11,11a,11b,12,13,13a-hexadecahydro-2H-cyclopenta[a]chrysen-9-yl) cyclohex-3-enecarboxylic acid A mixture of ((3aR,5aR,5bR,7aR,11aS,11bR,13aS)-9-((S)-4-((benzyloxy)carbonyl)-4-(fluoromethyl)cyclohex-1-en-1-yl)-1-isopropyl-5a,5b,8,8,11a-pentamethyl-2-oxo-3, 3a,4,5,5a,5b,6,7,7a,8,11,11a,11b,12,13,13a-hexadecahydro-2H-cyclopenta[a]chrysen-3a-yl)methyl benzoate (90 mg, 0.114 mmol) and 1N sodium hydroxide (0.684 mL, 0.684 mmol) in THF (2 mL) was stirred at 20° C. for 3 hours. The reaction mixture was quenched with distilled water (4 mL) and extracted with ethyl acetate (3×4 mL). The extracts were combined, dried over sodium sulfate, filtered and concentrated under reduced pressure to provide the title compound as a white solid (60 mg, 88%). LCMS: m/e 595.6 (M+H)⁺, 2.25 min (method 1).

Step 7. Preparation of (S)-1-(fluoromethyl)-4-((3aR, 5aR,5bR,7aR,11aS,11bR,13aS)-3a-formyl-1-isopropyl-5a,5b,8,8,11a-pentamethyl-2-oxo-3,3a,4,5,5a,5b, 6,7,7a,8,11,11a,11b,12,13,13a-hexadecahydro-2H-cyclopenta[a]chrysen-9-yl)cyclohex-3-enecarboxylic acid A mixture of (S)-1-(fluoromethyl)-4-((3aR,5aR,5bR,7aR, 11aS,11bR,13aS)-3a-(hydroxymethyl)-1-isopropyl-5a,5b,8, 8,11a-pentamethyl-2-oxo-3,3a,4,5,5a,5b,6,7,7a,8,11,11a, 11b,12,13,13a-hexadecahydro-2H-cyclopenta[a]chrysen-9-yl)cyclohex-3-enecarboxylic acid (35 mg, 0.059 mmol) and pyridinium chlorochromate (19.02 mg, 0.088 mmol) in dioxane (1 mL) was stirred at 20° C. for 3 hours. The reaction mixture was concentrated under reduced pressure and purified using silica gel with 0-40% ethyl acetate/hexanes to provide the title compound as a pale yellow oil (15 mg, 43%). LCMS: m/e 593.45 (M+H)⁺, 2.48 min (method 1).

Step 8. A mixture of (S)-1-(fluoromethyl)-4-((3aR,5aR,5bR, 7aR,11aS,11bR,13aS)-3a-formyl-1-isopropyl-5a,5b,8,8, 11a-pentamethyl-2-oxo-3,3a,4,5,5a,5b,6,7,7a,8,11,11a,11b, 12,13,13a-hexadecahydro-2H-cyclopenta[a]chrysen-9-yl) cyclohex-3-enecarboxylic acid (15 mg, 0.025 mmol), borane-2-methylpyridine complex (5.41 mg, 0.051 mmol) and 4-(3-aminopropyl)thiomorpholine 1,1-dioxide (7.30 mg, 0.038 mmol) in methanol (1 mL) was stirred at 20° C. for 3 hours. The reaction mixture was filtered and purified by HPLC with 0-70 actonitrile/water/TFA to provide (S)-4-((3aR,5aR,5bR,7aR,11aS,11bR,13aS)-3a-(((3-(1,1-dioxidothiomorpholino)propyl)amino)methyl)-1-isopropyl-5a,5b,8, 8,11a-pentamethyl-2-oxo-3,3a,4,5,5a,5b,6,7,7a,8,11,11a, 11b,12,13,13a-hexadecahydro-2H-cyclopenta[a]chrysen-9-yl)-1-(fluoromethyl)cyclohex-3-enecarboxylic acid as a colorless oil (4 mg, 20%). LCMS: m/e 769.7 (M+H)⁺, 1.74 min (method 1). ¹H NMR (500 MHz, ACETONITRILE-d3) δ5.36 (br. s., 1H), 5.24 (dd, J=6.1, 1.7 Hz, 1H), 4.70-4.39 (m, 2H), 3.61-3.47 (m, 4H), 3.38 (d, J=4.9 Hz, 4H), 3.32-3.12 (m, 5H), 3.08 (t, J=6.8 Hz, 2H), 2.85 (dd, J=12.4, 2.9 Hz, 1H), 2.54 (d, J=17.2 Hz, 1H), 2.43 (d, J=19.2 Hz, 1H), 2.31-1.25 (m, 23H), 1.24-1.14 (m, 10H), 0.98 (s, 3H), 0.97 (s, 3H), 0.97 (s, 6H).

Preparation of ethyl 1-(fluoromethyl)-4-(4,4,5,5-tetramethyl-1,3,2-dioxaborolan-2-yl)cyclohex-3-enecarboxylate

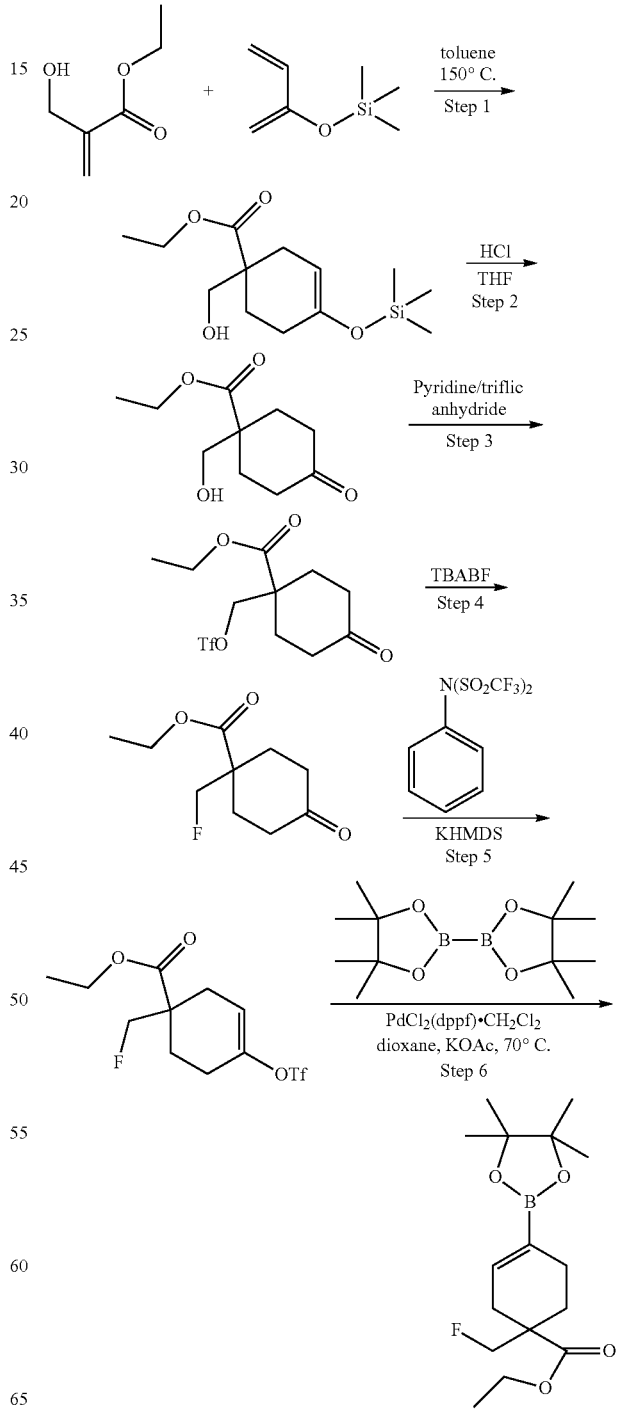

Step 1. Preparation of ethyl 1-(hydroxymethyl)-4-((trimethylsilyl)oxy)cyclohex-3-enecarboxylate

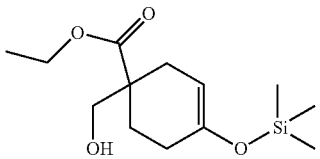 [SMILES: CCOC(=O)C1(CO)CC=C(O[Si](C)(C)C)CC1]

A solution of ethyl 2-(hydroxymethyl)acrylate (5.21 g, 40 mmol) and (buta-1,3-dien-2-yloxy)trimethylsilane (8.54 g, 60.0 mmol) in toluene (100 mL) was flushed with nitrogen, sealed and heated in a pressure flask at 150° C. for 48 h. The resulting light yellow reaction mixture was cooled to room temperature and concentrated in vacuum to give the crude product as an oil which was used for the next step without purification. MS: m/e 201.05 (M+H-silyl)$^+$, 0.839 min (method 4).

Step 2. Preparation of ethyl 1-(hydroxymethyl)-4-oxocyclohexanecarboxylate

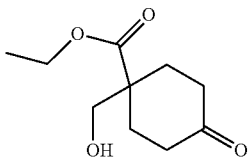

To a solution of ethyl 1-(hydroxymethyl)-4-((trimethylsilyl)oxy)cyclohex-3-enecarboxylate (10.9 g, 40.0 mmol) in THF (5 mL) was added HCl (0.005N) (1 mL, 5.00 μmol). The resulting solution was stirred at room temperature for 18 h. The reaction mixture was extracted with EtOAc (2×10 mL), washed with saturated aqueous NaHCO$_3$ (5 mL) followed by brine (10 mL). The organic extract was dried over Na$_2$SO$_4$, filtered and concentrated in vacuum. The crude product was purified by silica gel chromatography using ethyl acetate/hexanes to give the title compound as a colorless oil (3 g, 37.4%). MS: m/e 200.95 (M+H)$^+$, 0.853 min (method 4). $^1$H NMR (400 MHz, CHLOROFORM-d) δ4.28 (q, J=7.3 Hz, 2H), 3.75 (s, 2H), 2.57-2.45 (m, 2H), 2.45-2.33 (m, 4H), 1.86-1.71 (m, 2H), 1.39-1.30 (m, 3H).

Step 3. Preparation of ethyl 4-oxo-1-((((trifluoromethyl)sulfonyl)oxy)methyl)cyclohexanecarboxylate

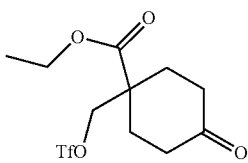 [SMILES: CCOC(=O)C1(COS(=O)(=O)C(F)(F)F)CCC(=O)CC1]

To a stirred mixture of ethyl 1-(hydroxymethyl)-4-oxocyclohexanecarboxylate (1,170 mg, 5.84 mmol) and pyridine (0.614 mL, 7.60 mmol) in DCM (10 mL) at −10° C. was added trifluoromethanesulfonic anhydride (7.60 mL, 7.60 mmol) dropwise. The resulting mixture was stirred at −10° C. for 30 min and washed with ice cold 1N HCl solution and brine. The separated organic layer was dried over sodium sulfate. The solvent was removed and the residue was used as it without purification. MS: m/e 333.05 (M+H)$^+$, 1.969 min (method 4).

Step 4. Preparation of ethyl 1-(fluoromethyl)-4-oxocyclohexanecarboxylate

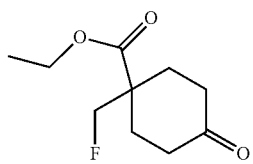

To a stirred mixture of ethyl 4-oxo-1-((((trifluoromethyl)sulfonyl)oxy)methyl)cyclohexanecarboxylate (1.941 g, 5.84 mmol) in DCM (10 mL) at 25° C. was added tetrabutylammonium bifluoride (3.63 mL, 7.01 mmol) dropwise. The resulting mixture was stirred at 25° C. for 18 hours. The reaction mixture was concentrated under vacuum. Two layers were formed upon stirring the residue obtained in 50 mL of hexanes. The top layer was decanted to a flask and dried under vacuum to yield a colorless oil. This residue was purified by flash chromatography using a 12 g silica gel column and a 0-35% EtOAc in hexanes gradient to yield the title compound as a colorless oil (0.20 g, 9.0%). MS: m/e 203.15 (M+H)$^+$, 1.470 min (method 4). $^1$H NMR (400 MHz, CHLOROFORM-d) δ4.49-4.30 (m, 2H), 4.25-4.11 (m, 2H), 2.50-2.35 (m, 4H), 2.33-2.20 (m, 2H), 1.80-1.64 (m, 2H), 1.30-1.20 (m, 3H). $^{19}$F NMR (376 MHz, CHLOROFORM-d) δ-223.02-225.00 (m, 1F).

Step 5. Preparation of ethyl 1-(fluoromethyl)-4-(((trifluoromethyl)sulfonyl)oxy)cyclohex-3-enecarboxylate

KHMDS (1.27 mL, 1.27 mmol) was added to a pale yellow solution of ethyl 1-(fluoromethyl)-4-oxocyclohexanecarboxylate (0.20 g, 0.98 mmol) and 1,1,1-trifluoro-N-phenyl-N-((trifluoromethyl)sulfonyl)methanesulfonamide (0.38 g, 1.07 mmol) in THF (20 mL) at −78° C. The resulting yellow solution was stirred at −78° C. for 2 hr. The reaction mixture was quenched with aqueous saturated ammonium chloride and extracted once with 10 mL of EtOAc. The organic layer was washed with brine (10 mL), dried over Na$_2$SO$_4$, filtered and concentrated in vacuo. The crude product was purified by flash chromatography using a 12 g silica gel column and a 0-10% EtOAc in hexanes gradient to give the title compound as a colorless oil (179 mg, 54.7%). $^1$H NMR (400 MHz, CHLOROFORM-d) δ5.84-5.69 (m, 1H), 4.60-4.37 (m, 2H), 4.30-4.15 (m, 2H), 2.89-2.70 (m, 1H), 2.56-2.33 (m, 2H), 2.32-2.14 (m, 2H), 2.07-1.81 (m, 1H), 1.34-1.22 (m, 3H). ¹⁹F NMR (376 MHz, CHLORO-FORM-d) δ-225.18-225.70 (m, 1F)

Step 6. To a flask containing ethyl 1-(fluoromethyl)-4-(((trifluoromethyl)sulfonyl)oxy)cyclohex-3-enecarboxylate (0.179 g, 0.53 mmol) was added bis(pinacolato)diboron (0.143 g, 0.56 mmol), potassium acetate (0.156 g, 1.59 mmol), and 1,1'-bis(diphenylphosphino)ferrocenepalladium (II) dichloride (0.013 g, 0.016 mmol). The mixture was diluted with dioxane (8 mL), flushed with nitrogen, and heated to 70° C. for 5 h. Upon cooling to rt, the mixture was diluted with water (25 mL) and extracted with ethyl acetate (2×20 mL). The combined organic layers were washed with brine and dried over magnesium sulfate. The drying agent was removed by filtration and the filtrate was concentrated under reduced pressure. The residue was purified by flash chromatography using a 12 g Isco silica gel column and a 0-10% EtOAc in hexanes gradient. The fractions containing the expected product were combined and concentrated under reduced pressure to give the title compound as a clear, colorless oil (91 mg, 54%). MS: m/e 313.20 (M+H)⁺, 2.299 min (method 4). ¹H NMR (400 MHz, CHLOROFORM-d) δ6.50 (td, J=3.9, 2.0 Hz, 1H), 4.59-4.32 (m, 2H), 4.23-4.13 (m, 2H), 2.74-2.52 (m, 1H), 2.30-2.08 (m, 3H), 1.98-1.69 (m, 2H), 1.32-1.20 (m, 15H). ¹⁹F NMR (376 MHz, CHLOROFORM-d) δ-225.59-226.36 (m, 1F).

Alternative method of preparation for the preparation of ethyl 1-(fluoromethyl)-4-oxocyclohexanecarboxylate

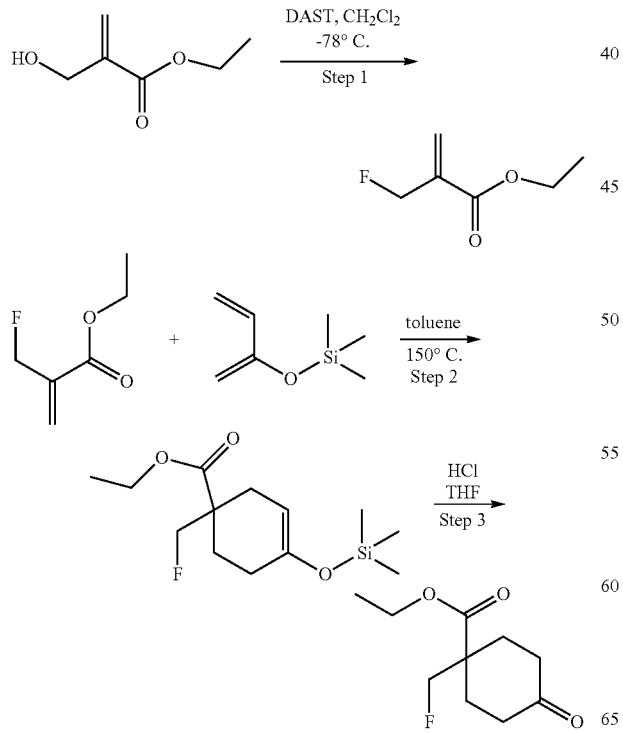

Step 1. Preparation of ethyl 2-(fluoromethyl)acrylate

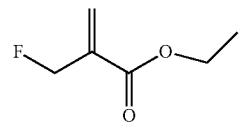

To the solution of ethyl 2-(hydroxymethyl)acrylate (5 g, 38.4 mmol) in DCM (50 mL) was added DAST (6.60 mL, 49.9 mmol) at −78° C. The reaction mixture was stirred at −78° C. for 1 hour. The mixture was warmed to 25° C. and continuously stirred for another 3 hours. The reaction mixture was quenched by the addition of $CH_2Cl_2$ (20 mL) and $NaHCO_3$ saturated aqueous solution (20 mL). The organic layer was separated, and the aqueous layer was extracted twice with $CH_2Cl_2$ (20 mL). The combined organic extracts were dried over sodium sulfate and evaporated to give a residual oil which was used in the next step without purification. ¹H NMR (500 MHz, CHLOROFORM-d) δ6.49-6.33 (m, 1H), 6.03-5.87 (m, 1H), 6.45-5.84 (m, 2H), 4.27 (q, J=7.1 Hz, 2H), 1.33 (t, J=7.1 Hz, 3H). ¹⁹F NMR (470 MHz, CHLOROFORM-d) δ-220.33-221.86 (m, 1F).

Step 2. Preparation of ethyl 1-(fluoromethyl)-4-((trimethylsilyl)oxy)cyclohex-3-enecarboxylate

A solution of ethyl 2-(fluoromethyl)acrylate (4.7 g, 35.6 mmol)) and (buta-1,3-dien-2-yloxy)trimethylsilane (10.12 g, 71.1 mmol) in toluene (100 mL)) was flushed with nitrogen, sealed and heated at 150° C. in a pressure vessel for 48 h. The resulting pale yellow solution was cooled to room temperature and concentrated in vacuum to give the title compound as an oil which was used in the next step without further purification. ¹H NMR (400 MHz, CHLOROFORM-d) δ4.83 (t, J=3.3 Hz, 1H), 4.64-4.38 (m, 2H), 4.25-4.12 (m, 2H), 2.62-2.48 (m, 1H), 2.19-1.99 (m, 4H), 1.93-1.78 (m, 1H), 1.34-1.22 (m, 3H), 0.24-0.15 (m, 9H). ¹⁹F NMR (470 MHz, CHLOROFORM-d) δ-224.80-225.37 (m, 1F).

Step 3. Preparation of ethyl 1-(fluoromethyl)-4-oxocyclohexanecarboxylate

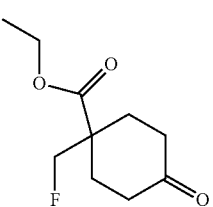

To a solution of ethyl 1-(fluoromethyl)-4-((trimethylsilyl)oxy)cyclohex-3-enecarboxylate (9.76 g, 35.6 mmol) in THF (5 mL) was added HCl (0.005N) (1 mL, 5.00 µmol). The resulting solution was stirred at room temperature overnight. The reaction mixture was extracted with EtOAc (2×10 mL), washed with aqueous saturated NaHCO₃ (5 mL) followed by brine (10 mL), dried over Na₂SO₄, filtered and concentrated in vacuum. The crude product was purified by flash chromatography using a 80 g silica gel column and a 0-25% EtOAc in hexanes gradient. The fraction containing the expected product was collected and concentrated in vacuum to give the title compound as a colorless oil (6.5 g, 90.2%). $^1$H NMR (400 MHz, CHLOROFORM-d) δ4.59-4.42 (m, 2H), 4.30 (q, J=7.0 Hz, 2H), 2.58-2.34 (m, 6H), 1.88-1.73 (m, 2H), 1.33 (t, J=7.2 Hz, 3H). $^{19}$F NMR (376 MHz, CHLOROFORM-d) δ-223.54-223.99 (m, 1F).

Preparation of benzyl
1-(fluoromethyl)-4-oxocyclohexanecarboxylate
Method A

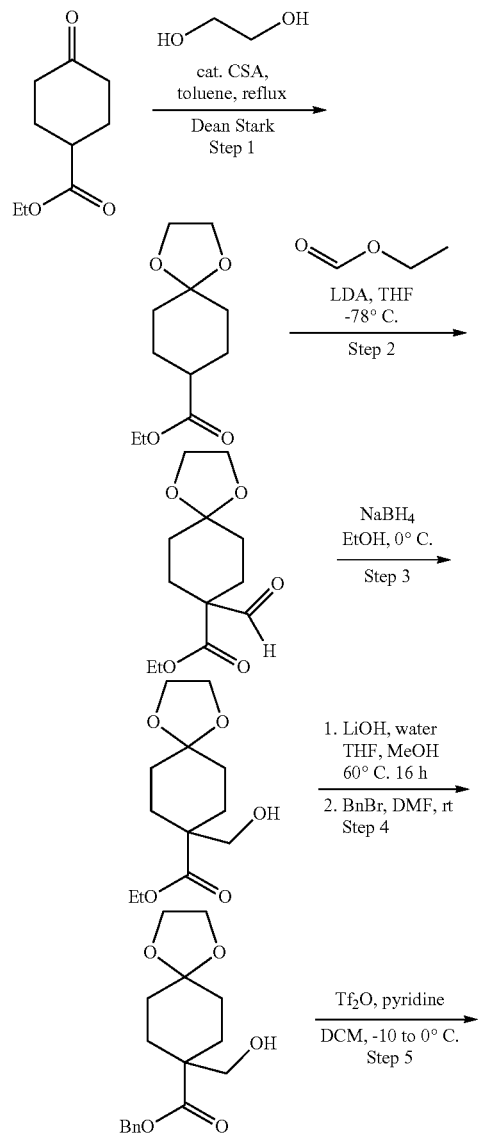

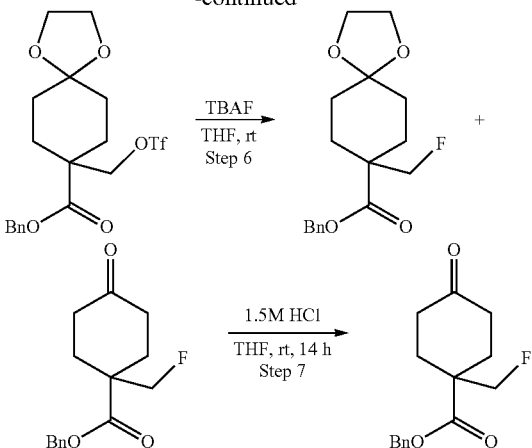

Step 1. Preparation of ethyl
1,4-dioxaspiro[4.5]decane-8-carboxylate

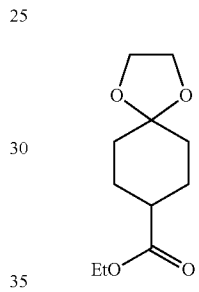

Into a 3 L, 3 neck round bottom flask was placed ethyl 4-oxocyclohexanecarboxylate (100 g, 570 mmol), ethane-1,2-diol (0.159 L, 2849 mmol), ((1S,4R)-7,7-dimethyl-2-oxobicyclo[2.2.1]heptan-1-yl)methanesulfonic acid (1.324 g, 5.70 mmol) and dry toluene (1.2 L). A Dean-Stark water trap and a condenser were installed and the mixture heated to reflux with stirring. Immiscible distillate was collected in the Dean-Stark trap and was periodically removed. After 28 h of total reflux time, a total of 82 mL of immiscible distillate had been removed from the Dean-Stark trap. After the mixture had cooled to approximately 40° C., sat. NaHCO₃ (400 mL) was added to the reaction mixture with rapid stirring. The mixture was transferred to a separatory funnel, shaken and the phases separated. The organic layer was washed with water (4×500 mL), then with 5% NaHCO₃ (200 mL) and then with brine (100 mL). The organic material was dried over anhydrous MgSO₄, filtered and concentrated in vacuum to give a slightly yellow viscous oil (118.50 g, 97% yield). $^1$H NMR (400 MHz, CHLOROFORM-d) δ4.15 (q, J=7.3 Hz, 2H), 3.96 (s, 4H), 2.41-2.27 (m, 1H), 1.96 (dt, J=8.7, 4.3 Hz, 2H), 1.89-1.74 (m, 4H), 1.68-1.49 (m, 2H), 1.27 (t, J=7.1 Hz, 3H). $^{13}$C NMR (101 MHz, CHLOROFORM-d) δ175.2, 108.1, 64.3, 60.3, 41.6, 33.8, 26.3, 14.3.

Step 2: Preparation of ethyl 8-formyl-1,4-dioxas-piro[4.5]decane-8-carboxylate

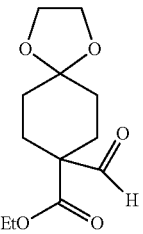

To a −78° C. solution of ethyl 1,4-dioxaspiro[4.5]decane-8-carboxylate (32.31 g, 151 mmol) in THF (250 mL) was added a solution of 2M lithium diisopropylamide (98 mL, 196 mmol) in THF via a cannula over 5 mins. The resulting brown solution was stirred at −78° C. After 1 h, the cold bath was replaced with an ice bath and the reaction mixture was stirred at 0° C. for 1 h. The reaction mixture was again chilled to −78° C. and treated with a solution of ethyl formate (18.65 mL, 226 mmol) in THF (40 mL) added dropwise over 45 min. The resulting light brown reaction mixture was stirred at −78° C. for 1 h. The cold bath was removed and to the mixture was added dropwise saturated aqueous NH$_4$Cl (250 mL) and the mixture stirred at ambient temperature for 30 min. The resulting yellow mixture was extracted with EtOAc (3×300 mL). The combined organic phase was washed with 0.5N HCl (300 mL), then with brine, dried over MgSO$_4$, filtered and concentrated to a brown viscous oil. The crude material was purified by flash column chromatography over silica gel (750 g silica, step elution 9:1 hexanes/EtOAc and 5:1 hexanes/EtOAc) to provide recovered starting material, ethyl 1,4-dioxaspiro[4.5]decane-8-carboxylate (8.6 g, 40.1 mmol, 26.6% yield) and the desired product, ethyl 8-formyl-1,4-dioxaspiro[4.5]decane-8-carboxylate (20.1 g, 83 mmol, 55.0% yield), both as viscous yellow oils. $^1$H NMR (400 MHz, CHLOROFORM-d) δ9.50 (s, 1H), 4.17 (q, J=7.2 Hz, 2H), 3.94-3.86 (m, 4H), 2.24-2.09 (m, 2H), 2.01 (ddd, J=13.5, 8.3, 5.1 Hz, 2H), 1.75-1.48 (m, 4H), 1.23 (t, J=7.2 Hz, 3H).

Step 3: Preparation of ethyl 8-(hydroxymethyl)-1,4-dioxaspiro[4.5]decane-8-carboxylate

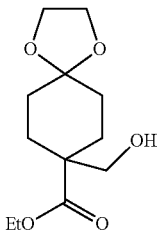

To a 0° C. solution of ethyl 8-formyl-1,4-dioxaspiro[4.5]decane-8-carboxylate (28.9 g, 119 mmol) in ethanol (300 mL) was added sodium borohydride (5.30 g, 137 mmol) and the resulting mixture was stirred at 0° C. After 3 h, the reaction mixture was quenched with saturated aqueous NH$_4$Cl (200 mL) added dropwise via a dropping funnel. The ice bath was removed and the resulting slurry was treated slowly with H$_2$O (150 mL). The resulting mixture was filtered to remove a small amount of white solid. The liquid filtrate was concentrated to remove most of the organic solvent, and the remainder was extracted with EtOAc (4×250 mL). The combined organic phase was washed with brine, dried over MgSO$_4$, filtered, concentrated and dried in vacuum to give ethyl 8-(hydroxymethyl)-1,4-dioxaspiro [4.5]decane-8-carboxylate (27.7 g, 113 mmol, 95% yield) as a clear viscous oil. The material from this experiment was used directly in the next step without further purification. In a separate experiment the crude material was purified by flash column chromatography (SiO$_2$, elution 3:1 hexanes: EtOAc) to give ethyl 8-(hydroxymethyl)-1,4-dioxaspiro [4.5]decane-8-carboxylate in 91% yield. $^1$H NMR (400 MHz, CHLOROFORM-d) δ4.18 (q, J=7.1 Hz, 2H), 3.98-3.87 (m, 4H), 3.61 (d, J=6.1 Hz, 2H), 2.23 (br. s., 1H), 2.17-2.07 (m, 2H), 1.72-1.51 (m, 6H), 1.32-1.20 (m, 3H).

Step 4. Preparation of benzyl 8-(hydroxymethyl)-1,4-dioxaspiro[4.5]decane-8-carboxylate

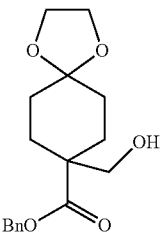

To a solution of ethyl 8-(hydroxymethyl)-1,4-dioxaspiro [4.5]decane-8-carboxylate (27.6 g, 113 mmol) in THF (150 mL) and MeOH (50 mL) was added a solution of 3N aqueous lithium hydroxide (45.2 mL, 136 mmol) and the mixture was heated to 60° C. with stirring for 17 h. Additional 3N aqueous lithium hydroxide (30.1 mL, 90 mmol) was then added and the mixture was heated to 60° C. for an additional 14 h. The reaction mixture was concentrated and dried in vacuum to give a residue containing the corresponding carboxylate (24.5 g, 107 mmol) which was used without further purification.

To this residue in DMF (200 mL) was added benzyl bromide (12.98 mL, 107 mmol) and the resulting mixture was stirred at rt for 17 h. The reaction mixture was concentrated to about half of the original volume, diluted with EtOAc (250 mL) and washed with 1N HCl (200 mL). The aqueous phase was extracted with 3×250 mL EtOAc. The combined organic phase was washed with H$_2$O (100 mL), brine, dried over MgSO$_4$, filtered and concentrated to a light yellow viscous oil. The crude material was purified by flash column chromatography (Sift, elution step gradient 70:30 hex:EtOAc then 1:1 hex:EtOAc) and dried in vacuum to give benzyl 8-(hydroxymethyl)-1,4-dioxaspiro[4.5]decane-8-carboxylate (23.1 g, 71.6 mmol, 63% yield over 3 steps). $^1$H NMR (400 MHz, CHLOROFORM-d) δ7.40-7.28 (m, 5H), 5.16 (s, 2H), 3.91 (s, 4H), 3.64 (s, 2H), 2.34 (br. s., 1H), 2.22-2.12 (m, 2H), 1.70-1.63 (m, 4H), 1.62-1.54 (m, 2H). $^{13}$C NMR (101 MHz, CHLOROFORM-d) δ175.3, 135.8, 128.5 (s, 2C), 128.1, 127.8, 108.3, 68.5, 66.4, 64.2, 64.1, 48.1, 31.3, 27.9.

Step 5. Preparation of benzyl 8-((((trifluoromethyl)sulfonyl)oxy)methyl)-1,4-dioxaspiro[4.5]decane-8-carboxylate

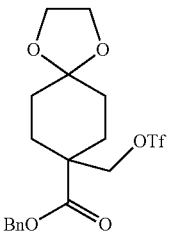

In a 500 mL round bottom flask were combined benzyl 8-(hydroxymethyl)-1,4-dioxaspiro[4.5]decane-8-carboxylate (14.9 g, 48.6 mmol) with dry DCM (250 mL). The solution was chilled in an ice/acetone bath to approx. −10° C. and to it was added pyridine (5.31 mL, 65.7 mmol) followed by the dropwise addition of Tf$_2$O (11.09 mL, 65.7 mmol) over 30 min. The slightly yellow suspension was stirred at 0° C. (ice water bath) for 1.5 h.

The resulting deep orange mixture with significant suspended solids was concentrated in vacuum to leave a residue that was put under vacuum to remove excess triflic anhydride, then the residue was redissolved in DCM (150 mL). The mixture was filtered to remove a significant quantity of white solid which was rinsed with DCM. The deep reddish/orange filtrate was concentrated and purified by flash silica gel column chromatography (330 g silica, elution 100% DCM). Product fractions were combined and concentrated to a thick orange oil which was placed under high vacuum with stirring overnight. The color turned to blue/green. Thus was obtained the desired product (20.94 g, 98% yield) as a blue/green viscous oil. $^1$H NMR (400 MHz, CHLOROFORM-d) δ7.48-7.30 (m, 5H), 5.21 (s, 2H), 4.53 (s, 2H), 4.04-3.87 (m, 4H), 2.30-2.14 (m, 2H), 1.76-1.56 (m, 6H). $^{19}$F NMR (376 MHz, CHLOROFORM-d) δ-74.39 (s, 1F).

Step 6. Preparation of benzyl 8-(fluoromethyl)-1,4-dioxaspiro[4.5]decane-8-carboxylate

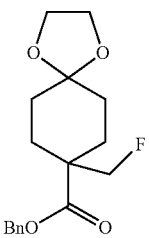

In a 500 mL round bottom flask under nitrogen atmosphere were combined benzyl 8-((((trifluoromethyl)sulfonyl)oxy)methyl)-1,4-dioxaspiro[4.5]decane-8-carboxylate (20.76 g, 47.4 mmol) with anhydrous THF (150 mL) which was introduced via cannula. To the blue solution was added dropwise via addition funnel TBAF, 1.0M in THF (71.0 mL, 71.0 mmol) dropwise over 15 min. The mixture immediately turned canary yellow when TBAF was added. The mixture was stirred at rt for 1 h. The crude mixture was concentrated to leave a thick oil which was diluted with ethyl acetate (700 mL) and washed with water (2×250 mL) and with brine (100 mL). The organic phase was dried over MgSO$_4$, filtered and concentrated to a thick yellow residue. Purification by flash silica gel column chromatography (330 g silica, elution gradient 100% hexanes to 2:1 hexanes:EtOAc) gave the desired product as a yellow oil (13.73 g, 94% yield). LCMS: m/e 309.2 (M+H)$^+$, 1.27 min (method 3). $^1$H NMR (400 MHz, CHLOROFORM-d) δ7.44-7.31 (m, 5H), 5.21 (s, 2H), 4.45 (d, J=47.2 Hz, 2H), 4.01-3.89 (m, 4H), 2.28-2.16 (m, 2H), 1.75-1.55 (m, 6H). $^{19}$F NMR (376 MHz, CHLOROFORM-d) δ-223.25 (t, J=46.8 Hz, 1F).

Step 7. In a 2 L round bottom flask cooled in an ice bath were combined benzyl 8-(fluoromethyl)-1,4-dioxaspiro[4.5]decane-8-carboxylate (13.72 g, 44.5 mmol) with THF (500 mL) and then hydrochloric acid, 1.5M aqueous (534 mL, 801 mmol) was added slowly over 2 min. The ice bath was removed and the mixture was stirred at rt for 15 h.

The mixture was concentrated in vacuum to remove the organic and the remnant was extracted with ethyl acetate (300 mL). The ethyl acetate phase was washed with water (2×200 mL) and with brine (50 mL). Concentration in vacuum provided the desired product (12.13 g, quantitative) as a yellow oil. LCMS: m/e 265.3 (M+H)$^+$, 1.19 min (method 3). $^1$H NMR (400 MHz, CHLOROFORM-d) δ7.47-7.32 (m, 5H), 5.27 (s, 2H), 4.52 (d, J=47.2 Hz, 2H), 2.57-2.42 (m, 4H), 2.42-2.31 (m, 2H), 1.87-1.76 (m, 2H). $^{19}$F NMR (376 MHz, CHLOROFORM-d) δ-223.41 (t, J=46.8 Hz, 1F).

Method B

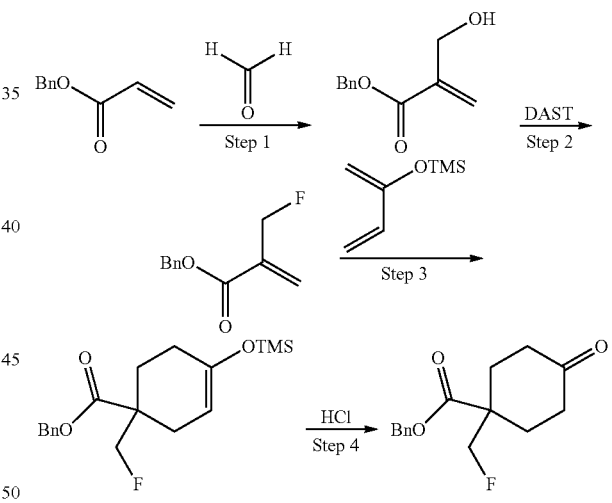

Step 1. Preparation of benzyl 2-(hydroxymethyl)acrylate

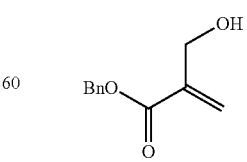

In a 1-L flask was placed benzyl acrylate (44.6 mL, 292 mmol), dioxane (290 mL), 1,4-diazabicyclo[2.2.2]octane (32.7 g, 292 mmol) and water (270 mL). The mixture was vigorously stirred at RT forming an emulsion. To the stirring mixture was added an aqueous solution of formaldehyde (37%, 23.9 mL, 321 mmol) and the stirring was continued for 14 hours at RT. The crude reaction mixture was extracted with methylene chloride (3×150 mL). The organic layers were separated, combined and washed with a 50:50 mixture of saturated aqueous ammonium chloride and HCl (0.2 N). Evaporation and concentration in vacuum (2 cm Hg) at 45° C. gave 49.1 g of a free flowing syrup. The crude product was purified on a silica gel column eluted with a gradient mixture of EtOAc/Hexanes to give the title compound as a clear colorless syrup (27 g, 141 mmol, 48%). LCMS: m/e 193.05 (M+H)$^+$, 1.78 min (Method 5). $^1$H NMR (500 MHz, CHLOROFORM-d) δ7.50-7.30 (m, 5H), 6.34 (s, 1H), 5.89 (s, 1H), 5.25 (s, 2H), 4.38 (d, J=6.4 Hz, 2H), 2.20 (t, J=6.6 Hz, 1H); $^{13}$C NMR (126 MHz, CHLOROFORM-d) δ166.1, 139.3, 135.7, 128.7, 128.4, 128.2, 126.2, 66.6, 62.7.

Step 2. Preparation of benzyl 2-(fluoromethyl)acrylate

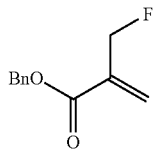

Benzyl 2-(hydroxymethyl)acrylate (13.7 g, 71.3 mmol) was dissolved in dry methylene chloride (100 mL) under nitrogen and the mixture was cooled at −78° C. To this stirring solution and using a polyethylene pipette, was added diethylaminosulfur trifluoride (DAST, 13.0 mL, 98 mmol) in 4 portions over a period of 5 minutes. A pale orange solution was formed. Once addition was complete, the dry-ice bath was removed and the reaction temperature was allowed to rise to RT. Stirring continued at RT for a total of 4 hours. The reaction mixture was transferred dropwise, into a chilled (~4° C.) 50:50 mixture of saturated aqueous sodium bicarbonate and water. Once all of the crude reaction mixture was transferred, it was extracted with BHT-stabilized ether (3×150 mL). The organic layers were combined, and washed once with water (50 mL). The solvent from the organic phase was removed in vacuum at sub-ambient temperature (~15° C.) to constant weight (14.2 g, quant.). The crude material was used immediately in the next step. $^1$H NMR (500 MHz, CHLOROFORM-d) δ7.44-7.34 (m, 5H), 6.49-6.43 (m, 1H), 5.99 (dt, J=2.8, 1.5 Hz, 1H), 5.26 (s, 2H), 5.13 (d, J=46.5 Hz, 2H); $^{19}$F NMR (470 MHz, CHLOROFORM-d) δ-220.91 (t, J=46.2 Hz).

Step 3—Preparation of benzyl 1-(fluoromethyl)-4-((trimethylsilyl)oxy)cyclohex-3-enecarboxylate

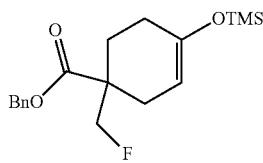

To a 500 mL resealable pressure vessel was added the crude starting material benzyl 2-(fluoromethyl)acrylate (14.2 g, 73.1 mmol) and (buta-1,3-dien-2-yloxy)trimethylsilane (Sigma Aldrich material used as supplied, 18.73 g, 132 mmol) in toluene (200 mL). The vessel was evacuated to 80 micron Hg at −78° C., followed by purging with nitrogen. The process was repeated twice. The flask was sealed, and warmed to RT before it was immersed into an oil bath at 125° C. for 22 hours. The mixture was allowed to cool to RT. A small aliquot (25 µL) was removed from the crude reaction, vacuum-dried at RT for NMR analyses in $^1$H and $^{19}$F. The NMR results were consistent with the formation of the title compound and small amount of the corresponding Diels-Alder regioisomer. $^1$H NMR (400 MHz, CHLOROFORM-d) δ7.43-7.29 (m, 5H), 5.18 (s, 2H), 4.80 (d, J=3.0 Hz, 1H), 4.52 (dq, J=46.9, 8.4 Hz, 2H), 2.65-2.49 (m, 1H), 2.21-2.00 (m, 4H), 1.92-1.78 (m, 1H), 0.24-0.12 (m, 9H); $^{19}$F NMR (376 MHz, CHLOROFORM-d) δ-224.76 (t, J=47.7 Hz, 1F) and a minor $^{19}$F NMR (376 MHz, CHLOROFORM-d) δ-225.20 (t, J=46.8 Hz, 0.06F). The crude material was evaporated and dried under vacuum (20 micron Hg) at −35° C. until constant weight (24.6 g, quant.). This crude material was used in the next step as is without further purification.

Step 4. The crude material from the previous step (24.6 gm, 73 mmol) was dissolved in THF (200 mL) at RT to form a clear solution. Aqueous 1N HCl (2 mL, 2 mmol) and water 4 mL were added. The clear solution was stirred at RT for a total of 16 hours. The crude reaction mixture was quenched with 150 mL of a 50:50 mixture of saturated aqueous ammonium sodium bicarbonate and water. The organic layer was extracted with EtOAc (3×75 mL). The organic layers were combined, and evaporated to dryness to give 18.8 g of a thick syrup. The crude residue was purified using a 330 g silica gel column eluted with a gradient mixture of 0 to 25% v/v of ethyl acetate in hexanes, in ~25 column volumes to render the title compound (15.6 g, 81.0%). LCMS: m/e 265.15 (M+H)$^+$, 1.60 min (Method 1). $^1$H NMR (400 MHz, CHLOROFORM-d) δ7.50-7.30 (m, 5H), 5.26 (s, 2H), 4.43 (d, J=46.9 Hz, 2H), 2.54-2.29 (m, 6H), 1.90-1.71 (m, 2H); $^{19}$F NMR (376 MHz, CHLOROFORM-d) δ-223.47 (t, J=46.8 Hz, 1F).

Preparation of (R)-benzyl 1-(fluoromethyl)-4-(4,4,5,5-tetramethyl-1,3,2-dioxaborolan-2-yl)cyclohex-3-enecarboxylate and (S)-benzyl 1-(fluoromethyl)-4-(4,4,5,5-tetramethyl-1,3,2-dioxaborolan-2-yl)cyclohex-3-enecarboxylate

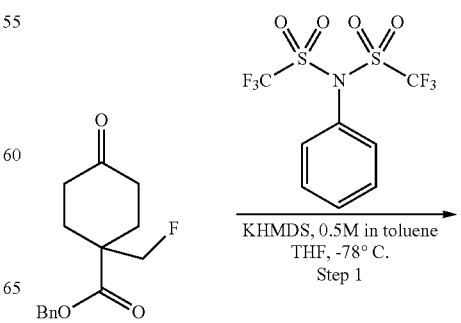

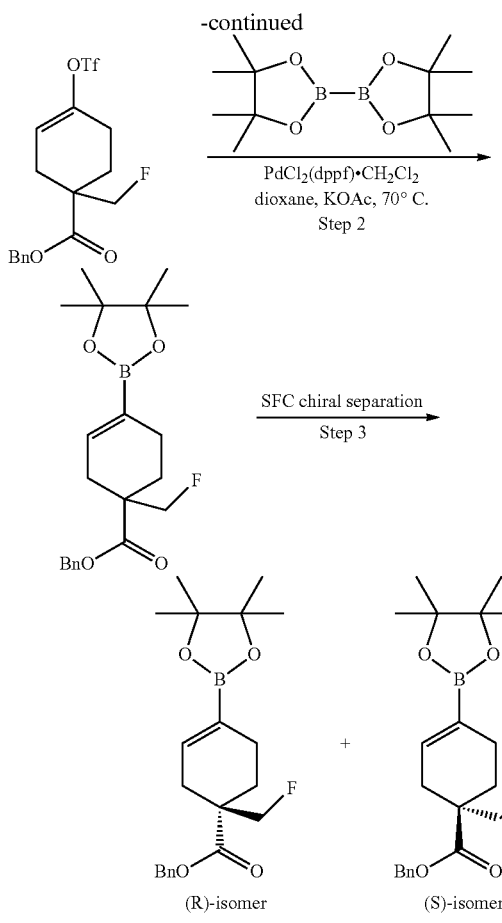

Step 1. Preparation of benzyl 1-(fluoromethyl)-4-(((trifluoromethyl)sulfonyl)oxy)cyclohex-3-enecarboxylate

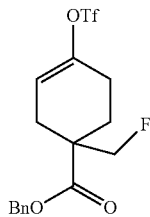

In a 500 mL round bottom flask were combined benzyl 1-(fluoromethyl)-4-oxocyclohexanecarboxylate (12.65 g, 47.9 mmol) and N,N-bis(trifluoromethylsulfonyl)aniline (18.81 g, 52.7 mmol) in anhydrous tetrahydrofuran (250 mL). The solution was cooled to −78° C. in a dry ice/acetone bath. To the cold solution was added dropwise potassium hexamethyldisilazide, 0.5M in toluene (105 mL, 52.7 mmol) over 30 min. The mixture was stirred at −78° C. for a total of 2.5 h and was then lifted out of the cold bath and stirred for an additional 20 min at rt. The mixture was placed back in the −78° C. bath and to it was added with stirring 125 mL of saturated aqueous ammonium chloride. The resulting suspension was removed from the cold bath and allowed to come to rt while stirring. The mixture was concentrated in vacuum to remove the organic solvent, then to the mixture was added ethyl acetate (600 mL) and water (300 mL) and the mixture was shaken and the phases were separated. The organic layer was washed with water (2×200 mL) and with brine (50 mL). The organic layer was dried over MgSO$_4$, filtered and concentrated in vacuum to leave a yellow/orange oil. The crude residue was purified by flash silica gel column chromatography (800 g silica, elution isocratic 3:2 hexanes: DCM). Product fractions were combined and concentrated in vacuum to give the desired product (17.43 g, 92% yield) as a very slightly yellow oil. $^1$H NMR (400 MHz, CHLOROFORM-d) δ7.43-7.31 (m, 5H), 5.78 (br. s., 1H), 5.26-5.15 (m, 2H), 4.52 (dm, J=46.7 Hz, 2H), 2.78 (d, J=16.9 Hz, 1H), 2.52-2.33 (m, 2H), 2.33-2.17 (m, 2H), 1.94 (dt, J=13.8, 6.9 Hz, 1H). $^{19}$F NMR (376 MHz, CHLOROFORM-d) δ-73.88 (s, 1F), −225.02 (t, J=46.8 Hz, 1F).

Step 2. Preparation of benzyl 1-(fluoromethyl)-4-(4,4,5,5-tetramethyl-1,3,2-dioxaborolan-2-yl)cyclohex-3-enecarboxylate

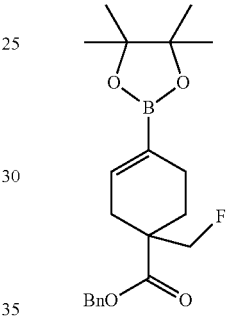

In a 500 mL round bottom flask were combined benzyl 1-(fluoromethyl)-4-(((trifluoromethyl)sulfonyl)oxy)cyclohex-3-enecarboxylate (17.42 g, 44.0 mmol), potassium acetate (0.030 g, 0.307 mmol), 4,4,4',4',5,5,5',5'-octamethyl-2,2'-bi(1,3,2-dioxaborolane) (11.72 g, 46.1 mmol), 1,1'-bis(diphenylphosphino)ferrocenepalladium(II) dichloride (3.03 mg, 3.69 μmol) and anhydrous dioxane (200 mL). The flask was placed under a nitrogen atmosphere and heated to 70° C. After 5 h, the mixture was allowed to cool to rt and stood overnight. The reaction mixture was concentrated in vacuum and the crude deep red residue was diluted with ethyl acetate (600 mL) and water (300 mL). The mixture was shaken and phases were separated. The organic was washed with water (250 mL) and then with brine (100 mL). The organic phase was dried over anhydrous MgSO$_4$, filtered and concentrated in vacuum to a deep red viscous oil. Purification of the crude mixture by flash silica gel column chromatography (800 g silica; step elution 1:3 hexanes:DCM for 4 L, then 100% DCM for 5 L. 2 g of material from the mixed fractions from the first purification were repurified over 80 g of silica gel, elution gradient 100% hexanes to 100% DC,) to give the desired product as a colorless thick oil (13.06 g, 79.4% yield). LCMS: m/e 375.3 (M+H)$^+$, 1.52 min (method 3). $^1$H NMR (400 MHz, CHLOROFORM-d) δ7.44-7.30 (m, 5H), 6.54 (br. s., 1H), 5.25-5.11 (m, 2H), 4.51 (dm, J=47.4 Hz, 2H), 2.67 (d, J=19.3 Hz, 1H), 2.29-2.10 (m, 3H), 2.02-1.89 (m, 1H), 1.86-1.74 (m, 1H), 1.28 (s, 12H). $^{19}$F NMR (376 MHz, CHLOROFORM-d) δ-225.62 (t, J=45.1 Hz, 1F).

Step 3. Racemic benzyl 1-(fluoromethyl)-4-(4,4,5,5-tetramethyl-1,3,2-dioxaborolan-2-yl)cyclohex-3-enecarboxylate (11.15 g, 0.0298 mmol) was purified by supercritical fluid chromatography (SFC Method) to provide the separated single isomer title compounds: (R)-benzyl 1-(fluoromethyl)-4-(4,4,5,5-tetramethyl-1,3,2-dioxaborolan-2-yl)cyclohex-3-enecarboxylate. This was the first isomer to elute from the SFC chiral separation. The product was isolated as a yellow oil (5.45 g, 98% SFC recovery, 99.2% chiral purity). $^1$H NMR (400 MHz, CHLOROFORM-d) δ7.42-7.30 (m, 5H), 6.54 (br. s., 1H), 5.24-5.12 (m, 2H), 4.51 (dm, J=47.2 Hz, 2H), 2.67 (d, J=19.3 Hz, 1H), 2.27-2.10 (m, 3H), 2.00-1.90 (m, 1H), 1.85-1.75 (m, 1H), 1.28 (s, 12H). $^{19}$F NMR (376 MHz, CHLOROFORM-d) δ-225.62 (t, J=46.8 Hz, 1F).

(S)-benzyl 1-(fluoromethyl)-4-(4,4,5,5-tetramethyl-1,3,2-dioxaborolan-2-yl)cyclohex-3-enecarboxylate. This was the second isomer to elute from the SFC chiral separation. The product was isolated as a yellow oil (4.94 g, 89% SFC recovery, 99.3% chiral purity). $^1$H NMR (400 MHz, CHLOROFORM-d) δ7.43-7.31 (m, 5H), 6.54 (br. s., 1H), 5.24-5.13 (m, 2H), 4.52 (dm, J=47.2 Hz, 2H), 2.68 (d, J=19.3 Hz, 1H), 2.27-2.10 (m, 3H), 2.01-1.90 (m, 1H), 1.85-1.75 (m, 1H), 1.28 (s, 12H). $^{19}$F NMR (376 MHz, CHLOROFORM-d) δ-225.61 (t, J=48.6 Hz, 1F).

Intermediate 1

Preparation of (3aR,5aR,5bR,7aR,11aR,11bR,13aS)-1-isopropyl-5a,5b,8,8,11a-pentamethyl-3a-(oxiran-2-yl)-2-oxo-3,3a,4,5,5a,5b,6,7,7a,8,11,11a,11b,12,13,13a-hexadecahydro-2H-cyclopenta[a]chrysen-9-yl trifluoromethanesulfonate

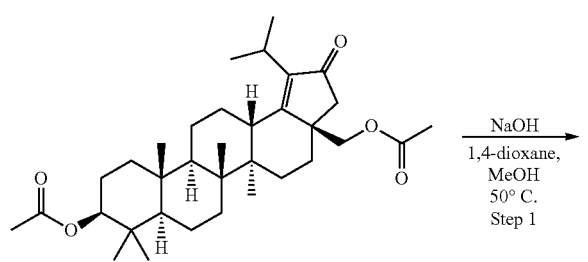

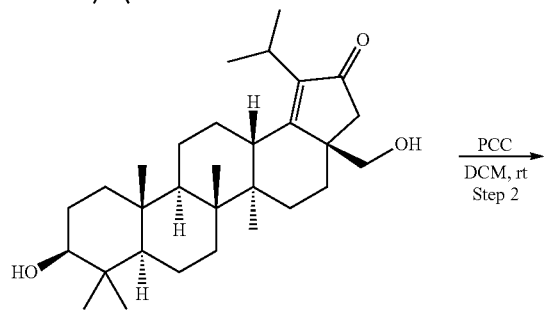

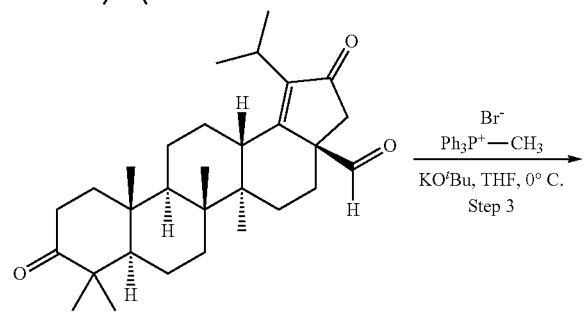

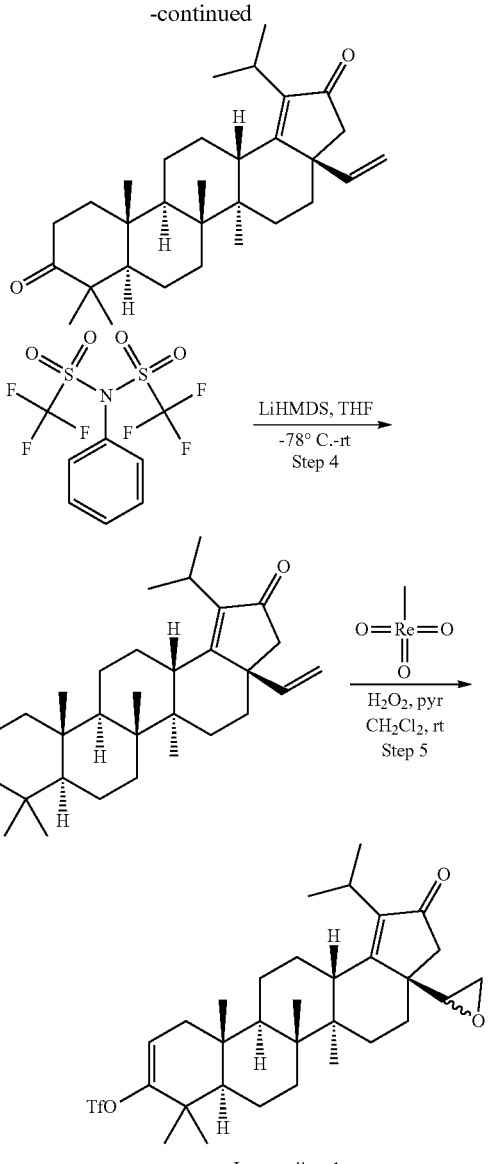

Step 1. Preparation of (3aR,5aR,5bR,7aR,9S,11aR,11bR,13aS)-9-hydroxy-3a-(hydroxymethyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one To a solution of ((3aR,5aR,5bR,7aR,9S,11aR,11bR,13aS)-9-acetoxy-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-3a-yl)methyl acetate (2.00 g, 3.70 mmol) in 1,4-dioxane (30 mL) and methanol (10 mL) was added sodium hydroxide (1N) (18.49 mL, 18.49 mmol). The suspension was warmed to 50° C. for six hours, then cooled to rt and stirred for 18 h. The mixture was partially concentrated under reduced pressure then was acidified with 1N HCl. The solids were collected by filtration and washed with water to give the title compound (1.7 g, 3.7 mmol, 100% yield) as an off-white solid. LC/MS: m/e 457.4 (M+H)$^+$, 1.86 minutes (method 1). $^1$H NMR (500 MHz, CHLOROFORM-d) δ3.77-3.65 (m, 2H), 3.25-3.16

(m, 2H), 2.79 (dd, J=12.7, 3.4 Hz, 1H), 2.44 (d, J=18.6 Hz, 1H), 2.04-1.73 (m, 6H), 1.22 (d, J=6.9 Hz, 3H), 1.21 (d, J=6.8 Hz, 3H), 1.14 (s, 3H), 0.99 (s, 3H), 0.96 (s, 3H), 0.91 (s, 3H), 1.72-0.85 (m, 14H), 0.78 (s, 3H), 0.74-0.71 (m, 1H).

Step 2. Preparation of (3aR,5aR,5bR,7aR,11aR, 11bR,13aS)-1-isopropyl-5a,5b,8,8,11a-pentamethyl-2,9-dioxo-3,3a,4,5,5a,5b,6,7,7a,8,9,10,11,11a,11b, 12,13,13a-octadecahydro-2H-cyclopenta[a]chrysene-3a-carbaldehyde To a suspension of (3aR,5aR,5bR,7aR,9S,11aR,11bR, 13aS)-9-hydroxy-3a-(hydroxymethyl)-1-isopropyl-5a,5b,8, 8,11a-pentamethyl-3,3a,4,5,5a,5b,6,7,7a,8,9,10,11,11a,11b, 12,13,13a-octadecahydro-2H-cyclopenta[a]chrysen-2-one (1.69 g, 3.7 mmol) in dichloromethane (40 mL) was added PCC (1.994 g, 9.25 mmol) in two portions over 15 minutes. The mixture was stirred at rt. After 5 h an additional 0.5 g of PCC was added and the mixture was stirred at rt. After 6.5 h of stirring (total), the mixture was passed through a plug of silica gel and celite (washed with dichloromethane, then 1:1 ethyl acetate:hexanes). The filtrate was concentrated under reduced pressure to give the title product (1.52 g, 3.36 mmol, 91% yield) as an off-white foam. LC/MS: m/e 453.4 (M+H)$^+$, 3.06 minutes (method 1). $^1$H NMR (500 MHz, CHLOROFORM-d) δ9.33 (d, J=1.4 Hz, 1H), 3.25 (spt, J=6.9 Hz, 1H), 2.59 (dd, J=12.8, 3.2 Hz, 1H), 2.56-2.36 (m, 4H), 2.11-2.03 (m, 2H), 2.02-1.84 (m, 3H), 1.24 (d, J=6.9 Hz, 3H), 1.24 (d, J=6.9 Hz, 3H), 1.09 (s, 3H), 1.07 (s, 3H), 1.04 (s, 3H), 0.98 (s, 3H), 0.97 (s, 3H), 1.64-0.90 (m, 11H).

Step 3. (3aS,5aR,5bR,7aR,11aR,11bR,13aS)-1-isopropyl-5a,5b,8,8,11a-pentamethyl-3a-vinyl-3a,4,5, 5a,5b,6,7,7a,8,10,11,11a,11b,12,13,13a-hexadecahydro-2H-cyclopenta[a]chrysene-2,9(3H)-dione A suspension of methyltriphenylphosphonium bromide (1.559 g, 4.37 mmol) in THF (15 mL) was cooled to 0° C. and potassium tert-butoxide (1M in THF) (4.70 mL, 4.70 mmol) was added. The mixture was removed from the ice bath and stirred for 30 minutes at rt. The mixture was again cooled to 0° C. and a solution of (3aR,5aR,5bR,7aR,11aR, 11bR,13aS)-1-isopropyl-5a,5b,8,8,11a-pentamethyl-2,9-dioxo-3,3a,4,5,5a,5b,6,7,7a,8,9,10,11,11a,11b,12,13,13a-octadecahydro-2H-cyclopenta[a]chrysene-3a-carbaldehyde (1.52 g, 3.36 mmol) in THF (15 mL) was added to the cooled solution and the mixture was stirred for 30 minutes 0° C. The mixture was diluted with water (50 mL) and partially concentrated under reduced pressure. The mixture was extracted with ethyl acetate (3×50 mL), washed with brine, dried over magnesium sulfate, filtered, and concentrated under reduced pressure. The residue was purified by flash chromatography using a 0-20% ethyl acetate in hexanes gradient and an 80 g silica gel column to give the title compound (1.15 g, 2.55 mmol, 76% yield) as an off-white solid. $^1$H NMR (500 MHz, CHLOROFORM-d) δ5.86 (dd, J=17.7, 10.7 Hz, 1H), 5.15 (dd, J=10.7, 0.9 Hz, 1H), 4.98 (dd, J=17.7, 0.8 Hz, 1H), 3.19 (spt, J=7.0 Hz, 1H), 2.92 (dd, J=12.8, 3.6 Hz, 1H), 2.56-2.43 (m, 2H), 2.27 (d, J=18.4 Hz, 1H), 2.13 (d, J=18.4 Hz, 1H), 2.10-2.05 (m, 1H), 2.01-1.82 (m, 4H), 1.23 (d, J=6.9 Hz, 3H), 1.22 (d, J=6.9 Hz, 3H), 1.10 (s, 3H), 1.09 (s, 3H), 1.64-1.07 (m, 11H), 1.04 (s, 3H), 0.98 (s, 3H), 0.95 (s, 3H).

Step 4. Preparation of (3aS,5aR,5bR,7aR,11aR, 11bR,13aS)-1-isopropyl-5a,5b,8,8,11a-pentamethyl-2-oxo-3a-vinyl-3,3a,4,5,5a,5b,6,7,7a,8,11,11a,11b, 12,13,13a-hexadecahydro-2H-cyclopenta[a]chrysen-9-yltrifluoromethanesulfonate A flask containing a solution of (3aS,5aR,5bR,7aR,11aR, 11bR,13aS)-1-isopropyl-5a,5b,8,8,11a-pentamethyl-3a-vinyl-3a,4,5,5a,5b,6,7,7a,8,10,11,11a,11b,12,13,13a-hexadecahydro-2H-cyclopenta[a]chrysene-2,9(3H)-dione (1.15 g, 2.55 mmol) and N,N-bis(trifluoromethylsulfonyl)aniline (1.094 g, 3.06 mmol) in THF (20 mL) was cooled to −78° C. To the cooled solution was added LiHMDS (1M in THF) (5.61 mL, 5.61 mmol). The mixture was stirred for 1 h at −78° C., then was removed from the ice bath and warmed to rt and monitored by TLC. After 45 minutes, TLC showed only a trace of starting material remaining. The mixture was diluted with sat. aq. ammonium chloride solution (40 mL) and extracted with ethyl acetate (3×30 mL). The organic layers were washed with brine, dried over magnesium sulfate, filtered, and concentrated under reduced pressure. The residue was purified by flash chromatography using a 0-8% acetone in hexanes gradient and an 80 g silica gel column. The residue was purified again by flash chromatography using a 0-7% acetone in hexanes gradient to give the title compound (1.02 g, 1.750 mmol, 69% yield) as a white foam. $^1$H NMR (500 MHz, CHLOROFORM-d) δ5.86 (dd, J=17.7, 10.6 Hz, 1H), 5.60 (dd, J=6.8, 2.0 Hz, 1H), 5.16 (dd, J=10.6, 0.8 Hz, 1H), 4.98 (dd, J=17.7, 0.8 Hz, 1H), 3.19 (spt, J=6.9 Hz, 1H), 2.92 (dd, J=12.8, 3.4 Hz, 1H), 2.31-2.21 (m, 2H), 2.13 (d, J=18.6 Hz, 1H), 2.10-2.05 (m, 1H), 2.01-1.81 (m, 4H), 1.23 (d, J=6.9 Hz, 3H), 1.22 (d, J=6.9 Hz, 3H), 1.14 (s, 3H), 1.09 (s, 3H), 1.61-1.07 (m, 10H), 1.04 (s, 3H), 0.99 (s, 3H), 0.95 (s, 3H). $^{19}$F NMR (471 MHz, CHLOROFORM-d) δ-74.79 (s, 1F).

Step 5. To a flask containing (3aS,5aR,5bR,7aR,11aR, 11bR,13aS)-1-isopropyl-5a,5b,8,8,11a-pentamethyl-2-oxo-3a-vinyl-3,3a,4,5,5a,5b,6,7,7a,8,11,11a,11b,12,13,13a-hexadecahydro-2H-cyclopenta[a]chrysen-9-yl trifluoromethanesulfonate (0.1 g, 0.172 mmol) and methyltrioxorhenium(VII) (2.138 mg, 8.58 μmol) was added dichloromethane (2 mL), pyridine (1.665 μl, 0.021 mmol), and

Example 14
Preparation of 4-((3aR,5aR,5bR,7aR,11aS,11bR,13aS)-3a-(2-((2-(dimethylamino)ethyl)amino)-1-hydroxyethyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)benzoic acid
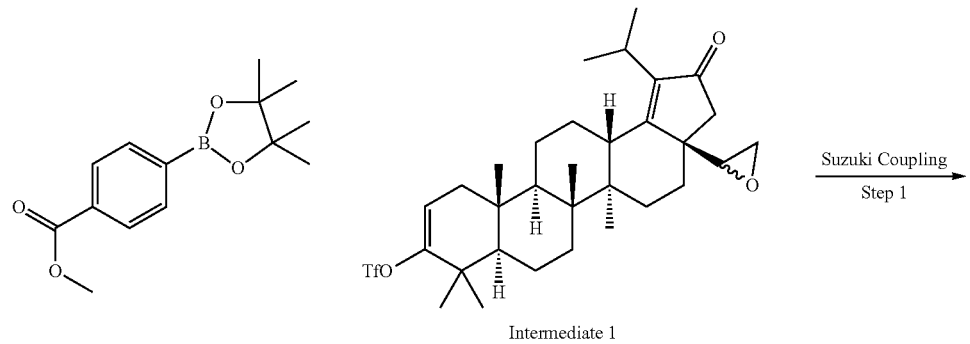
Intermediate 1
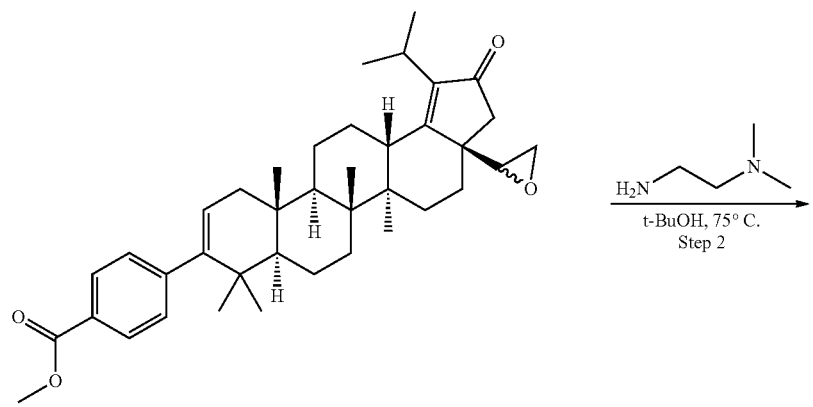
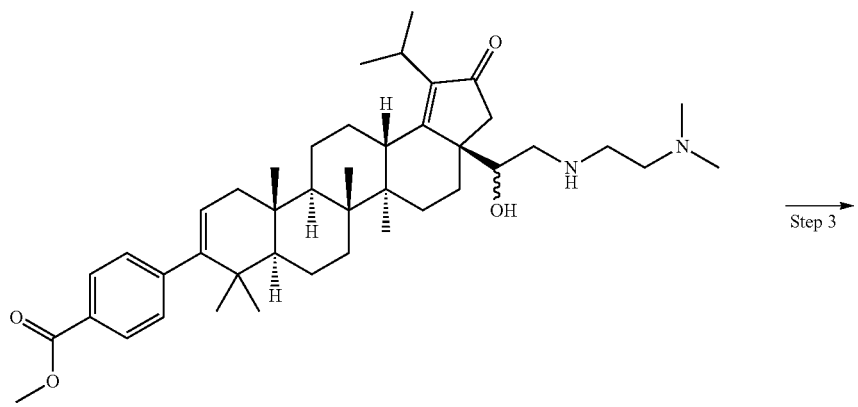

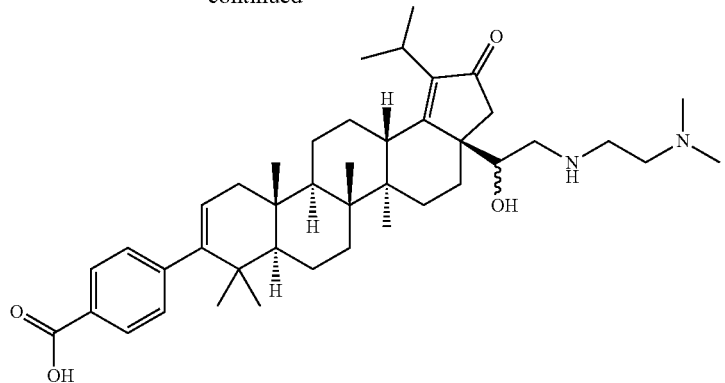

Example 14

Step 1. Preparation of methyl 4-((3aR,5aR,5bR, 7aR,11aS,11bR,13aS)-1-isopropyl-5a,5b,8,8,11a-pentamethyl-3a-(oxiran-2-yl)-2-oxo-3,3a,4,5,5a,5b, 6,7,7a,8,11,11a,11b,12,13,13a-hexadecahydro-2H-cyclopenta[a]chrysen-9-yl)benzoate To a sealable vial containing (3aR,5aR,5bR,7aR,11aR, 11bR,13aS)-1-isopropyl-5a,5b,8,8,11a-pentamethyl-3a-(oxiran-2-yl)-2-oxo-3,3a,4,5,5a,5b,6,7,7a,8,11,11a,11b,12, 13,13a-hexadecahydro-2H-cyclopenta[a]chrysen-9-yl trifluoromethanesulfonate (0.03 g, 0.050 mmol) was added (4-(methoxycarbonyl)phenyl)boronic acid (0.018 g, 0.100 mmol), phosphoric acid, potassium salt (0.032 g, 0.150 mmol), 2-dicyclohexylphosphino-2',6'-dimethoxy-1,1'-biphenyl (S-phos) (1.543 mg, 3.76 µmol), and palladium (II) acetate (0.562 mg, 2.505 µmol). The mixture was diluted with 1,4-dioxane (1 mL) and water (0.2 mL), then was flushed with nitrogen and the vial was sealed and heated to 70° C. After 3 h of heating, the mixture was cooled to rt. The mixture was diluted with water (3 mL) and extracted with dichloromethane (3×4 mL). The organic layers were dried over sodium sulfate, filtered, and concentrated under reduced pressure. The residue was purified by flash chromatography using a 0-20% ethyl acetate in hexanes gradient and a 24 g silica gel column to give the title compound along with minor impurities that were carried to the next step with no additional purification (18 mg total). LC/MS: m/e 585.3 (M+H)+, 2.95 minutes (method 1).

Step 2. Preparation of methyl 4-((3aR,5aR,5bR, 7aR,11aS,11bR,13aS)-3a-(2-((2-(dimethylamino) ethyl)amino)-1-hydroxyethyl)-1-isopropyl-5a,5b,8,8, 11a-pentamethyl-2-oxo-3,3a,4,5,5a,5b,6,7,7a,8,11, 11a,11b,12,13,13a-hexadecahydro-2H-cyclopenta[a] chrysen-9-yl)benzoate To a solution of methyl 4-((3aR,5aR,5bR,7aR,11aS,11bR, 13aS)-1-isopropyl-5a,5b,8,8,11a-pentamethyl-3a-(oxiran-2-yl)-2-oxo-3,3a,4,5,5a,5b,6,7,7a,8,11,11a,11b,12,13,13a-hexadecahydro-2H-cyclopenta[a]chrysen-9-yl)benzoate (0.018 g, 0.031 mmol) in t-BuOH (0.5 mL) was added N,N-dimethylethylenediamine (0.034 mL, 0.308 mmol). The mixture was heated to 75° C. for 9 h and then cooled to rt. The crude reaction mixture was diluted with methanol and purified by prep HPLC (method 1) to give the TFA salt of the title compound (0.008 g, 10.17 ηmol, 33% yield) as a clear film. LC/MS: m/e 673.5 (M+H)+, 1.82 minutes (method 1). $^1$H NMR (500 MHz, CHLOROFORM-d) δ7.96 (d, J=8.4 Hz, 2H), 7.23 (d, J=8.4 Hz, 2H), 5.34 (d, J=4.7 Hz, 1H), 4.67-4.60 (m, 1H), 3.94 (s, 3H), 3.63-3.46 (m, 4H), 3.34-3.23 (m, 2H), 3.19-3.10 (m, 1H), 3.02-2.96 (m, 1H), 2.93 (s, 6H), 2.52-2.42 (m, 1H), 2.22 (dd, J=17.1, 6.2 Hz, 1H), 2.12-2.04 (m, 1H), 1.94-1.71 (m, 5H), 1.07 (s, 3H), 1.00 (s, 3H), 0.98 (s, 3H), 0.95 (s, 3H), 1.67-0.82 (m, 21H).

Step 3. To a solution of methyl 4-((3aR,5aR,5bR,7aR, 11aS,11bR,13aS)-3a-(2-((2-(dimethylamino)ethyl)amino)-1-hydroxyethyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)benzoate, TFA (0.008 g, 10.17 µmol) in 1,4-dioxane (1 mL) was added NaOH (1N) (0.051 mL, 0.051 mmol) and the mixture was heated to 70° C. After 4 h of heating, the mixture was cooled to rt and stirred overnight.

The mixture was again heated to 70° C. for 23.5 h and then, it was cooled to rt. An additional 0.051 mL of 1N NaOH was added and the mixture was heated to 70° C. for 4 h. The mixture was cooled to rt and purified by prep HPLC (method 2) to give the bis TFA salt of 4-((3aR,5aR,5bR, 7aR,11aS,11bR,13aS)-3a-(2-((2-(dimethylamino)ethyl) amino)-1-hydroxyethyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)benzoic acid (0.0043 g, 0.0048 mmol, 47% yield) as a white solid. LC/MS: m/e 659.4 (M+H)−, 1.54 minutes (method 1). $^1$H NMR (500 MHz, Acetic Acid-d4) δ8.04 (d, J=8.4 Hz, 2H), 7.31 (d, J=8.4 Hz, 2H), 5.40 (d, J=4.6 Hz, 1H), 4.77 (d, J=8.5 Hz, 1H), 3.86-3.67 (m, 4H), 3.67-3.58 (m, 1H), 3.35-3.25 (m, 1H), 3.17 (t, J=11.7 Hz, 1H), 3.09 (dd, J=11.6, 3.5 Hz, 1H), 3.03 (s, 6H), 2.58 (d, J=18.8 Hz, 1H), 1.15 (s, 3H), 1.06 (s, 3H), 1.04 (s, 3H), 1.01 (s, 3H), 2.33-0.75 (m, 26H).

Example 15
Preparation of 4-((3aR,5aR,5bR,7aR,11aS,11bR,13aS)-3a-(2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylic acid
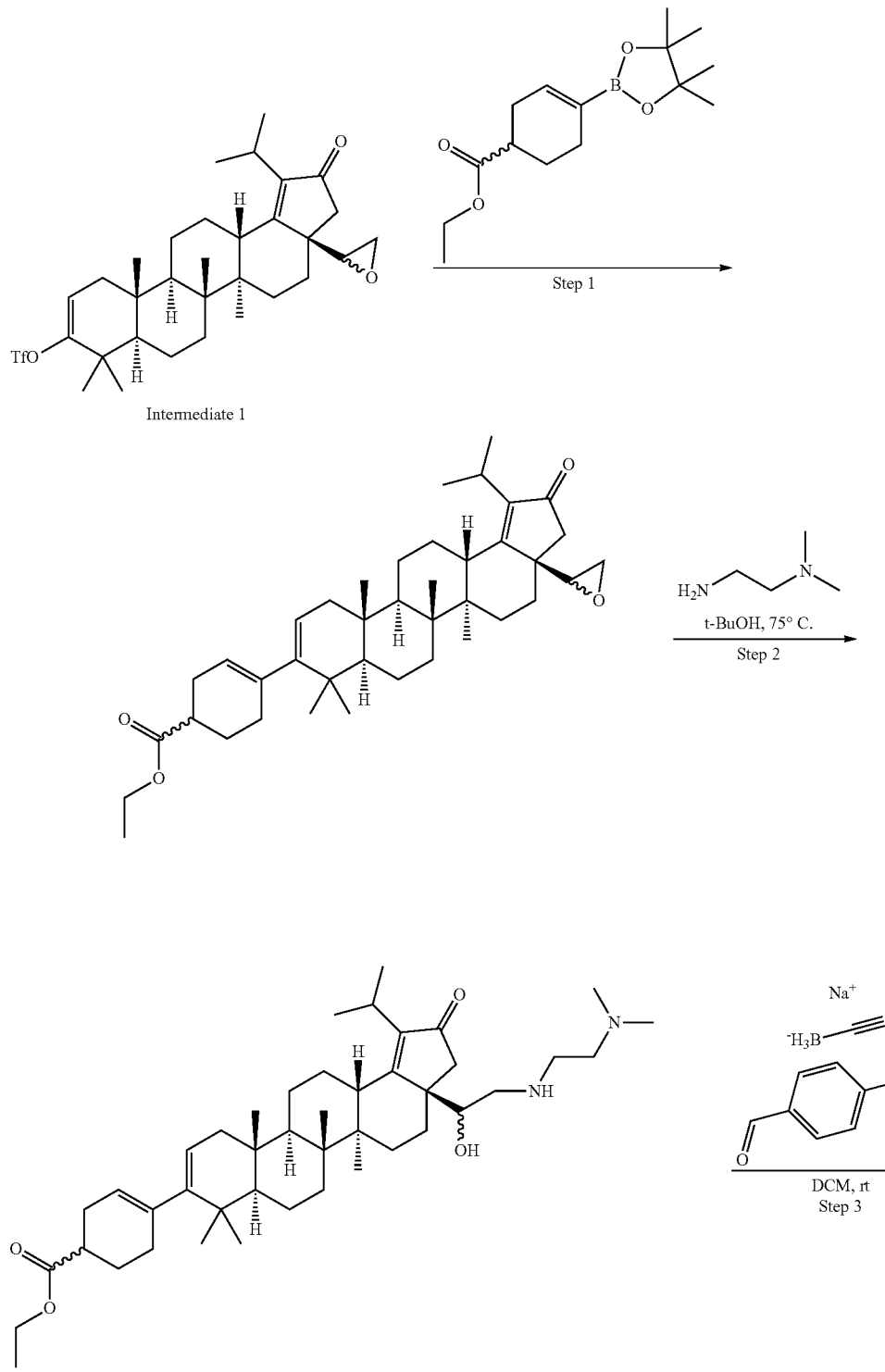

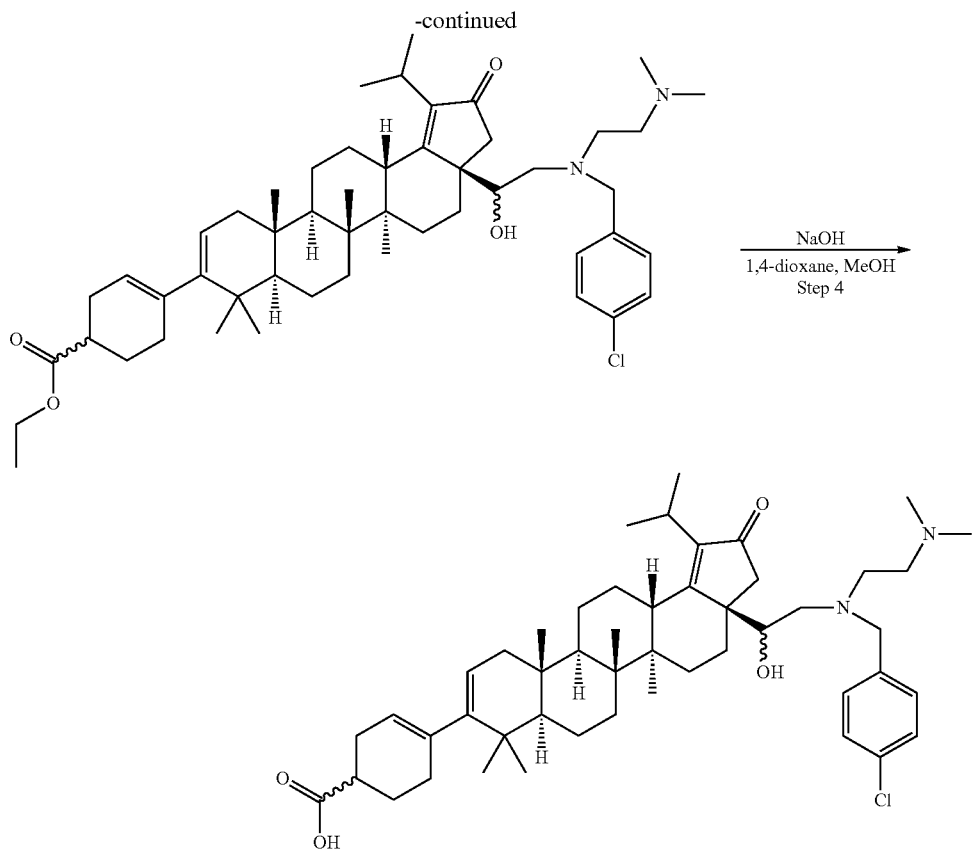

Example 15

Step 1. Preparation of ethyl 4-((3aR,5aR,5bR,7aR, 11aS,11bR,13aS)-1-isopropyl-5a,5b,8,8,11a-pentamethyl-3a-(oxiran-2-yl)-2-oxo-3,3a,4,5,5a,5b,6,7,7a,8, 11,11a, 11b,12,13,13a-hexadecahydro-2H-cyclopenta[a]chrysen-9-yl)cyclohex-3-enecarboxylate To vial containing (3aR,5aR,5bR,7aR,11aR,11bR,13aS)-1-isopropyl-5a,5b,8,8,11a-pentamethyl-3a-(oxiran-2-yl)-2-oxo-3,3a,4,5,5a,5b,6,7,7a,8, 11,11a,11b,12,13,13a-hexadecahydro-2H-cyclopenta[a]chrysen-9-yl trifluoromethanesulfonate (0.07 g, 0.117 mmol) was added ethyl 4-(4,4,5,5-tetramethyl-1,3,2-dioxaborolan-2-yl)cyclohex-3-enecarboxylate (0.033 g, 0.117 mmol), (prepared as described in WO 20131230822), phosphoric acid, potassium salt (0.074 g, 0.351 mmol), palladium (II) acetate (1.312 mg, 5.85 μmol), and 2-dicyclohexylphosphino-2',6'-dimethoxy-1,1'-biphenyl (S-phos) (3.60 mg, 8.77 μmol). The mixture was flushed with nitrogen, then the vial was sealed and heated to 65-70° C. After 10 h of heating, the mixture was cooled to rt. The mixture was diluted with water (7 mL) and extracted with dichloromethane (3×10 mL). The organic layers were dried over sodium sulfate, filtered, and concentrated under reduced pressure. The residue was purified by flash chromatography using a 0-25% EtOAc in hexanes gradient and a 12 g silica gel column to give 0.057 g of the title compound as a mixture of isomers. LC/MS: m/e 603.5 (M+H)+, 3.28 minutes (method 1).

Step 2: Preparation of ethyl 4-((3aR,5aR,5bR,7aR, 11aS,11bR,13aS)-3a-(2-((2-(dimethylamino)ethyl) amino)-1-hydroxyethyl)-1-isopropyl-5a,5b,8,8,11a-pentamethyl-2-oxo-3,3a,4,5,5a,5b,6,7,7a,8,11,11a, 11b,12,13,13a-hexadecahydro-2H-cyclopenta[a] chrysen-9-yl)cyclohex-3-enecarboxylate To a solution of ethyl 4-((3aR,5aR,5bR,7aR,11aS,11bR, 13aS)-1-isopropyl-5a,5b,8,8,11a-pentamethyl-3a-(oxiran-2-yl)-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate (0.057 g, 0.095 mmol) in t-BuOH (1 mL) was added N,N-dimethylethylenediamine (0.104 mL, 0.945 mmol) and the mixture was heated to 75° C. After 23 h of heating, the mixture was cooled to rt, diluted with methanol, and purified by prep HPLC (method 2). The fractions containing the product were combined and concentrated under reduced pressure. The residue was dissolved with dichloromethane (15 mL) and washed with sat. aq. NaHCO₃. The organic layer was dried over sodium sulfate, filtered, and concentrated under reduced pressure to give the diastereomeric mixture of the title compound (0.029 g, 0.042 mmol, 44% yield) as a clear, colorless film. LC/MS: m/e 691.6 (M+H)+, 1.90 minutes (method 1).

Step 3. Preparation of ethyl 4-((3aR,5aR,5bR,7aR, 11aS,11bR,13aS)-3a-(2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b, 6,7,7a,8,11,11a,11b,12,13,13a-hexadecahydro-2H-cyclopenta[a]chrysen-9-yl)cyclohex-3-enecarboxylate To a solution of ethyl 4-((3aR,5aR,5bR,7aR,11aS,11bR, 13aS)-3a-(2-((2-(dimethylamino)ethyl)amino)-1-hydroxyethyl)-1-isopropyl-5a,5b,8,8,11a-pentamethyl-2-oxo-3,3a,4, 5,5a,5b,6,7,7a,8,11,11a,11b,12,13,13a-hexadecahydro-2H-cyclopenta[a]chrysen-9-yl)cyclohex-3-enecarboxylate (0.029 g, 0.042 mmol) in dichloromethane (1 mL) was added 4-cyanobenzaldehyde (8.25 mg, 0.063 mmol) followed by sodium cyanoborohydride (5.27 mg, 0.084 mmol). The mixture was stirred at rt t for 16 h, then an additional 4 mg of 4-cyanobenzaldehyde followed by 5 mg of sodium cyanoborohydride were added to the mixture. The mixture was stirred at rt for 5 h and then diluted with water (10 mL) and extracted with dichloromethane (3×10 mL). The organic layers were dried over sodium sulfate, filtered, and concentrated under reduced pressure. The residue was purified by prep HPLC (method 1) to give the bis TFA salt of the diasteromeric mixture of the title compound (0.015 g, 0.014 mmol, 34% yield) as a clear, colorless film. LC/MS: m/e 815.6 (M+H)$^+$, 2.30 minutes (method 1).

Step 4. To a solution of ethyl 4-((3aR,5aR,5bR,7aR,11aS, 11bR,13aS)-3a-(2-((4-chlorobenzyl)(2-(dimethylamino) ethyl)amino)-1-hydroxyethyl)-1-isopropyl-5a,5b,8,8,11a-pentamethyl-2-oxo-3,3a,4,5,5a,5b,6,7,7a,8,11,11a,11b,12, 13,13a-hexadecahydro-2H-cyclopenta[a]chrysen-9-yl) cyclohex-3-enecarboxylate, 2 TFA (0.015 g, 0.014 mmol) in 1,4-dioxane (1 mL) and methanol (0.5 mL) was added sodium hydroxide (1N) (0.092 mL, 0.092 mmol). The mixture was heated to 75° C. for 16 h then was cooled to rt and was purified by prep HPLC (method 1) to give the bis TFA salt of 4-((3aR,5aR,5bR,7aR,11aS,11bR,13aS)-3a-(2-((4-chlorobenzyl)(2-(dimethylamino)ethyl)amino)-1-hydroxyethyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylic acid (0.007 g, 6.89 μmol, 49% yield) as a white film. LC/MS: m/e 787.6 (M+H)$^+$, 1.90 minutes (method 1). Some of the characteristic chemical shifts of the diasteromeric mixture are as follows: $^1$H NMR (500 MHz, Acetic Acid-d4) δ7.66-7.61 (m, 1.25 H), 7.59-7.55 (m, 0.75H), 7.52-7.47 (m, 2H), 5.40 (br. s., 1H), 5.25 (d, J=6.0 Hz, 1H), 4.58-4.52 (m, 1H), 4.44-4.20 (m, 2H), 2.99 (s, 2.25H), 2.94 (s, 3.75H).

Example 16

Preparation of (S)-4-((3aR,5aR,5bR,7aR,11aS,11bR, 13aS)-3a-(((3-(1,1-dioxidothiomorpholino)propyl) amino)methyl)-1-isopropyl-5a,5b,8,8,11a-pentamethyl-2-phenyl-4,5,5a,5b,6,7,7a,8,11,11a,11b,12,13, 13a-tetradecahydro-3aH-cyclopenta[a]chrysen-9-yl)-1-(fluoromethyl)cyclohex-3-enecarboxylic acid

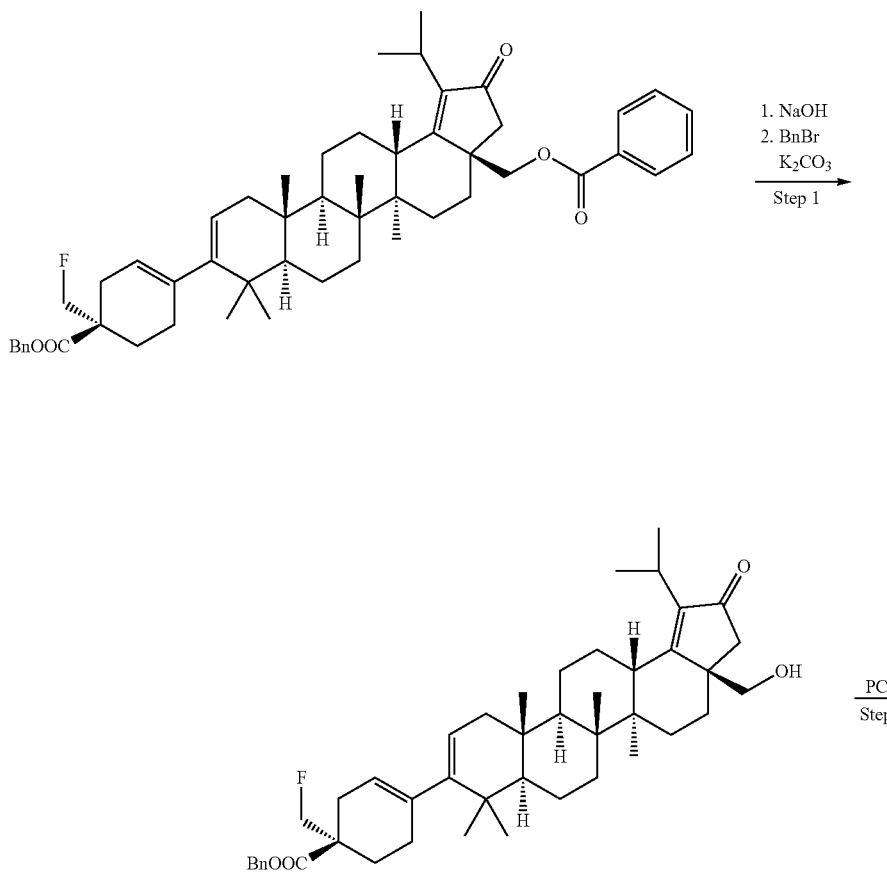

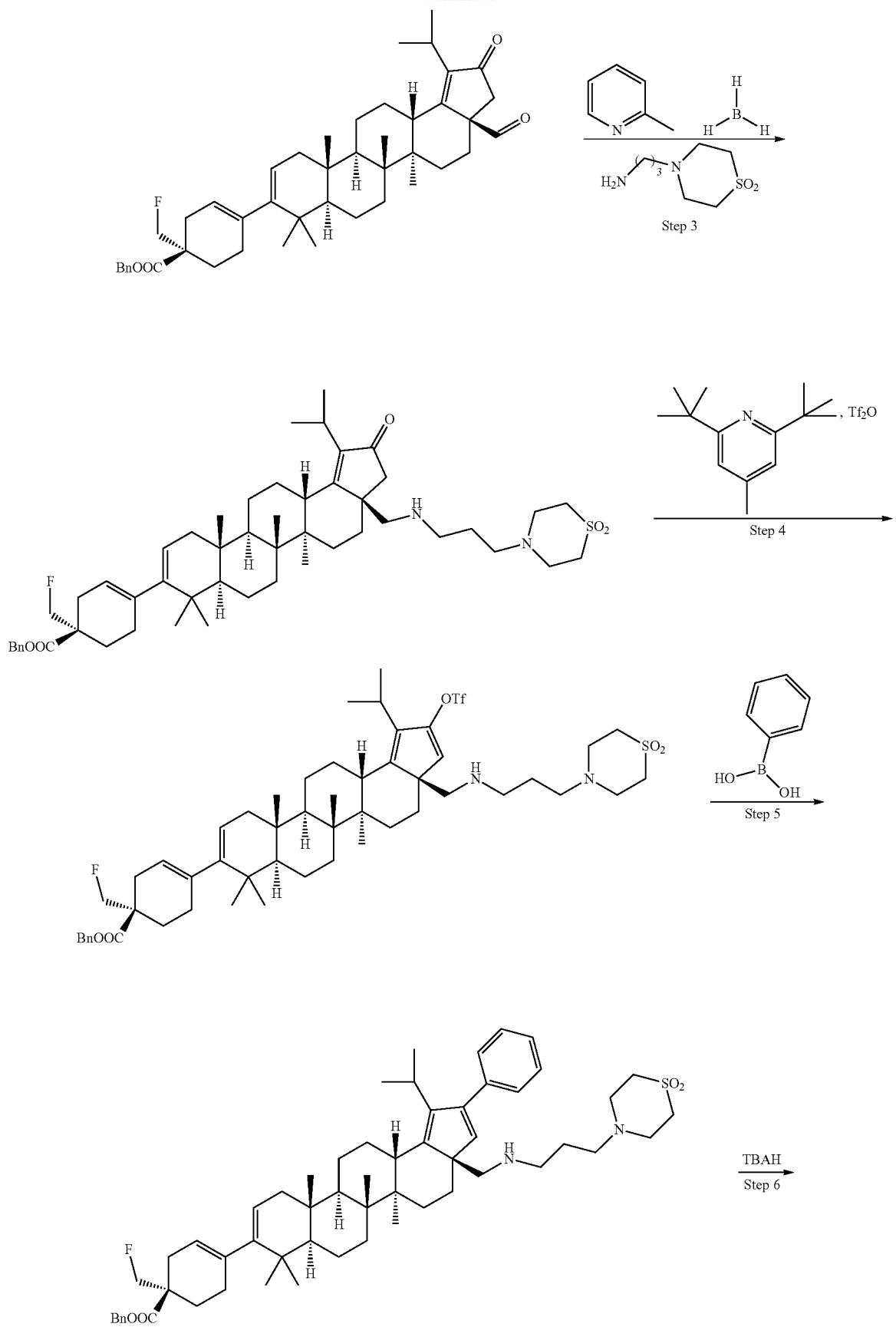

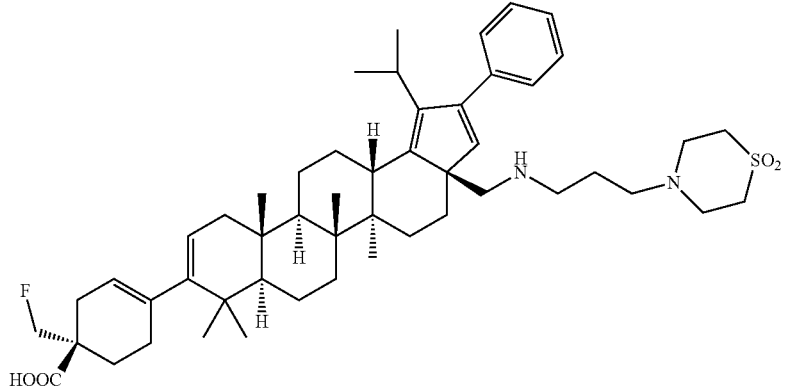

Example 16

Step 1. Preparation of (S)-benzyl 1-(fluoromethyl)-4-((3aR,5aR,5bR,7aR,11aS,11bR,13aS)-3a-(hydroxymethyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate A mixture of ((3aR,5aR,5bR,7aR,11aS,11bR,13aS)-9-((S)-4-((benzyloxy)carbonyl)-4-(fluoromethyl)cyclohex-1-en-1-yl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-3a-yl)methyl benzoate (350 mg, 0.444 mmol) and sodium hydroxide (2.218 mL, 2.218 mmol) in THF (6 mL), water (3 mL) and MeOH (3 mL) was stirred at 20° C. for 15 h. The reaction mixture was quenched with distilled water (10 mL) and extracted with ethyl acetate (3×10 mL). The organic phases were dried over sodium sulfate, filtered and concentrated under reduced pressure to provide the crude intermediate.

To this crude in DMF (8 mL) was added potassium carbonate (184 mg, 1.331 mmol) and benzyl bromide (0.079 mL, 0.665 mmol). The reaction mixture were stirred for 36 h. The reaction mixture was quenched with 10 mL distilled water and extracted with ethyl acetate (3×10 mL). The organic phases were dried over sodium sulfate, filtered and concentrated under reduced pressure. The crude was purified in silica gel with 0-47% ethyl acetate/hexanes to provide the desired product as a white solid (200 mg, 66%). LCMS: m/e 685.7 (M+H)+, 3.03 min (method 1).

Step 2. Preparation of (S)-benzyl 1-(fluoromethyl)-4-((3aR,5aR,5bR,7aR,11aS,11bR,13aS)-3a-formyl-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate (S)-benzyl 1-(fluoromethyl)-4-((3aR,5aR,5bR,7aR,11aS,11bR,13aS)-3a-(hydroxymethyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate (200 mg, 0.292 mmol) was dissolved in dichloromethane (8 mL) and pyridinium chlorochromate (126 mg, 0.584 mmol) was added and the mixture was stirred at room temperature for 3 h. The reaction mixture was concentrated under reduced pressure and the residue was purified in silica gel with 0-45% ethyl acetate/hexanes to provide the desired product as a white solid (180 mg, 90%). LCMS: m/e 683.7 (M+H)+, 3.50 min (method 1).

Step 3. Preparation of (S)-benzyl 4-((3aR,5aR,5bR,7aR,11aS,11bR,13aS)-3a-(((3-(1,1-dioxidothiomorpholino)propyl)amino)methyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate A mixture of(S)-benzyl 1-(fluoromethyl)-4-((3aR,5aR,5bR,7aR,11aS,11bR,13aS)-3a-formyl-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)cyclohex-3-enecarboxylate (180 mg, 0.264 mmol), 4-(3-aminopropyl)thiomorpholine 1,1-dioxide (65.9 mg, 0.343 mmol) and borane-2-methylpyridine complex (56.4 mg, 0.527 mmol) in methanol (4 mL) and acetic acid (1 mL) was stirred at 20° C. for 18 h. The reaction mixture was concentrated under reduced pressure and the residue was purified in silica gel with 0-90% acetone/dichloromethane to provide the desired product as a pale yellow solid (190 mg, 84%). LCMS: m/e 859.9 (M+H)+, 2.20 min (method 1).

Step 4. Preparation of (S)-benzyl 4-((3aR,5aR,5bR,7aR,11aS,11bR,13aS)-3a-(((3-(1,1-dioxidothiomorpholino)propyl)amino)methyl)-1-isopropyl-5a,5b,8,8,11a-pentamethyl-2-(((trifluoromethyl)sulfonyl)oxy)-4,5,5a,5b,6,7,7a,8,11,11a,11b,12,13,13a-tetradecahydro-3aH-cyclopenta[a]chrysen-9-yl)-1-(fluoromethyl)cyclohex-3-enecarboxylate To a solution of (S)-benzyl 4-((3aR,5aR,5bR,7aR,11aS,11bR,13aS)-3a-(((3-(1,1-dioxidothiomorpholino)propyl)amino)methyl)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate (190 mg, 0.221 mmol) in 1,2-dichloroethane (6 mL) was added 2,6-di-tert-butyl-4-methylpyridine (114 mg, 0.553 mmol) followed by trifluoromethanesulfonic anhydride (0.112 mL, 0.663 mmol) at 0° C. The reaction mixture was stirred for 15 hours at room temperature, then quenched with sat. sodium bicarbonate (5 mL) and extracted with dichloromethane (3×4 mL). The combined organic phases were washed with brine, dried over sodium sulfate, filtered and concentrated under reduced pressure. The residue was purified in silica gel with 0-80% ethyl acetate/hexanes to provide the product as colorless oil (100 mg, 46%). LCMS: m/e 991.9 (M+H)+, 2.54 min (method 1).

Step 5. Preparation of (S)-benzyl 4-((3aR,5aR,5bR, 7aR,11aS,11bR,13aS)-3a-(((3-(1,1-dioxidothiomorpholino)propyl)amino)methyl)-1-isopropyl-5a,5b,8, 8,11a-pentamethyl-2-phenyl-4,5,5a,5b,6,7,7a,8,11, 11a,11b,12,13,13a-tetradecahydro-3aH-cyclopenta [a]chrysen-9-yl)-1-(fluoromethyl)cyclohex-3-enecarboxylate A mixture of (S)-benzyl 4-((3aR,5aR,5bR,7aR,11aS, 11bR,13aS)-3a-(((3-(1,1-dioxidothiomorpholino)propyl) amino)methyl)-1-isopropyl-5a,5b,8,8,11a-pentamethyl-2- (((trifluoromethyl)sulfonyl)oxy)-4,5,5a,5b,6,7,7a,8,11,11a, 11b,12,13,13a-tetradecahydro-3aH-cyclopenta[a]chrysen-9- yl)-1-(fluoromethyl)cyclohex-3-enecarboxylate (80 mg, 0.081 mmol), phenylboronic acid (11.81 mg, 0.097 mmol), tetrakis(triphenylphosphine)palladium (4.66 mg, 4.04 µmol) and sodium bicarbonate 33.9 mg, 0.404 mmol) in toluene (4 mL) and water (2 mL) was heated up at 80° C. for 3 hours. The reaction mixture was quenched with water (6 mL) and extracted with ethyl acetate (3×8 mL). The combined organic phases were washed with brine and dried over sodium sulfate, filtered and concentrated under reduced pressure. The residue was purified in silica gel with 0-20% ethyl acetate/hexanes to provide the title compound as a colorless oil (40 mg, 52%). LCMS: m/e 919.9 (M+H)$^+$, 2.52 min (method 1).

Step 6. A mixture of (S)-benzyl 4-((3aR,5aR,5bR,7aR, 11aS,11bR,13aS)-3a-(((3-(1,1-dioxidothiomorpholino)propyl)amino)methyl)-1-isopropyl-5a,5b,8,8,11a-pentamethyl- 2-phenyl-4,5,5a,5b,6,7,7a,8,11,11a,11b,12,13,13a-tetradecahydro-3aH-cyclopenta[a]chrysen-9-yl)-1- (fluoromethyl)cyclohex-3-enecarboxylate (15 mg, 0.016 mmol) and tetrabutylammonium hydroxide (30.8 mg, 0.065 mmol) in tetrahydrofuran (1 mL) and water (0.3 mL) was stirred at 20° C. for 3 h. The reaction mixture was concentrated under reduced pressure and the residue was purified by prep. HPLC with 0-80 acetonitrile/water/TFA in Phenomenex Luna C18 30×100 S10 to provide (S)-4-((3aR,5aR, 5bR,7aR,11aS,11bR,13aS)-3a-(((3-(1,1-dioxidothiomorpholino)propyl)amino)methyl)-1-isopropyl-5a,5b,8,8,11a- pentamethyl-2-phenyl-4,5,5a,5b,6,7,7a,8,11,11a,11b,12,13, 13a-tetradecahydro-3aH-cyclopenta[a]chrysen-9-yl)-1- (fluoromethyl)cyclohex-3-enecarboxylic acid as a white solid (2.5 mg, 18%). LCMS: m/e 829.60 (M+H)$^+$, 2.78 min (method 1). $^1$H NMR (Acetone) δ: 7.24-7.48 (m, 5H), 6.24 (s, 1H), 5.38 (br. s., 1H), 5.21-5.32 (m, 1H), 4.58-4.69 (m, 1H), 4.45-4.56 (m, 1H), 3.42-3.56 (m, 2H), 3.22-3.37 (m, 2H), 3.01-3.18 (m, 8H), 2.94 (dd, J=12.6, 3.0 Hz, 1H), 2.72-2.84 (m, 2H), 2.60 (d, J=16.4 Hz, 1H), 1.07-2.42 (m, 24H), 1.29 (s, 3H), 0.95-1.06 (m, 12H), 0.84-0.94 (m, 6H).

Example 17

Preparation of (S)-4-((3aR,5aR,5bR,7aR,11aS,11bR, 13aS)-3a-((2-(1,1-dioxidothiomorpholino)ethyl) amino)-1-isopropyl-5a,5b,8,8,11a-pentamethyl-2- phenyl-4,5,5a,5b,6,7,7a,8,11,11a,11b,12,13,13a- tetradecahydro-3aH-cyclopenta[a]chrysen-9-yl)-1- (fluoromethyl)cyclohex-3-enecarboxylic acid

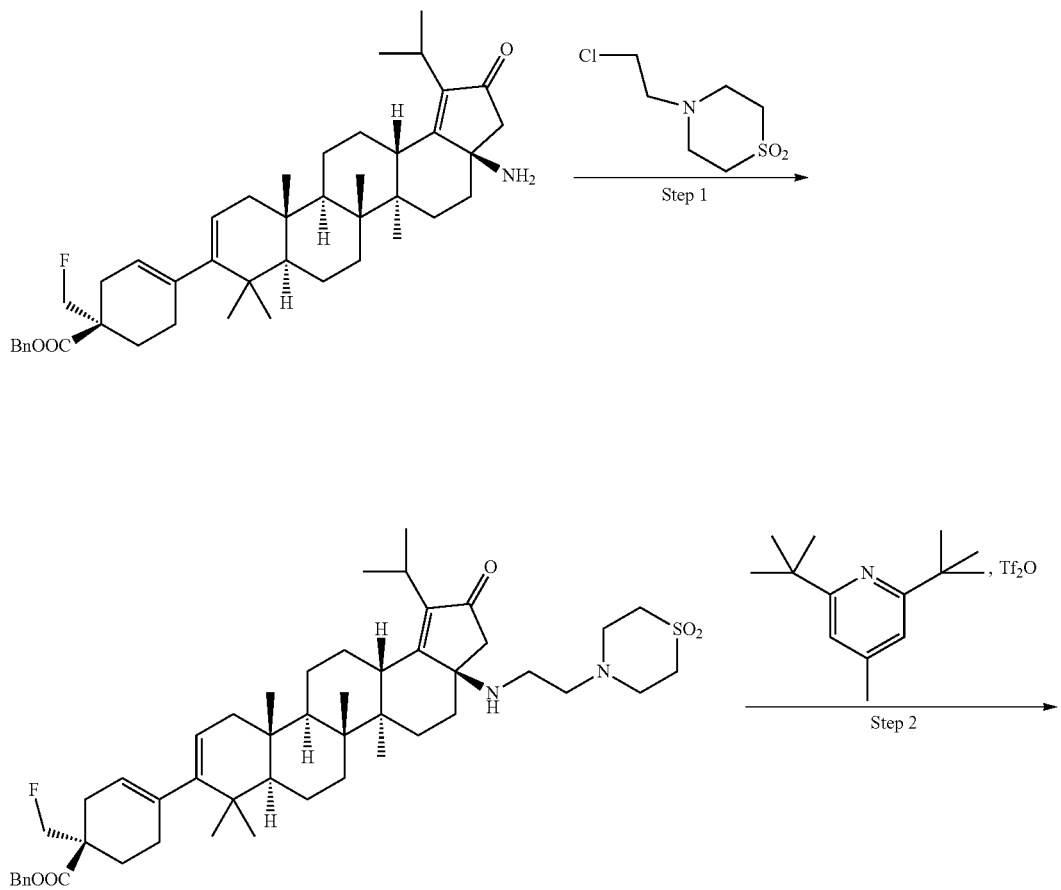

-continued

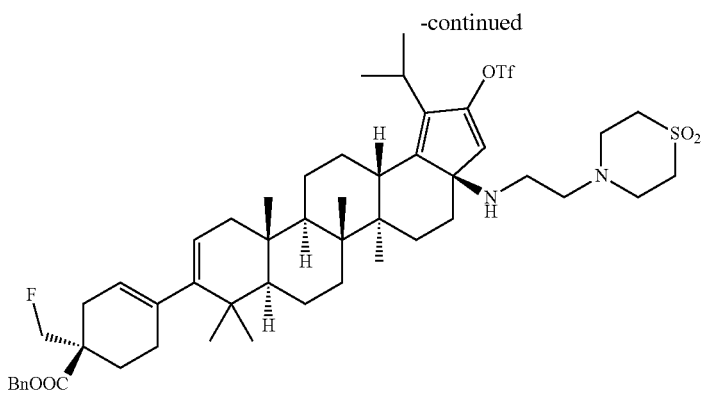

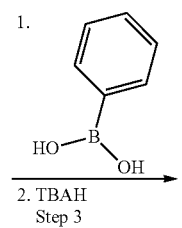

2. TBAH
Step 3

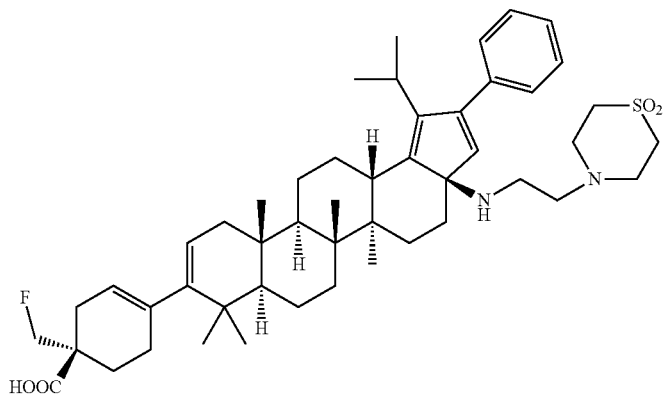

Example 17

Step 1. Preparation of (S)-benzyl 4-((3aR,5aR,5bR, 7aR,11aS,11bR,13aS)-3a-((2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate A mixture of (S)-benzyl 4-((3aR,5aR,5bR,7aR,11aS,11bR,13aS)-3a-amino-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate (320 mg, 0.478 mmol), 4-(2-chloroethyl)thiomorpholine 1,1-dioxide (189 mg, 0.955 mmol), potassium iodide (119 mg, 0.716 mmol) and potassium phosphate (406 mg, 1.911 mmol) in acetonitrile (10 mL) was heated up at 100° C. for 18 h. The reaction mixture was quenched with distilled water (10 mL) and extracted with ethyl acetate (2×15 mL). The combined organic phases were dried over sodium sulfate, filtered and concentrated under reduced pressure. The residue was purified silica gel with 0-40% acetone/dichloromethane to provide the title compound (240 mg, 61%). LCMS: m/e 831.6 (M+H)⁺, 2.22 min (method 1).

Step 2. Preparation of (S)-benzyl 4-((3aR,5aR,5bR, 7aR,11aS,11bR,13aS)-3a-((2-(1,1-dioxidothiomorpholino)ethyl)amino)-1-isopropyl-5a,5b,8,8,11a-pentamethyl-2-(((trifluoromethyl)sulfonyl)oxy)-4,5,5a,5b,6,7,7a,8,11,11a,11b,12,13,13a-tetradecahydro-3aH-cyclopenta[a]chrysen-9-yl)-1-(fluoromethyl)cyclohex-3-enecarboxylate To a solution of (S)-benzyl 4-((3aR,5aR,5bR,7aR,11aS, 11bR,13aS)-3a-((2-(1,1-dioxidothiomorpholino)ethyl)amino)-1-isopropyl-5a,5b,8,8,11a-pentamethyl-2-oxo-3,3a,4,5,5a,5b,6,7,7a,8,11,11a,11b,12,13,13a-hexadecahydro-2H-cyclopenta[a]chrysen-9-yl)-1-(fluoromethyl)cyclohex-3-enecarboxylate (240 mg, 0.289 mmol) in 1,2-dichloroethane (6 mL) was added 2,6-di-tert-butyl-4-methylpyridine (148 mg, 0.722 mmol) followed by trifluoromethanesulfonic anhydride (0.098 mL, 0.577 mmol) at 0° C. The reaction mixture was warmed up to room temperature and then heated up at 70° C. for 1 h. The reaction mixture was quenched with sat. sodium bicarbonate (5 mL) and extracted with dichloromethane (3×4 mL). The combined organic phases were washed with brine and dried over sodium sulfate, filtered and concentrated under reduced pressure. The residue was purified in silica gel with 0-100% ethyl acetate/hexanes to provide the title compound as colorless oil (110 mg, 40%). LCMS: m/e 963.5 (M+H)⁺, 2.42 min (method 1).

Step 3. A mixture of benzyl (S)-4-((3aR,5aR,5bR,7aR, 11aS,11bR,13aS)-3a-((2-(1,1-dioxidothiomorpholino)ethyl)amino)-1-isopropyl-5a,5b,8,8,11a-pentamethyl-2-(((trifluoromethyl)sulfonyl)oxy)-3a,5,5a,5b,6,7,7a,8,11,11a,11b,12,13,13a-tetradecahydro-4H-cyclopenta[a]chrysen-9-yl)-1-(fluoromethyl)cyclohex-3-ene-1-carboxylate (24 mg, 0.025 mmol), phenylboronic acid (3.59 mg, 0.029 mmol), tetrakis(triphenylphosphine)palladium (1.419 mg, 1.228 μmol) and sodium bicarbonate (10.32 mg, 0.123 mmol) in toluene (1 mL) and water (0.5 mL) was heated up at 80° C. for 3. The reaction mixture was quenched with water (2 mL) and extracted with ethyl acetate (3×2 mL). The combined organic phases were washed with brine and dried over sodium sulfate, filtered and concentrated under reduced pressure. The residue was filtered through a pad of silica gel using 50% ethyl acetate/hexanes to provide the intermediate silyl ester as a yellow oil.

The silyl ester intermediate was dissolved in tetrahydrofuran (1 mL) and water (0.3 mL) and treated with tetrabutylammonium hydroxide (25.4 mg, 0.054 mmol). The reaction mixture was stirred at 20° C. for 3 h and then purified by prep. HPLC with 0-80% acetonitrile/water/TFA in Phenomenex Luna C18 30×100 S10 to provide (S)-benzyl 4-((3aR,5aR,5bR,7aR,11aS,11bR,13aS)-3a-(((2-(1,1-dioxidothiomorpholino)ethyl)amino)methyl)-1-isopropyl-5a,5b,8,8,11a-pentamethyl-2-phenyl-4,5,5a,5b,6,7,7a,8,11,11a,11b,12,13,13a-tetradecahydro-3aH-cyclopenta[a]chrysen-9-yl)-1-(fluoromethyl)cyclohex-3-enecarboxylate as a white solid (1.5 mg, 7%). LCMS: m/e 801.8 (M+H)+, 2.15 min (method 1). $^1$H NMR (METHANOL-d4) δ: 7.38-7.47 (m, 3H), 7.28-7.36 (m, 2H), 6.08 (s, 1H), 5.58 (s., 1H), 4.90-4.94 (m, 1H), 4.50-4.63 (m, 1H), 4.38-4.48 (m, 1H), 3.42-3.53 (m, 1H), 3.35-3.39 (m, 1H), 3.07-3.23 (m, 8H), 2.77-2.98 (m, 4H), 2.54-2.66 (m, 2H), 2.44-2.51 (m, 1H), 2.31-2.41 (m, 1H), 1.46-2.21 (m, 18H), 1.45 (s, 3H), 1.43 (s, 3H), 1.20 (s, 3H), 1.14 (s, 3H), 1.05 (d, J=7.1 Hz, 3H), 0.89-0.97 (m, 6H).

HIV Cell Culture Assay—

MT-2 cells and 293T cells were obtained from the NIH AIDS Research and Reference Reagent Program. MT-2 cells were propagated in RPMI 1640 media supplemented with 10% heat inactivated fetal bovine serum, 100 µg/mL penicillin G and up to 100 units/mL streptomycin. The 293T cells were propagated in DMEM media supplemented with 10% heat inactivated fetal bovine serum (FBS), 100 units/mL penicillin G and 100 µg/mL streptomycin. The proviral DNA clone of NL4-3 was obtained from the NIH AIDS Research and Reference Reagent Program. A recombinant NL4-3 virus, in which a section of the nef gene from NL4-3 was replaced with the Renilla luciferase gene, was used as a reference virus. In addition, residue Gag P373 was converted to P373S. Briefly, the recombinant virus was prepared by transfection of the altered proviral clone of NL4-3. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) µL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 1.

Biological Data Key for $EC_{50}$

| Compounds with $EC_{50}$ >0.1 µM | Compounds with $EC_{50}$ ≤0.1 µM |
|---|---|
| Group "B" | Group "A" |

TABLE 1

| Example # | Structure | EC50 (µM) |
|---|---|---|
| 1 | 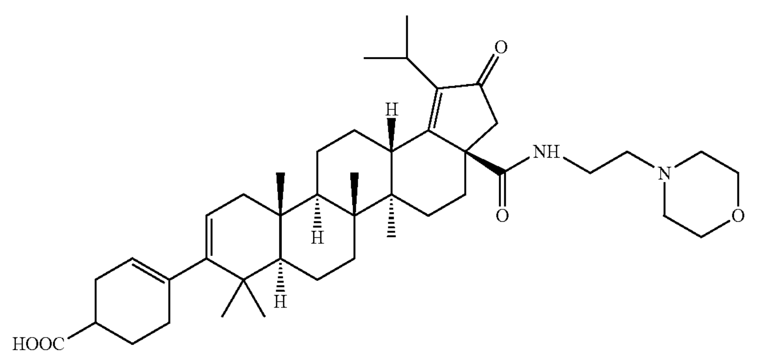 | 1.93E−03 |
| 2 | 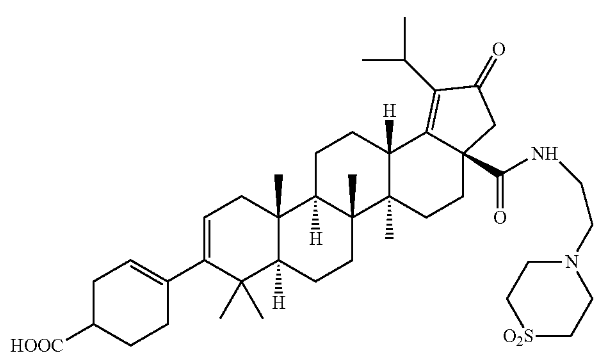 | A |

TABLE 1-continued

| Example # | Structure | EC50 (μM) |
|---|---|---|
| 3 | 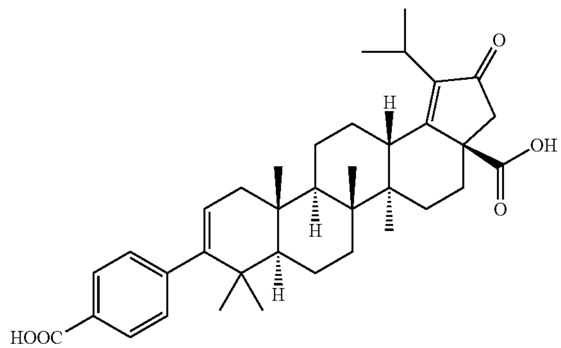 | A |
| 4 | 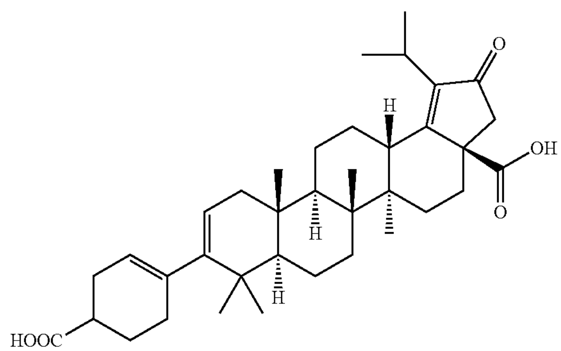 | A |
| 5 | 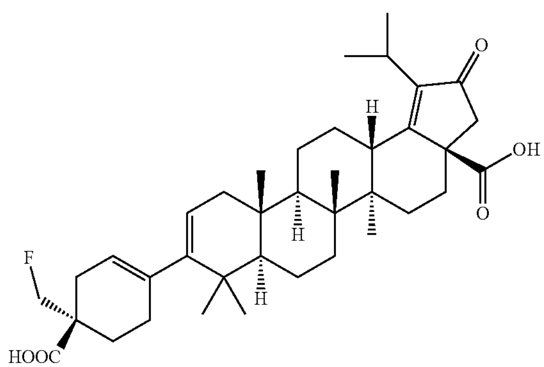 | A |
| 6 | 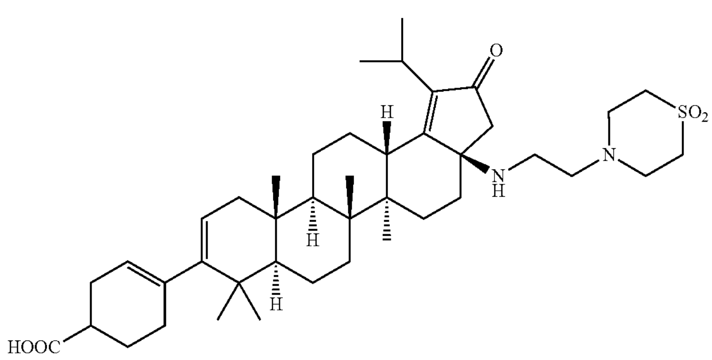 | A |

TABLE 1-continued

| Example # | Structure | EC50 (μM) |
|---|---|---|
| 7 | 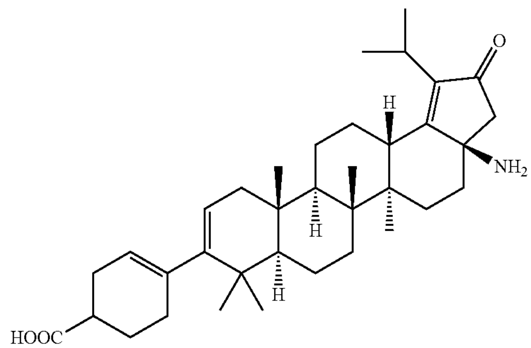 | 9.73E−04 |
| 8 | 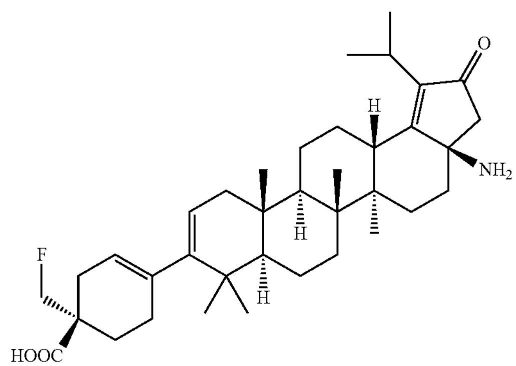 | A |
| 9 | 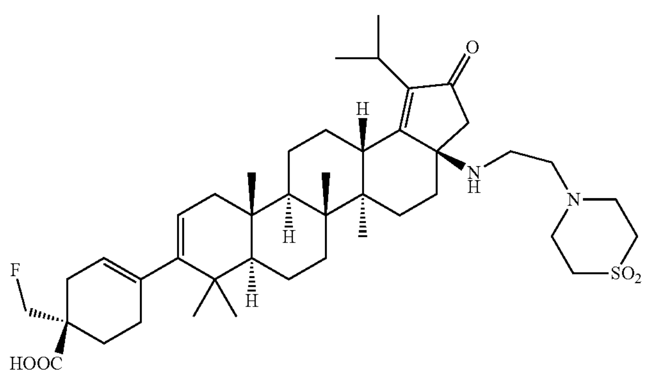 | A |
| 10 | 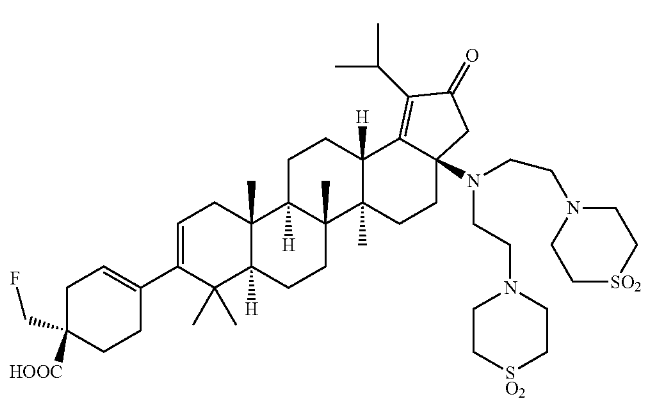 | A |

TABLE 1-continued

| Example # | Structure | EC50 (µM) |
|---|---|---|
| 11 | 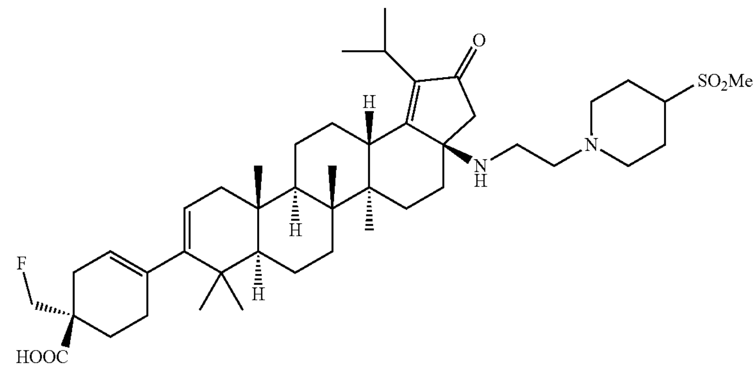 | A |
| 12 | 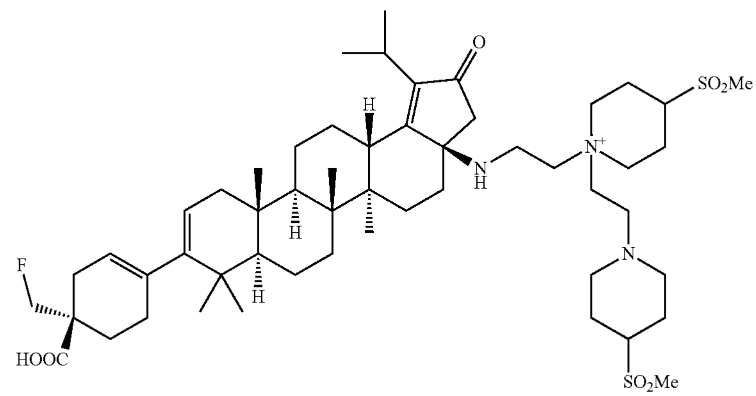 | A |
| 13 | 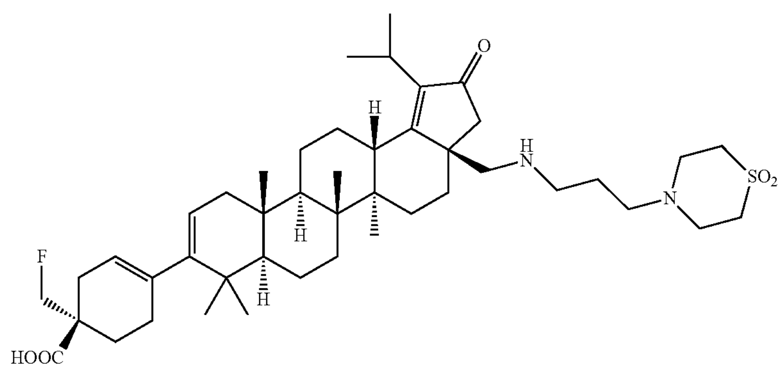 | A |
| 14 | 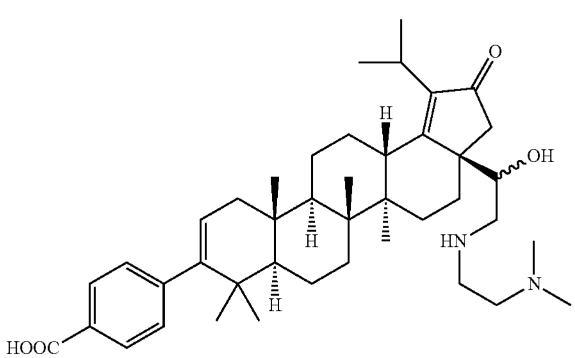 | 5.36E−03 |

TABLE 1-continued

| Example # | Structure | EC50 (µM) |
|---|---|---|
| 15 | 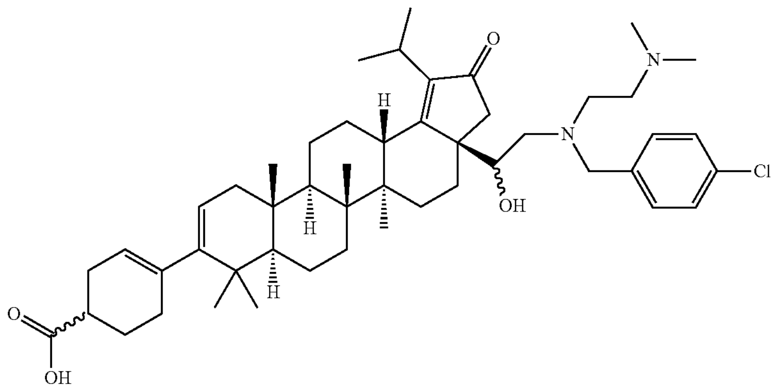 | A |
| 16 | 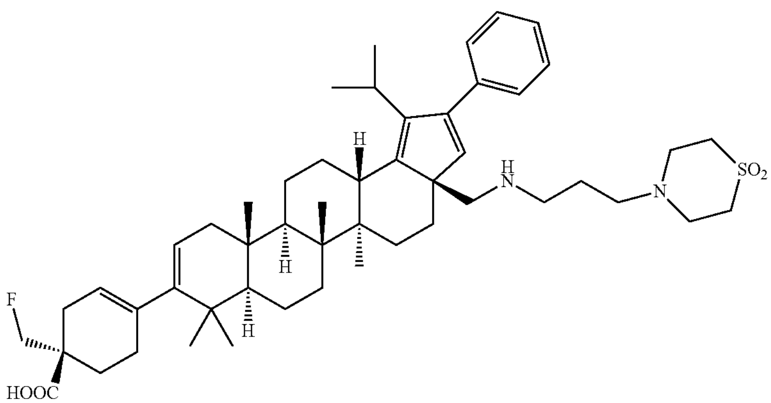 | 2.64E−03 |
| 17 | 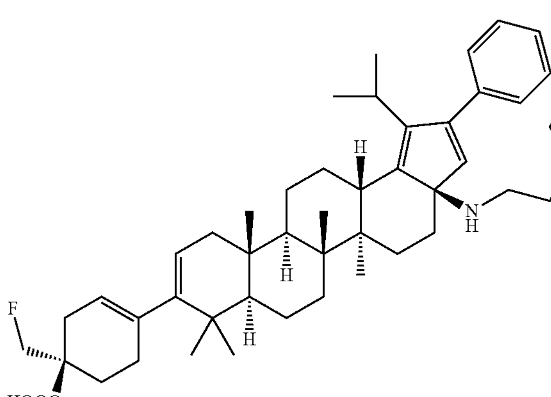 | 10.9E−02 |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound, including pharmaceutically acceptable salts thereof, which is selected from a compound of Formulas I and II:

Formula I

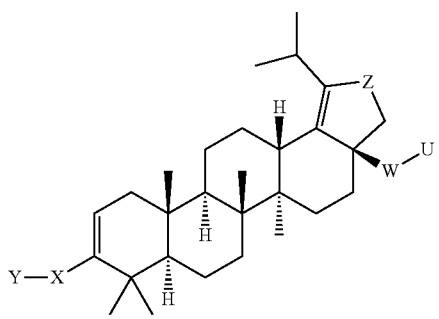

and

Formula II

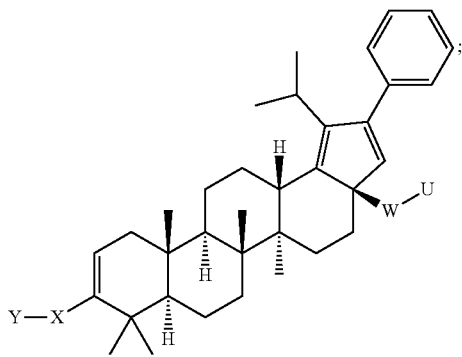

wherein X is selected from the group of phenyl, heteroaryl, $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{6-8}$ dioxacycloalkenyl, $C_{6-9}$ oxaspirocycloalkyl, and $C_{6-9}$ oxaspirocycloalkenyl ring;
and further wherein X is substituted with A, wherein A is at least one member selected from the group of —H, -halo, -hydroxyl, —$C_{1-6}$ alkyl, —$C_{1-6}$ alkoxy, —$C_{1-6}$ haloalkyl, —CN, —$NR_8R_9$, —$COOR_2$, —$CONR_2R_2$ and —$C_{1-6}$ alkyl-Q;
Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;
$R_2$ is —H, —$C_{1-6}$ alkyl, -alkylsubstituted $C_{1-6}$ alkyl or -arylsubstituted $C_{1-6}$ alkyl;
Y is selected from the group of $COOR_2$, —$C(O)NR_2SO_2R_3$, —$C(O)NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkyl substituted $C_{1-6}$ alkyl, —$COOR_2$, $CF_2$—$COOR_2$, —$NHC(O)(CH_2)_n$—$COOR_2$, —$SO_2NR_2C(O)R_2$, -tetrazole, and —CONHOH, wherein n=1-6;
$R_3$ is H, —$C_{1-6}$ alkyl or -alkylsubstituted $C_{1-6}$ alkyl;
W is absent, or is —CO— or is selected from the group of
—$C_{2-6}$ alkyl-, —$C_{2-6}$ alkyl-CO—, —$C_{2-6}$ alkenyl-, —$C_{2-6}$ alkenyl-CO—, and -heteroaryl-; or is selected from the group of:

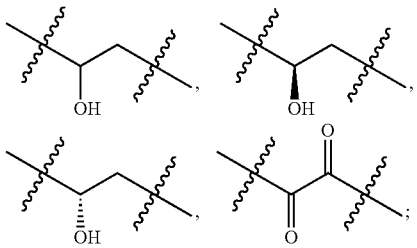

U is selected from —$NR_4R_5$ and $OR_2$,
with the proviso that U cannot be $OR_2$ when W is absent;
Z is selected from the group of CO—, —CHOH, —C=N—$OR_2$, —C=N—$R_{24}$ and CH—$NHR_{24}$;
$R_4$ is selected from the group of —H, —$C_{1-6}$ alkyl, —$C_{1-6}$ alkyl-$C(OR_3)_2$—$C_{3-6}$ cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, and —$SO_2NR_2R_2$;
$Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;
$R_5$ is selected from the group of —H, —$C_{1-6}$ alkyl, —$C_{3-6}$ cycloalkyl, —$C_{1-6}$ alkylsubstituted alkyl, —$C_{1-6}$ alkyl-$NR_8R_9$, —$COR_{10}$, —$COCOR_6$, —$SO_2R_7$ and —$SO_2NR_2R_2$;
with the proviso that $R_4$ or $R_5$ cannot be $COR_6$ or $COCOR_6$ when W is CO,
and with the further proviso that only one of $R_4$ or $R_5$ can be selected from the group of —$COR_6$, —$COCOR_6$, —$SO_2R_7$ and —$SO_2NR_2R_2$;
$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substitutedalkyl-$Q_2$, —$C_{3-6}$ cycloalkyl-$Q_2$, aryl-$Q_2$, —$NR_{13}R_{14}$, and —$OR_{15}$;
$Q_2$ is selected from the group of aryl, heteroaryl, substituted heteroaryl, —$OR_2$, —$COOR_2$, —$NR_8R_9$, $SO_2R_7$, —$CONHSO_2R_3$, and —$CONHSO_2NR_2R_2$;
$R_7$ is selected from the group of —H, —$C_{1-6}$ alkyl, —$C_{1-6}$ substituted alkyl, —$C_{3-6}$ cycloalkyl, —$CF_3$, aryl, and heteroaryl;
$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —$COOR_3$,
or $R_8$ and $R_9$ are taken together with the adjacent N to form a cycle selected from the group of:

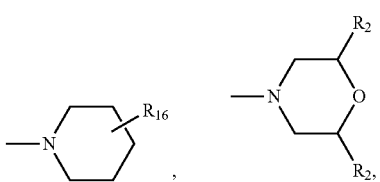

-continued

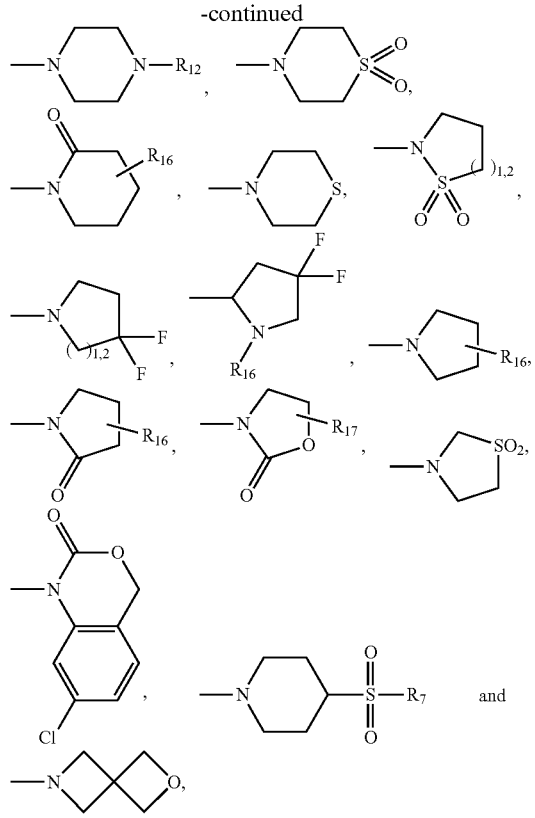

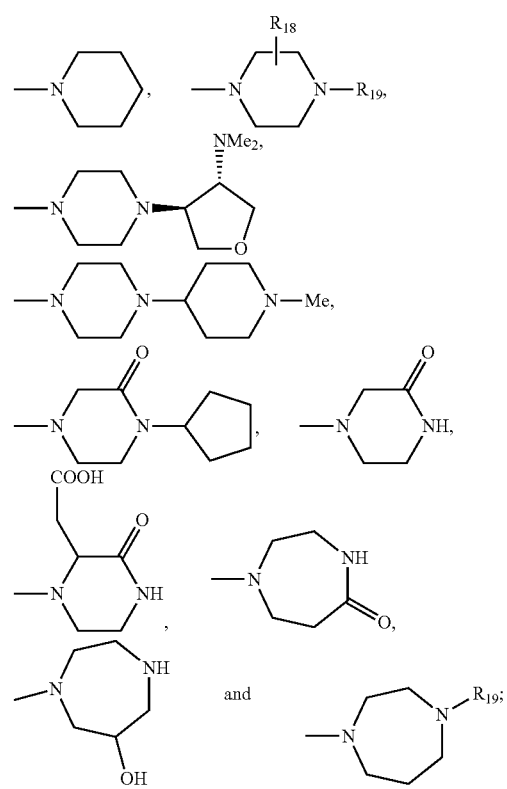

with the proviso that only one of $R_8$ or $R_9$ can be —COOR$_3$;

$R_{10}$ and $R_{11}$ are independently selected from the group of —H, —C$_{1-6}$ alkyl, —C$_{1-6}$ substituted alkyl and —C$_{3-6}$ cycloalkyl, or $R_{10}$ and $R_{11}$ are taken together with the adjacent N to form the cycle

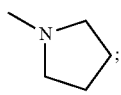

$R_{12}$ is selected from the group of —H, —C$_{1-6}$ alkyl, —C$_{1-6}$ alkyl-OH; —C$_{1-6}$ alkyl, —C$_{1-6}$ substituted alkyl, —C$_{3-6}$ cycloalkyl, —COR$_7$, —COONR$_{22}$R$_{23}$, —SOR$_7$, and —SONR$_{24}$R$_{25}$;

$R_{13}$ and $R_{14}$ are independently selected from the group of —H, —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$, C$_{1-6}$ substituted alkyl-Q$_3$ and

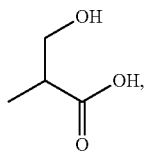

or $R_{13}$ and $R_{14}$ are taken together with the adjacent N to form a cycle selected from the group of:

$Q_3$ is selected from the group of heteroaryl, substituted heteroaryl, —NR$_{20}$R$_{21}$, ⁻CONR$_2$R$_2$, —COOR$_2$, —OR$_2$, and —SO$_2$R$_3$;

$R_{15}$ is selected from the group of —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$ and —C$_{1-6}$ substituted alkyl-Q$_3$;

$R_{16}$ is selected from the group of —H, —C$_{1-6}$ alkyl, —NR$_2$R$_2$, and —COOR$_3$;

$R_{17}$ is selected from the group of —H, —C$_{1-6}$ alkyl, —COOR$_3$, and aryl;

$R_{18}$ is selected from the group of H, —COOR$_2$ and —C$_{1-6}$ alkyl-COOR$_2$;

$R_{19}$ is selected from the group of —H, —C$_{1-6}$ alkyl, —C$_{1-6}$ alkyl-Q$_4$, —COR$_3$, and —COOR$_3$;

$Q_4$ is selected from the group of —NR$_2$R$_2$ and —OR$_2$;

$R_{20}$ and $R_{21}$ are independently selected from the group of —H, —C$_{1-6}$ alkyl, —C$_{1-6}$ substituted alkyl, —C$_{1-6}$ substituted alkyl-OR$_2$, and —COR$_3$, or $R_{20}$ and $R_{21}$ are taken together with the adjacent N to form a cycle selected from the group of

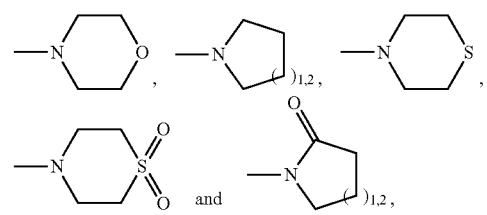

with the proviso that only one of $R_{20}$ or $R_{21}$ can be —COR$_3$, $R_{22}$ and $R_{23}$ are independently selected from the group of —H, —$C_{1-6}$ alkyl, —$C_{1-6}$ substituted alkyl, and —$C_{1-6}$ cycloalkyl, or $R_{22}$ and $R_{23}$ are taken together with the adjacent N to form a cycle selected from the group of

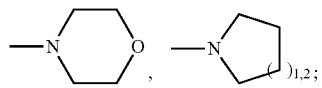

$R_{24}$ and $R_{25}$ are independently from the group of —H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl; and $Q_5$ is selected from the group of halogen and $SO_2R_3$.

2. The compound as claimed in claim 1, wherein X is phenyl or $C_{4-8}$ cycloalkenyl.

3. The compound as claimed in claim 2, wherein X is $C_{4-8}$ cycloalkenyl.

4. The compound as claimed in claim 2, wherein Y is —COOH.

5. The compound as claimed in claim 1, wherein Z is —CO—.

6. A method for treating a mammal infected with the HIV virus comprising administering to said mammal an HIV ameliorating amount of a compound as claimed in claim 1, together with one or more pharmaceutically acceptable carriers, excipients, and/or diluents.

* * * * *